(12) United States Patent
Masci et al.

(10) Patent No.: US 7,070,969 B1
(45) Date of Patent: Jul. 4, 2006

(54) **PLASMIN INHIBITORS FROM THE AUSTRALIAN BROWN SNAKE *PSEUDONAJA TEXTILIS TEXTILIS***

(75) Inventors: Pantaleone Paul Masci, Coorparo (AU); Martin Francis Lavin, Chapel Hill (AU); Patrick Joseph Gaffney, Harpenden (GB)

(73) Assignees: The University of Queensland, Brisbane (AU); National Institute of Biological Standards and Control, Hertfordshire (GB)

( * ) Notice: Subject to any disclaimer, the term of this patent is extended or adjusted under 35 U.S.C. 154(b) by 0 days.

(21) Appl. No.: 09/700,179

(22) PCT Filed: May 7, 1999

(86) PCT No.: PCT/AU99/00343

§ 371 (c)(1),
(2), (4) Date: Jul. 27, 2001

(87) PCT Pub. No.: WO99/58569

PCT Pub. Date: Nov. 18, 1999

(30) Foreign Application Priority Data

May 11, 1998 (AU) .................................... PP3450

(51) Int. Cl.
*C12N 9/99* (2006.01)
(52) U.S. Cl. ................... 435/184; 435/217; 424/94.64; 514/2; 514/12; 514/13; 530/324; 530/325

(58) Field of Classification Search ................ 435/184, 435/217; 424/94.64; 514/2, 12, 13; 530/324, 530/325
See application file for complete search history.

(56) References Cited

FOREIGN PATENT DOCUMENTS

WO    WO-99-58569    * 11/1999

OTHER PUBLICATIONS

Willmott et al. Fibrinolysis 1995, vol. 9, pp. 108.*
Fibrinolysis, vol. 9, No. 1, 1995, Willmot et al, A Novel Serine Protease Inhibitor from the Australian Brown Snake, *Pseudonaja textilis textilis*: Inhibition Kinetics, pp. 1-8.*
P.P. Masci, "The Effects of Australian Snake Venoms on Coagulation and Fibrinolysis", *Thesis* 163 pages Jul. 1986, Univ of Queensland, St. Lucia, Brisbane, Australia.
Fibrinolysis, vol. 9, No. 1, 1995, N. Willmot et al, "A Novel Serine Protease Inhibitor from the Australian Brown Snake, *Pseudonaja textilis textilis*: Inhibition Kinetics," pp. 1-8.

* cited by examiner

*Primary Examiner*—Christopher R. Tate
*Assistant Examiner*—B. Dell Chism
(74) *Attorney, Agent, or Firm*—Foley & Lardner LLP

(57) ABSTRACT

The invention provides novel single stage competitive inhibitors of plasmin from the Australian brown snake *Pseudonaja textilis textilis*. The invention also features polynucleotides and polynucleotide homologues encoding these inhibitors. Pharmaceutical compositions containing the plasmin inhibitors of the invention are also disclosed as well as methods useful for treatment of blood loss.

48 Claims, 14 Drawing Sheets

|  | 10 | 20 | 30 | 40 | 50 | 59 | |
|---|---|---|---|---|---|---|---|
| KDRPDFCELP | ADTGPCRVRF | PSFYYNPDZK | KCLZFIYGGC | EGNANNFITK | EECESTCGS | | TXLN1 |
| KDRPELCELP | PDTGPCRVRF | PSFYYNPDEQ | KCLEFIYGGC | EENANAFITK | EECESTCGG | | TXLN2 |
| KDRPKFCHLP | PKPGPCRAAI | PRFYYNPHSK | QCEKFIYGGC | HGNANKFKTP | DECNYTCLGVSL | | TAC |
| RPDFCLEP | PYTGPCKARI | IRYFYNAKAG | LCQTFVYGGC | RAKRNNFKSA | EDCMRTCGGA | | APRO |

FIG. 5

ATG AAG GAC CGG CCT GAT TTT TGT GAA CTG CCT GCT GAC ACC GGA CCA TGT
 M   K   D   R   P   D   F   C   E   L   P   A   D   T   G   P   C

AGA GTC AGA TTC CCA TCC TTG TAC TAC AAC CCA GAT GAA AAA AAA TGC CTC
 R   V   R   F   P   S   L   Y   Y   N   P   D   E   K   K   C   L

GAG TTT ATT TAT GGT GGA TGC GAA GGG AAT GCT AAC GAT TTT ATG ACC AAA
 E   F   I   Y   G   G   C   E   G   N   A   N   D   F   M   T   K

GAG GAG TGT GAA AGC ACG TGT GG(N) AGT
 E   E   C   E   S   T   C   G   S

FIG. 6

ATG AAG GAC CGG CCT GAG TTG TGT GAA CTG CCT CCT GAC ACC GGA CCA TGT
 M   K   D   R   P   E   L   C   E   L   P   P   D   T   G   P   C

AGA GTC AGA TTC CCA TCC TTG TAC AAC CCA GAT GAA CAA AAA TGC CTC
 R   V   R   F   P   S   L   Y   N   P   D   E   Q   K   C   L

GAG TTT ATT TAT GGT GGA TGC GAA GAG AAT GAT AAC GCT TTT ATG ACC AAA
 E   F   I   Y   G   G   C   E   E   N   D   N   A   F   M   T   K

GAG GAG TGT GAA AGC ACG TGT CC(N) GGT
 E   E   C   E   S   T   C   G    G

FIG. 7 ggagcttcatcatGTCTTCTGGAGGTCTTCTTCCTGCTGGGACTCCTCACCCTCTGGGAGGTG
CTGACCCCCGTCTCCAGCAAGGACCGTCCAGAGTTGTGTGAACTGCCTCCTGACACCGGACCATGTAGAGTC
AGATCCCCATCCTTCTACTACAACCCAGATGAACAAAAATGCCTAGAGTTTATTTATGGTGGATGCGAAGGG
AATGCTAACCAATTTTATCACCAAAGAGGAATGCGAAAGCACCTGTGCTGCCTGAatgaggagaccctcctg
gattggatcgacagttccaacttgacccaaagaccctgctttctgccctggaccacctgacaccccttcccc
caaccccaccctgactaattcctttctctgcaataaagctttggttccagct

FIG. 9

Txln 1

MSSGGLLLLLGLLTLWEVLTPVSSKDRPDFCELPADTGPCRVR
FPSFYYNPDEKKCLEFIYGGCEGNANNFITKEECESTCAA

*Txln 1*

ATGTCTTCTGGAGGTCTTCTTCTCCTGCTGGGACTCCTCACC
CTCTGGGAGGTGCTGACCCCGTCTCCAGCAAGGACCGTCCGGATTTCTG
TGAACTGCCTGCTGACACCGGACCATGTAGAGTCAGATTCCCATCCTTCT
ACTACAACCCAGATGAAAAAAGTGCCTAGAGTTTATTTATGGTGGATG
CGAAGGGAATGCTAACAATTTTATCACCAAAGAGGAATGCGAAAGCACC
TGTGCTGCCTGA

Txln 2

MSSGGLLLLLGLLTLWEVLTPVSSKDRPELCELPPDTGPCRVR
FPSFYYNPDEQKCLEFIYGGCEGNANNFITKEECESTCAA

*Txln 2*

ATGTCTTCTGGAGGTCTTCTTCTCCTGCTGGGACTCCTCACC
CTCTGGGAGGTGCTGACCCCGTCTCCAGCAAGGACCGTCCAGAGTTGTG
TGAACTGCCTCCTGACACCGGACCATGTAGAGTCAGATTCCCATCCTTCT
ACTACAACCCAGATGAACAAAAATGCCTAGAGTTTATTTATGGTGGATG
CGAAGGGAATGCTAACAATTTTATCACCAAAGAGGAATGCGAAAGCACC
TGTGCTGCCTGA

FIG. 10

Txln 3

MSSGGLLLLLGLLTLWEVLTPVSSKDRPNFCKLPAETGRCNAK
IPRFYYNPRQHQCIEFLYGGCGGNANNFKTIKECESTCAA

*Txln 3*

ATGTCTTCTGGAGGTCTTCTTCTCCTGCTGGGACTCCTCACC
CTCTGGGAGGTGCTGACCCCGTCTCCAGCAAGGACCGTCCAAATTTCTG
TAAACTGCCTGCTGAAACCGGACGATGTAATGCCAAAATCCCACGCTTCT
ACTACAACCCACGTCAACATCAATGCATAGAGTTTCTCTATGGTGGATGC
GGAGGGAATGCTAACAATTTTAAGACCATTAAGGAATGCGAAAGCACCT
GTGCTGCATGA

Txln 4

MSSGGLLLLLGLLTLWEVLTPVSSKDHPKFCELPADTGSCKGN
PVRFYYNADHHQCLKFIYGGCGGNANNFKTIEECKSTCAA

*Tx-4 n*

ATGTCTTCTGGAGGTCTTCTTCTCCTGCTGGGACTCCTCACC
CTCTGGGAGGTGCTGACCCCGTCTCCAGCAAGGACCATCCAAAATTCTG
TGAACTCCCTGCTGAAACCGGATCATGTAAAGGCAACGTCCCACGCTTCT
ACTACAACGCAGATCATCATCAATGCCTAAAATTTATTTATGGTGGATGT
GGAGGGAATGCTAACAATTTTAAGACCATAGAGGAAGGCAAAAGCACCT
GTGCTGCCTGA

FIG. 10 cont'd.

Txln 5

MSSGGLLLLLGLLTLWEVLTPVSSKDRPKFCELLPDTGSCEDF
TGAFHYSTRDRECIEFIYGGCGCNANNFITKEECESTCAA

*Txln 5*

ATGTCTTCTGGAGGTCTTCTTCTCCTGCTGGGACTCCTCACC
CTCTGGGAGGTGCTGACCCCCGTCTCCAGCAAGGACCGTCCAAAATTCTG
TGAACTGCTTCCTGACACCGGATCATGTGAAGACTTTACCGGAGCCTTCC
ACTACAGCACACGTGATCGTGAATGCATAGAGTTTATTTATGGTGGATGC
GGAGGGAATGCTAACAATTTTATCACCAAAGAGGAATGCGAAAGCACCT
GTGCTGCCTGA

Txln 6

MSSGGLLLLLGLLTLWEVLTPVSSKDRPKFCELPADIGPCDDF
TGAFHYSPREHECIEFIYGGCKGNANNFNTQEECESTCAA

*Txln 6*

ATGTCTTCTGGAGGTCTTCTTCTCCTGCTGGGACTCCTCACC
CTCTGGGAGGTGCTGACCCCCGTCTCCAGCAAGGACCGTCCAAAGTTCTG
TGAACTGCCTGCTGACATCGGACCATGGGATGACTTTACCGGAGCCTTCC
ACTACAGCCCACGTGAACATGAATGCATAGAGTTTATTTATGGTGGATGC
AAAGGGAATGCTAACAACTTTAATACCCAAGAGCAATGCGAAAGCACCT
GTGCTGCCTGA

FIG. 10 cont'd.

Consensus sequence for Textilinins

```
             1                                                                                  83
1.Txln1-     MSSGGLLLLLGLLTLWEVLTPVSSKDRPDFCELPADTGPCRVRFPSFYYNPDEKKCLEFIYGGCEGNANNFITKEECESTCAA
2.Txln2-     MSSGGLLLLLGLLTLWEVLTPVSSKDRPELCELPPDTGPCRVRFPSFYYNPDEQKCLEFIYGGCEGNANNFITKEECESTCAA
3.Txln3-     MSSGGLLLLLGLLTLWEVLTPVSSKDRPNFCKLPAETGRCNAKIPRFYYNPRQHQCIEFLYGGCGGNANNFKTIKECESTCAA
4.Txln4-     MSSGGLLLLLGLLTLWEVLTPVSSKDHPKFCELPADTGSCKGNPVRFYYNADHHQCLKFIYGGCGGNANNFKTIEECKSTCAA
5.Txln5-     MSSGGLLLLLGLLTLWEVLTPVSSKDRPKFCELLPDTGSCEDFTGAFHYSTRDRECIEFIYGGCGCNANNFITKEECESTCAA
6.Txln6-     MSSGGLLLLLGLLTLWEVLTPVSSKDRPKFCELPADIGPCDDFTGAFHYSPREHECIEFIYGGCKGNANNFNTQEECESTCAA
consensus-   MSSGGLLLLLGLLTLWEVLTPVSSKDrP fCeLpadtGpC  r p fyYnprek CieFiYGGC GNANNFiTkeECESTCAA
```

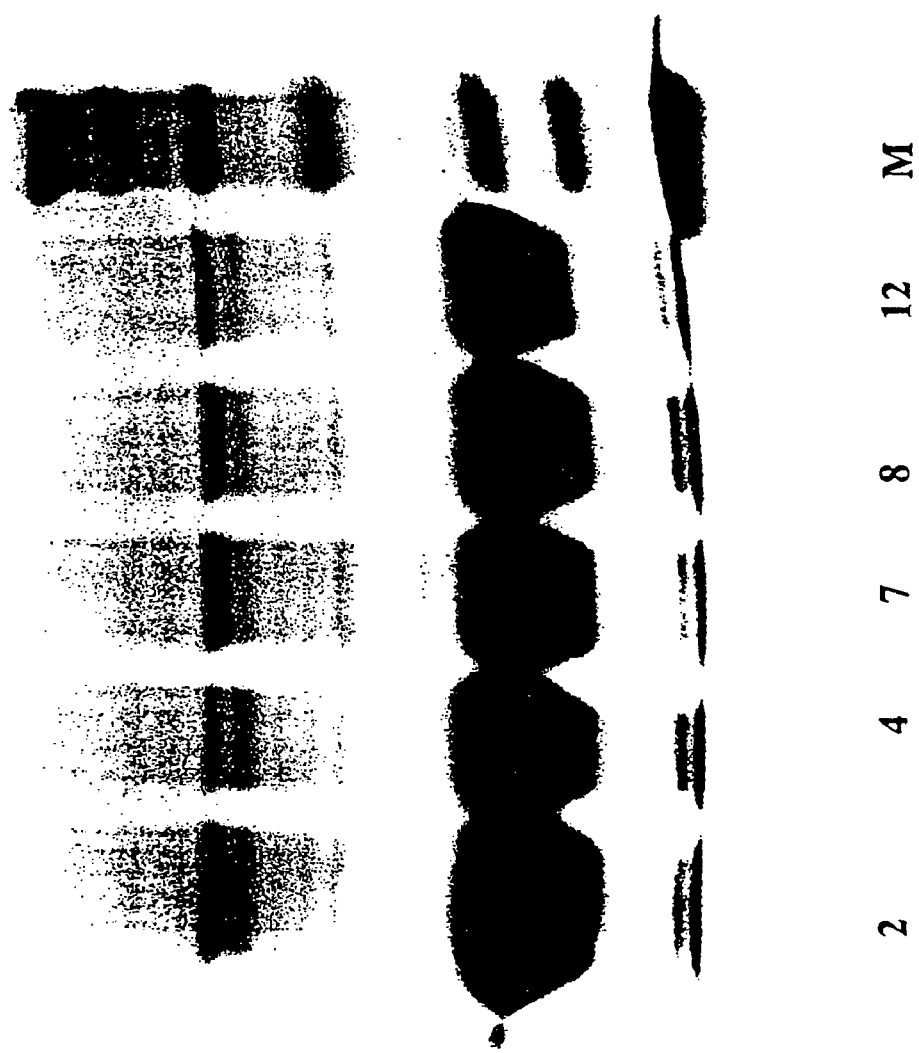

PLASMIN INHIBITORS FROM THE AUSTRALIAN BROWN SNAKE *PSEUDONAJA TEXTILIS TEXTILIS*

This application is a 371 of PCT/AU99/00343 filed May 7, 1999, which claims priority of Australian Provisional Application No. PP3450 filed May 11, 1998. The entirety of these applications are hereby incorporated by reference.

FIELD OF THE INVENTION

THIS INVENTION relates to anti-fibrinolytic agents and in particular, novel plasmin inhibitors having reduced propensity for causation of rebound thrombosis. The present invention also relates to amino acid sequences and nucleotide sequences encoding the novel plasmin inhibitors as well as to methods of producing these inhibitors and pharmaceutical compositions containing same.

BACKGROUND OF THE INVENTION

The blood loss associated with major forms of surgery has in the past been compensated by replacement therapy, which may involve fresh frozen plasma, fresh whole blood and platelet concentrates. With recent awareness of a variety of blood borne viral infections (Hepatitis B and C, and human immunodeficiency virus, HIV), the need to reduce blood loss during surgery is a major priority. Further anxiety has been generated within National Blood Transfusion Services concerning infectivity with agents related to Bovine Spongiform Encephalitis (BSE) and Creuzfeldt-Jacob's Disease (CJD) for which there is no reliable assay at the present time.

It has been established (Royston, 1990, *Blood Coagul. Fibrinol.* 1:53–69; Orchard et al, 1993, *Br. J. Haemat.* 85:596–599) that unfettered fibrinolytic activity via the plasminogen-plasmin pathway contributes to haemorrhage and that a plasmin inhibitor such as aprotinin helps alleviate blood loss. This seems to suggest that plasmin-mediated digestion of fibrin clots and components of the coagulation system may be of primary importance as a contribution to this haemorrhagic state (Orchard et al, 1993, supra).

The use of aprotinin during cardiopulmonary bypass (CPB) surgery is now commonplace (Royston, 1990, supra; Orchard et al, 1993, supra). In particular, Orchard et al (1993, supra) have demonstrated that the bovine source inhibitor aprotinin, as the active substance in the medicament Trasylol™, reduces blood loss in CPB patients by neutralisation of plasmin activity and does not affect platelet activity. This latter finding has been confirmed by other investigators (Ray and March, 1997, *Thromb. Haemost.* 78:1021–1026).

Aprotinin is a well-investigated serine protease inhibitor, or 'serpin'. It comprises 58 amino acids and acts to inhibit trypsin, α-chymotrypsin, plasmin as well as tissue and plasma kallikrein (Fritz and Wunderer, 1983, *Drug Res.* 33:479–494; Gebhard et al, 1986 *In "Proteinase Inhibitors"*, Barrett and Salvesen (eds.), Elsevier Science Publications BV pp 374–387). Aprotinin has also been found to react with thrombin and the plasminogen activators (tPA and uPA) (Willmott et al, 1995, *Fibrinolysis* 9:1–8).

Recent studies have shown that semi-synthetically generated homologues of aprotinin that contain other amino acids in place of lysine at position 15 of the amino acid sequence have a profile of action and specificity of action which differ distinctively from those of aprotinin (U.S. Pat. No. 4,595,674; Wenzel et al, 1985, *In "Chemistry of Peptides and Proteins"* Vol. 3). Some of these semi-synthetic aprotinin homologues have, for example, a strongly inhibiting action on elastase from pancreas and leucocytes. Other aprotinin homologues with arginine at position 15, alanine at position 17, and serine at position 42, are characterised by an inhibitory action which is distinctly greater than that of aprotinin on plasma kallikrein (cf. WO 89/10374).

Reference also may be made to U.S. Pat. No. 5,576,294 (Norris et al) which discloses human protease inhibitors of the same type as aprotinin. In particular, there is disclosed variants of human Kunitz-type protease inhibitor that preferentially inhibit neutrophil elastase, cathepsin G and/or proteinase 3. Compared to aprotinin, these variants have a net negative charge and are considered to have a reduced risk of kidney damage when administered to patients in large doses. In contrast, aprotinin has a nephrotoxic effect when administered in relatively high doses (Bayer, *Trasylol, Inhibitor of proteinase*; Glaser et al, *In "Verhandlungen der Deutchen Gesellschaft Für Innere Medizin*, 78. Kongress", Bergmann, München, 1972, pp 1612–1614). This nephrotoxicity is considered to be a consequence of the strongly net positive charge of aprotinin that causes it to bind to the negatively charged surfaces of kidney tubuli.

While there is no doubt that the anti-fibrinolytic clinical use of aprotinin reduces blood loss during vascular surgery, there is evidence of increased incidence of 'rebound thrombosis' which manifests in graft occlusion and perioperative myocardial infarction (Van der Meer et al, 1996, *Thromb. Haemost.* 75:1–3; Cosgrove et al, 1992, *Annals Thorac. Surg.* 54:1031–1038; Samama et al, 1994, *Thromb. Haemost.* 71:663–669). Consistent with these findings, it has been shown that aprotinin has a somewhat broad specificity and slow tight-binding kinetic action on plasmin (Willmott et al, 1995, supra). Accordingly, the increased incidence of rebound thrombosis may be a consequence of the tight binding of aprotinin to plasmin and concomitant irreversible neutralisation of the fibrinolytic system.

Until recently, there were no effective anti-fibrinolytic agents described in the prior art with reduced propensity for causation of rebound thrombosis compared to aprotinin. However, in a recent study, Willmott et al (1995, supra) isolated and characterised a plasmin inhibitor from the venom of the Australian brown snake, *Pseudonaja textilis textilis* with a promising kinetic profile in respect of rebound thrombosis. This isolated preparation of plasmin inhibitor, termed Textilinin (Txln), was found to consist of a single approximately 7 kDa protein, as assessed by sodium dodecyl sulphate (SDS) polyacrylamide gel electrophoresis (PAGE) and Coomassie blue staining. In contrast to the many serine protease enzymes inhibited by aprotinin, Txln was only shown to inhibit plasmin and trypsin. It was also shown to conform to a single stage competitive reversible mechanism for the binding of plasmin. In contrast, aprotinin conforms to a two stage reversible mechanism wherein enzyme and virgin inhibitor react to initially produce a loose non-covalent complex followed by a tightly bound, stable complex in which enzyme and inhibitor remain largely unchanged (Laskowski and Kato, 1980, *Annu. Rev. Biochem.* 49:593–626; Travis and Salvesen, 1983, *Annu. Rev. Biochem.* 52:655–709; Longstaff and Gaffney, 1991, *Biochemistry* 30:979–986). Moreover, Txln was shown to bind plasmin more rapidly (dissociation rate constant, $k^1=3.85\times 10^{-5}$ $sec^{-1}$ $M^{-1}$) and with a less avid $K_i$ (dissociation constant, $K_i=1.4\times10^{-1}$ M) than aprotinin (dissociation rate constant, $k_2=1.64\times10^{-5}$ $sec^{-1}$ $M^{-1}$; dissociation constant, $K^i=5.3\times10^{-11}$ M—this latter value being in close agreement with a previously reported value of $K_i=2\times10^{-10}$ M (Longstaff and Gaffney, 1992, *Fibrinolysis* 3:89–87)). It was suggested therefore that the Txln kinetic profile may be clinically more attractive with respect to rebound thrombosis than that of aprotinin in the management of perioperative and postoperative bleeding.

SUMMARY OF THE INVENTION

The present invention results from the unexpected discovery of two different plasmin inhibitors in the plasmin inhibitor preparation of Willmott et al (1995, supra) which was considered initially to be substantially homogeneous. Surprisingly, these plasmin inhibitors, termed Textilinin 1 (Txln 1) and Textilinin 2 (Txln 2) co-migrate with a molecular mass of about 7 kDa, as assessed by SDS-PAGE, and constitute only about 50% of the total protein (by weight) in the parent plasmin inhibitor preparation used by Willmott and colleagues. This, together with the fact that Txln 1 and Txln 2 each have a different kinetic profile compared to the parent preparation, suggests that the parent preparation contains other compounds which may interfere with plasmin inhibition. In particular, Txln 1 and Txln 2 have distinct amino acid sequences, somewhat similar kinetic profiles (Txln 1, $k_1=3.09\times10^{-6}$ $sec^{-1}$ $M^{-1}$; $K_i=3.5\times10^{-9}$ M; Txln 2, $k^1=8.20\times10^{-6}$ $sec^{-1}$ $M^{-1}$; $K_i=2.0\times10^{-9}$ M), while both inhibit blood loss in a murine model. Like the parent counterpart, Txln 1 and Txln 2 react only with plasmin and trypsin and therefore have high enzyme specificity compared to aprotinin. Moreover, comparison of the respective kinetic profiles of Txln 1, Txln 2 and aprotinin for plasmin reveals that Txln 1 and Txln 2 are between 10-fold and 100-fold less efficient than aprotinin in inhibiting plasmin. It has also been found that Txln1 and Txln 2 dissociate from plasmin between 10-fold and 100-fold more rapidly than aprotinin. Due to their high specificity for plasmin and low inhibitory efficiency, Txln 1 and Txln 2 may therefore have a therapeutic advantage, compared to aprotinin, to transiently affect the delicate balance between enzymes and inhibitors of the fibrinolytic system controlling the fluidity of blood.

The inventors have also found surprisingly that the Australian brown snake not only expresses transcripts encoding Txln 1 and Txln 2, but expresses transcripts encoding four additional plasmin inhibitors designated Textilinin 3, 4, 5 and 6 (ie., Txln 3, Txln 4, Txln 5 and Txln 6). Although these latter transcripts appear to be expressed at significantly lower levels compared to those encoding Txln 1 and Txln 2, they are highly homologous to Txln 1 and Txln 2 both at the nucleotide level and the deduced amino acid level.

Thus, in one aspect of the invention, there is provided a substantially pure preparation of a plasmin inhibitor characterised in that it is a single stage competitive inhibitor of plasmin.

Preferably, said single-stage competitive inhibitor has a dissociation constant for plasmin in the range of from $1\times10^{-8}$ $M^{-1}$ to $1\times10^{-10}$ $M^{-1}$, more preferably from $5\times10^{-8}$ $M^{-1}$ to $8\times10^{-9}$ $M^{-1}$, most preferably from $1\times10^{-9}$ $M^{-1}$ to $5\times10^{-9}$ $M^{-1}$.

The single-stage competitive inhibitor may have a dissociation rate constant for plasmin in the range of from $4\times10^{-5}$ $sec^{-1}$ $M^{-1}$ to $5\times10^{-7}$ $sec^{-1}$ $M^{-1}$, more preferably from $1\times10^{-6}$ $sec^{-1}$ $M^{-1}$ to $1\times10^{-7}$ $sec^{-1}$ $M^{-1}$, most preferably from $2\times10^{-6}$ $sec^{-1}$ $M^{-1}$ to $9\times10^{-6}$ $sec^{-1}$ $M^{-1}$.

Suitably, the single-stage competitive inhibitor comprises a polypeptide. Preferably, the polypeptide is selected from the group con of

[SEQ ID NO:2]
(a) Lys-Asp-Arg-Pro-Asp-Phe-Cys-Glu-Leu-Pro-Ala-Asp-Thr-Gly-Pro-Cys-Arg-Val-Arg-Phe-Pro-Ser-Phe-Tyr-Tyr-Asn-Pro-Asp-Glu-Lys-Lys-Cys-Leu-Glu-Phe-Ile-Tyr-Gly-Gly-Cys-Glu-Gly-Asn-Ala-Asn-Asn-Ph-Ile-Thr-Lys-Glu-Glu-Cys-Glu-Ser-Thr-Cys-Ala-Ala;

[SEQ ID NO:4]
(b) Lys-Asp-Arg-Pro-Glu-Leu-Cys-Glu-Leu-Pro-Pro-Asp-Thr-Gly-Pro-Cys-Arg-Val-Arg-Phe-Pro-Ser-Phe-Tyr-Tyr-Asn-Pro-Asp-Glu-Gln-Lys-Cys-Leu-Glu-Phe-Ile-Tyr-Gly-Gly-Cys-Glu-Gly-Asn-Ala-Asn-Asn-Phe-Ile-Thr-Lys-Glu-Glu-Cys-Glu-Ser-Thr-Cys-Ala-Ala;

[SEQ ID NO:6]
(c) Lys-Asp-Arg-Pro-Asn-Phe-Cys-Lys-Leu-Pro-Ala-Glu-Thr-Gly-Arg-Cys-Asn-Ala-Lys-Ile-Pro-Arg-Phe-Tyr-Tyr-Asn-Pro-Arg-Gln-His-Gln-Cys-Ile-Glu-Phe-Leu-Tyr-Gly-Gly-Cys-Gly-Gly-Asn-Ala-Asn-Asn-Phe-Lys-Thr-Ile-Lys-Glu-Cys-Glu-Ser-Thr-Cys-Ala-Ala;

[SEQ ID NO:8]
(d) Lys-Asp-His-Pro-Lys-Phe-Cys-Glu-Leu-Pro-Ala-Glu-Thr-Gly-Ser-Cys-Lys-Gly-Asn-Val-Pro-Arg-Phe-Tyr-Tyr-Asn-Ala-Asp-His-His-Gln-Cys-Leu-Lys-Phe-Ile-Tyr-Gly-Gly-Cys-Gly-Gly-Asn-Ala-Asn-Asn-Phe-Lys-Thr-Ile-Glu-Glu-Gly-Lys-Ser-Thr-Cys-Ala-Ala;

[SEQ ID NO:10]
(e) Lys-Asp-Arg-Pro-Lys-Phe-Cys-Glu-Leu-Leu-Pro-Asp-Thr-Gly-Ser-Cys-Glu-Asp-Phe-Thr-Gly-Ala-Phe-His-Tyr-Ser-Thr-Arg-Asp-Arg-Glu-CysIle-Glu-Phe-Ile-Tyr-Gly-Gly-Cys-Gly-Gly-Asn-Ala-Asn-Asn-Phe-Ile-Thr-Lys-Glu-Gln-Cys-Glu-Ser-Thr-Cys-Ala-Ala; and

[SEQ ID NO:12]
(f) Lys-Asp-Arg-Pro-Lys-Phe-Cys-Glu-Leu-Pro-Ala-Asp-Ile-Gly-Pro-Trp-Asp-Asp-Phe-Thr-Gly-Ala-Phe-His-Tyr-Ser-Pro-Arg-Glu-His-Glu-Cys-Ile-Glu-Phe-Ile-Tyr-Gly-Gly-Cys-Lys-Gly-Asn-Ala-Asn-Asn-Phe-Asn-Thr-Gln-Glu-Gln-Cys-Glu-Ser-Thr-Cys-Ala-Ala;

(g) a biologically-active fragment of any one of SEQ ID NO:2, 4, 6, 8, 10 and 12; and (h) a variant or derivative of any of the foregoing polypeptides of fragments thereof.

Preferably, the variant has the general formula:

KDZPZŸCZLBBZBGXCZXXXBXFÃYXBZZZZCBZFBYGGCXBNANNFXTXEE (SEQ ID NO: 45) (I),

CESTCAA

X is any amino acid;
Ÿ is a hydrophobic amino acid;
Ã is an aromatic amino acid;
Z is K, R, H, D, E, Q or N; and
B is a neutral amino acid, or P, A, G, S, T, V or L.
Preferably, the Z at position 3 is H or R.
Suitably, the Z at position 5 is K, N, E or D.
Preferably, the Ÿ at position 6 is F or L.
The Z at position 8 may be E or K.
Suitably, the B at position 10 is P or L.
Preferably, the B at position 11 is P or A.
The Z at position 12 is preferably E or D.
Suitably, the B at position 13 is T or I.

The X at position 15 may be P, S or R.
The Z at position 17 is suitably K, N, E, D or R.
Preferably, the X at position 18 is D, G, A or V.
Suitably, the X at position 19 is F, N, K or R.
The X at position 20 is preferably T, P, F or I.
The B at position 21 may be G, V or P.
Suitably, the X at position 22 is A, S or R.
Preferably, the Ã at position 24 is Y or H.
The X at position 26 is suitably S or N.
The B at position 27 is preferably P, A or T.
The Z at position 28 may be D or R.
Suitably, the Z at position 29 is E, D, H or Q.
Preferably, the Z at position 30 is H, K, R or Q.
The Z at position 31 may be K, Q or E.
The B at position 33 is preferably L or I.
The Z at position 34 is suitably E or K.
Suitably, the B at position 36 is L or I.
Preferably, the X at position 41 is E, G or K.
The B at position 42 may be C, but is preferably G.
Suitably, the X at position 48 is K, N or I.
Preferably, the X at position 50 is K, Q or I.
The polypeptide may comprise a leader peptide. Suitably, the leader peptide comprises the sequence of amino acids:—
Met-Ser-Ser-Gly-Gly-Leu-Leu-Leu-Leu-Leu-Gly-Leu-Leu-Thr-Leu-Trp-Glu-Val-Leu-Thr-Pro-Val-Ser-Ser [SEQ ID NO:14] a biologically-active fragment thereof, or variant or derivative of these.
Exemplary polypeptides which include the leader peptide may be selected from the group consisting of:—

According to another aspect, the invention provides an isolated polynucleotide encoding a polypeptide or biologically active fragment thereof, or variant or derivative of said fragment or polypeptide, according to the first-mentioned aspect. Suitably, said polynucleotide is selected from the group consisting of:

(1) AAGGACCGTCCGGATTTCTGTGAACTGCCTGCTGACACCGGAC
    CATGTAGAGTCAGATTCCCATCCTTCTACTACAACCCAGATGAA
    AAAAAGTGCTAGAGTTTATTTATGGTGGATGCGAAGGGAATGC
    TAACAATTTTTATCACCAAAGAGGAATGCGAAAGCACCTGTGCT
    GCCTGA [SEQ ID NO:1];

(2) AAGGACCGTCCAGAGTTGTGTGAACTGCCTCCTGACACCGGAC
    CATGTAGAGTCAGATTCCCATCCTTCTACTACAACCCAGATGAA
    CAAAAATGCCTAGAGTTTATTTATGGTGGATGCGAAGGGAATG
    CTAACAATTTTATCACCAAAGAGGAATGCGAAAGCACCTGTGC
    TGCCTGA [SEQ ID NO:3];

(3) AAGGACCGTCCAAATTTCTGTAAACTGCCTGCTGAAACCGGAC
    GATGTAATGCCAAAATCCCACGCTTCTACTACAACCCACGTCAA
    CATCAATGCATAGAGTTTCTCTATGGTGGATGCGGAGGGAATG
    CTAACAATTTTAAGACCATTAAGGAATGCGAAAGCACCTGTGC
    TGCATGA [SEQ ID NO:5];

(4) AAGGACCATCCAAAATTCTGTGAACTCCCTGCTGAAACCGGAT
    CATGTAAAGGCAACGTCCCACGCTTCTACTACAACGCAGATCA
    TCATCAATGCCTAAAATTTATTTATGGTGGATGTGGAGGGAATG
    CTAACAATTTTAAGACCATAGAGGAAGGCAAAAGCACCTGTGC
    TGCCTGA [SEQ ID NO:7];

i.  Met-Ser-Ser-Gly-Gly-Leu-Leu-Leu-Leu-Leu-Gly-Leu-Leu-Thr-Leu-Trp-
    Glu-Val-Leu-Thr-Pro-Val-Ser-Ser-Lys-Asp-Arg-Pro-Asp-Phe-Cys-Glu-
    Leu-Pro-Ala-Asp-Thr-Gly-Pro-Cys-Arg-Val-Arg-Phe-Pro-Ser-Phe-Tyr-Tyr-
    Asn-Pro-Asp-Glu-Lys-Lys-Cys-Leu-Glu-Phe-Ile-Tyr-Gly-Gly-Cys-Glu-
    Gly-Asn-Ala-Asn-Asn-Phe-Ile-Thr-Lys-Glu-Glu-Cys-Glu-Ser-Thr-Cys-Ala-
    Ala [SEQ ID NO:16];

ii. Met-Ser-Ser-Gly-Gly-Leu-Leu-Leu-Leu-Leu-Gly-Leu-Leu-Thr-Leu-Trp-
    Glu-Val-Leu-Thr-Pro-Val-Ser-Ser-Lys-Asp-Arg-Pro-Glu-Leu-Glu-Leu-
    Pro-Pro-Asp-Thr-Gly-Pro-Cys-Arg-Val-Arg-Phe-Pro-Ser-Phe-Tyr-Tyr-Asn-
    Pro-Asp-Glu-Gln-Lys-Cys-Leu-Glu-Phe-Ile-Tyr-Gly-Gly-Cys-Glu-Gly-
    Asn-Ala-Asn-Asn-Phe-Ile-Thr-Lys-Glu-Glu-Cys-Glu-Ser-Thr-Cys-Ala-Ala
    [SEQ ID NO:18];

iii Met-Ser-Ser-Gly-Gly-Leu-Leu-Leu-Leu-Leu-Gly-Leu-Leu-Thr-Leu-Trp-
    Glu-Val-Leu-Thr-Pro-Val-Ser-Ser-Lys-Asp-Arg-Pro-Asn-Phe-Cys-Lys-
    Leu-Pro-Ala-Glu-Thr-Gly-Arg-Cys-Asn-Ala-Lys-Ile-Pro-Arg-Phe-Tyr-Tyr-
    Asn-Pro-Arg-Gln-His-Gln-Cys-Ile-Glu-Phe-Leu-Tyr-Gly-Gly-Cys-Gly-Gly-
    Asn-Ala-Asn-Asn-Phe-Lys-Thr-Ile-Lys-Glu-Cys-Glu-Ser-Thr-Cys-Ala-Ala
    [SEQ ID NO:20];

iv. Met-Ser-Ser-Gly-Gly-Leu-Leu-Leu-Leu-Leu-Gly-Leu-Leu-Thr-Leu-Trp-
    Glu-Val-Leu-Thr-Pro-Val-Ser-Ser-Lys-Asp-His-Pro-Lys-Phe-Cys-Glu-Leu-
    Pro-Ala-Glu-Thr-Gly-Ser-Cys-Lys-Gly-Asn-Val-Pro-Arg-Phe-Tyr-Tyr-Asn-
    Ala-Asp-His-His-Gln-Cys-Leu-Lys-Phe-Ile-Tyr-Gly-Gly-Cys-Gly-Gly-Asn-
    Ala-Asn-Asn-Phe-Lys-Thr-Ile-Glu-Glu-Gly-Lys-Ser-Thr-Cys-Ala-Ala [SEQ
    ID NO:22];

v.  Met-Ser-Ser-Gly-Gly-Leu-Leu-Leu-Leu-Leu-Gly-Leu-Leu-Thr-Leu-Trp-
    Glu-Val-Leu-Thr-Pro-Val-Ser-Ser-Lys-Asp-Arg-Pro-Lys-Phe-Cys-Glu-Leu-
    Leu-Pro-Asp-Thr-Gly-Ser-Cys-Glu-Asp-Phe-Thr-Gly-Ala-Phe-His-Tyr-Ser-
    Thr-Arg-Asp-Arg-Glu-Cys-Ile-Glu-Phe-Ile-Tyr-Gly-Gly-Cys-Gly-Gly-Asn-
    Ala-Asn-Asn-Phe-Ile-Thr-Lys-Glu-Glu-Cys-Glu-Ser-Thr-Cys-Ala-Ala;
    [SEQ ID NO:24]; and vi. Met-Ser-Ser-Gly-Gly-Leu-Leu-Leu-Leu-Leu-Gly-Leu-Leu-Thr-Leu-Trp-
    Glu-Val-Leu-Thr-Pro-Val-Ser-Ser-Lys-Asp-Arg-Pro-Lys-Phe-Cys-Glu-Leu-
    Pro-Ala-Asp-Ile-Gly-Pro-Trp-Asp-Asp-Phe-Thr-Gly-Ala-Phe-His-Tyr-Ser-
    Pro-Arg-Glu-His-Glu-Cys-Ile-Glu-Phe-Ile-Tyr-Gly-Gly-Cys-Lys-Gly-Asn-
    Ala-Asn-Asn-Phe-Asn-Thr-Gln-Glu-Gln-Cys-Glu-Ser-Thr-Cys-Ala-Ala;
    [SEQ ID NO:26].

-continued (5) AAGGACCGTCCAAAATTCTGTGAACTGCTTCCTGACACCGGATC
ATGTGAAGACTTTACCGGAGCCTTCCACTACAGCACACGTGATC
GTGAATGCATAGAGTTTATTTATGGTGGATGCGGAGGGAATGC
TAACAATTTTATCACCAAAGAGGAATGCGAAAGCACCTGTGCT
GCCTGA [SEQ ID NO:9];

(6) AAGGACCGTCCAAAGTTCTGTGAACTGCCTGCTGACATCGGAC
CATGGGATGACTTTACCGGAGCCTTCCACTACAGCCCACGTGA
ACATGAATGCATAGAGTTTATTTATGGTGGATGCAAAGGGAAT
GCTAACAACTTTAATACCCAAGAGCAATGCGAAAGCACCTGTG
CTGCCTGA [SEQ ID NO:11]:

(7) a polynucleotide fragment of any one of SEQ ID NOS 1, 3, 5, 7, 9, and 11 which fragment encodes a biologically-active polypeptide fragment of any one of SEQ ID NO:2, 4, 6, 8, 10 and 12; and (8) a polynucleotide homologue of any of the foregoing sequences.

The polynucleotide preferably comprises a nucleotide sequence encoding a leader peptide. Suitably, said nucleotide sequence comprises the sequence of nucleotides:—

ATGTCTTCTGGAGGTCTTCTTCTCCTGCTGGGACTCCTCA

CCCTCTGGGAGGTGCTGACCCCCGTCTCCAGC [SEQ ID NO:13] or a biologically active fragment thereof, or a polynucleotide homologue of these.

Exemplary polynucleotides comprising said nucleotide sequence may be selected from the group consisting of:

1) ATGTCTTCTGGAGGTCTTCTTCTCCTGCTGGGACTCCTCACCCTCTG
GGAGGTGCTGACCCCCGTCTCCAGCAAGGACCGTCCGGATTTCTGT
GAACTGCCTGCTGACACCGGACCATGTAGAGTCAGATTCCCATCCT
TCTACTACAACCCAGATGAAAAAAGTGCCTAGAGTTTATTTATTGG
TGGATGCGAAGGGAATGCTAACAATTTTATCACCAAAGAGGAATG
CGAAAGCACCTGTGCTGCCTGA [SEQ ID NO:15];

2) ATGTCTTCTGGAGGTCTTCTTCTCCTGCTGGGACTCCTCACCCTCTG
GGAGGTGCTGACCCCCGTCTCCAGCAAGGACCGTCCAGAGTTGTGT
GAACTGCCTCCTGACACCGGACCATGTAGAGTCAGATTCCCATCCT
TCTACTACAACCCAGATGAACAAAAATGCCTAGAGTTTATTTATGG
TGGATGCAAGGGAATGCTAACAATTTTATCACCAAAGAGGAATG
CGAAAGCACCTGTGCTGCCTGA [SEQ ID NO:17];

3) ATGTCTTCTGGAGGTCTTCTTCTCCTGCTGGGACTCCTCACCCTCTG
GGAGGTGCTGACCCCCGTCTCCAGCAAGGACCGTCCAAATTTCTGT
AAACTGCCTGCTGAAACCGGACGATGTAATGCCAAAATCCCACGC
TTCTACTACAACCCACGTCAACATCAATGCATAGAGTTTCTCTATG
GTGGATGCGGAGGGAATGCTAACAATTTTAAGACCATTAAGGAAT
GCGAAAGCACCTGTGCTGCATGA [SEQ ID NO:19];

4) ATGTCTTCTGGAGGTCTTCTTCTCCTGCTGGGACTCCTCACCCTCTG
GGAGGTGCTGACCCCCGTCTCCAGCAAGGACCATCCAAAATTCTGT
GAACTCCCTGCTGAAACCGGATCATGTAAAGGCAACGTCCCACGC
TTCTACTACAACGCAGATCATCATCAATGCCTAAAATTTATTTATG
GTGGATGTGGAGGGAATGCTAACAATTTTAAGACCATAGAGGAAG
GCAAAAGCACCTGTGCTGCCTGA [SEQ ID NO:21];

5) ATGTCTTCTGGAGGTCTTCTTCTCCTGCTGGGACTCCTCACCCTCTG
GGAGGTGCTGACCCCCGTCTCCAGCAAGGACCGTCCAAAATTCTGT
GAACTGCTTCCTGACACCGGATCATGTGAAGACTTTACCGGAGCCT
TCCACTACAGCACACGTGATCGTGAATGCATAGAGTTTATTTATGG
TGGATGCGGAGGGAATGCTAACAATTTTATCACCAAAGAGGAATG
CGAAAGCACCTGTGCTGCCTGA [SEQ ID NO:23];

6) ATGTCTTCTGGAGGTCTTCTTCTCCTGCTGGGACTCCTCACCCTCTG
GGAGGTGCTGACCCCCGTCTCCAGCAAGGACCGTCCAAAGTTCTGT
GAACTGCCTGCTGACATCGGACCATGGGATGACTTTACCGGAGCCT
TCCACTACAGCCCACGTGAACATGAATGCATAGAGTTTATTTATGG
TGGATGCAAAGGGAATGCTAACAACTTTAATACCCAAGAGCAATG
CGAAAGCACCTGTGCTGCCTGA [SEQ ID NO:25]; and -continued 7) GGAGCTTCATCATGTCTTCTGGAGGTCTTCTTCTCCTGCTGGGACTC
CTCACCCTCTGGGAGGTGCTGACCCCCGTCTCCAGCAAGGACCGTC
CAGAGTTGTGTGAACTGCCTCCTGACACCGGACCATGTAGAGTCAG
ATCCCCATCCTTCTACTACAACCCAGATGAACAAAAATGCCTAGAG
TTTATTTATGGTGGATGCGAAGGGAATGCTAACCAATTTTATCACC
AAAGAGGAATGCGAAAGCACCTGTGCTGCCTGAATGAGGAGACCC
TCCTGGATTGGATCGACAGTTCCAACTTGACCCAAAGACCCTGCTT
CTGCCCTGGACCACCCTGGACACCCTTCCCCCAAACCCCACCCTGG
ACTAATTCCTTTTCTCTGCAATAAAGCTTTGGTTCCAGCT [SEQ ID
NO:43]

In yet another aspect, the invention provides a pharmaceutical composition for alleviating blood loss in a patient, said composition comprising a polypeptide or a biological fragment thereof, or a variant or derivatives of these ("therapeutic agents") and a pharmaceutically acceptable carrier.

According to yet another aspect of the invention, there is provided a method for alleviating blood loss comprising the step of administering to a patient in need of such treatment a therapeutically effective dosage of a therapeutic agent of the invention in combination with a pharmaceutically acceptable carrier.

In a still further aspect, the invention resides in an anti-tumour agent comprising a polypeptide, polypeptide fragment, variant or derivative according to the invention conjugated with an anti-fibrin antibody.

BRIEF DESCRIPTION OF THE DRAWINGS

In order that the invention may be readily understood and put into practical effect, preferred embodiments will now be described by way of example with reference to the accompanying drawings in which:

FIG. 5 shows the amino acid sequences for Txln 1 (SEQ ID NO: 46) and Txln 2 (SEQ ID NO: 47), as well as those of Taicotoxin associated plasmin inhibitor (TAC) (SEQ ID NO: 48) and aprotinin (APRO) (SEQ ID NO: 49). The sequences were aligned according to the location of the six cysteines.

FIG. 6 lists a partial cDNA sequence of Txln 1(SEQ ID NOS 50–51). The amino acid sequence encoded by this partial sequence is shown below the nucleotide sequence in single letter code. The letter "N" denotes a non-characterized nucleotide.

FIG. 7 lists a partial cDNA sequence of Txln 2(SEQ ID NO: 52–53). The amino acid sequence encoded by this partial sequence is shown below the nucleotide sequence in single letter code. The letter "N" denotes a non-characterized nucleotide.

FIG. 9 lists the Txln 1 cDNA sequence (SEQ ID NO: 54) derived from nucleotide sequence analysis of the 5' and 3' RACE products.

FIG. 10 shows the nucleotide and deduced amino acid sequences (SEQ ID NOS. 55–66, respectively, in order of appearance) relating to respective proforms of Txln 1–6.

FIG. 11 shows a sequence comparison of Textilinin polypeptide sequences using the PILEUP program of the GCG Wisconsin Suite. Regions of sequence homology are indicated by SEQ ID NO 70 (YGGC), SEQ ID NO 69 (NANNF), and SEQ ID NO 68 (ECESTCAA).

FIG. 12 refers to a 15% SDS polyacrylamide gel electrophoresis under reducing conditions of Textilinin-GST fusion proteins expressed from various colonies harbouring pGEM-2T-Txln 1 recombinant clones. Colonies were selected by PCR screeening using sequence-specific primers. Numerals denote clone designation number.

DETAILED DESCRIPTION

1. Definitions

Figure 1:
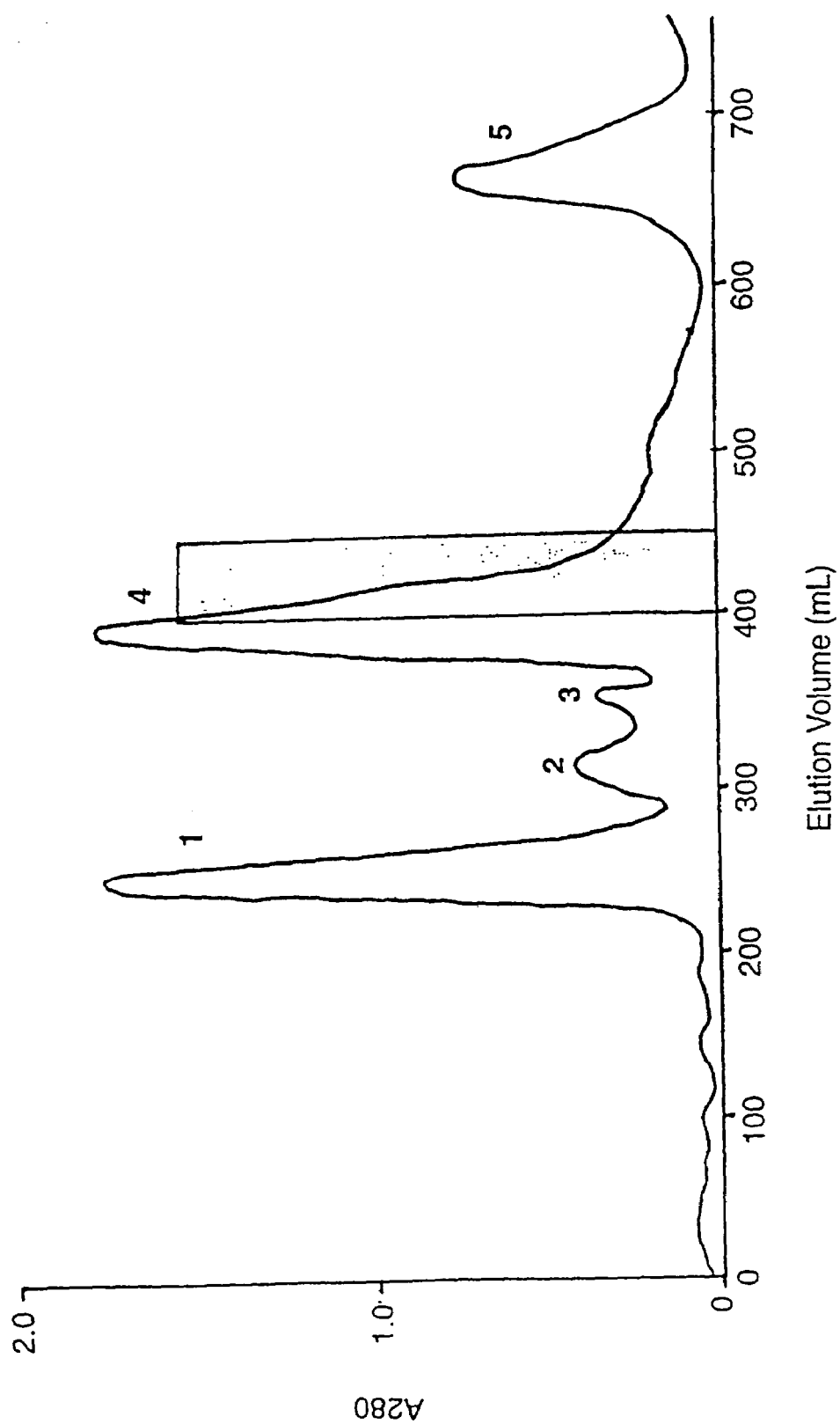
FIG. 1 shows a Sephacryl™ S-300 elution profile of venom from Australian brown snake. Five protein peaks (1–5) were obtained and plasmin inhibitory activity (e.g. Txln) was obtained on the shoulder peak 4 which comprises about 2% of the total protein applied to the column.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

By "biologically-active fragment" means a fragment of a substantially full-length parent polypeptide wherein the fragment retains the activity of the parent polypeptide. For example, in the case of a biologically active fragment of a polypeptide according to SEQ ID NO:2, 4, 6, 8, 10 and 12, the polypeptide fragment must retain the single stage competitive inhibition properties of the parent polypeptide with respect to plasmin.

The term "biological sample" as used herein refers to a sample that may be untreated, treated, diluted or concentrated from a patient. Suitably, the biological sample is selected from foetal cells, and tissue samples including tissue from the caudate and/or putamen regions of the brain, and the like.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions, or deletions that provide for functional equivalent molecules.

"Homology" refers to the percentage number of amino acids that are identical or constitute conservative substitutions as defined in Table 1 below. Homology may be determined using sequence comparison programs such as GAP (Deveraux et al. 1984, *Nucleic Acids Research* 12, 387–395) which is incorporated herein by reference. In this way sequences of a similar or substantially different length to those cited herein might be compared by insertion of gaps into the alignment, such gaps being determined, for example, by the comparison algorithm used by GAP.

"Hybridisation" is used herein to denote the pairing of complementary nucleotide sequences to produce a DNA—DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridize efficiently, such as the classical A-T and G-C base pair mentioned above. Mismatches are other combinations of nucleotides that do not hybridise efficiently.

By "isolated" is meant material that is substantially or essentially free from components that normally accompany it in its native state. For example, an "isolated polynucleotide", as used herein, refers to a polynucleotide, which has been purified from the sequences which flank it in a naturally occurring state, e.g., a DNA fragment which has been removed from the sequences which are normally adjacent to the fragment.

By "obtained from" is meant that a sample such as, for example, a nucleic acid extract is isolated from, or derived from, a particular source of the host. For example, the nucleic acid extract may be obtained from tissue isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

By "operably linked" is meant that transcriptional and translational regulatory nucleic acids are positioned relative to a nucleotide sequence encoding a polypeptide or fragment thereof in such a manner that transcription of said nucleotide sequence is initiatable and terminatable, respectively.

The term "patient" refers to patients of human or other animal origin and includes any individual it is desired to examine or treat using the methods of the invention. However, it will be understood that "patient" does not imply that symptoms are present.

The term "polynucleotide" or "nucleic acid" as used herein designates mRNA, RNA, cRNA, cDNA or DNA. The term typically refers to oligonucleotides greater than 30 nucleotides in length.

By "pharmaceutically-acceptable carrier" is meant a solid or liquid filler, diluent or encapsulating substance that may be safely used in systemic administration.

The term "polynucleotide homologues" generally refers to polynucleotides that hybridise with a reference polynucleotide under substantially stringent conditions.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. By "substantially complementary", it is meant that the primer is sufficiently complementary to hybridize with a target nucleotide sequence. Preferably, the primer contains no mismatches with the template to which it is designed to hybridize but this is not essential. For example, non-complementary nucleotides may be attached to the 5'-end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to an oligonucleotide probe that binds to another nucleic acid, often called the "target nucleic acid", through complementary base pairing. Probes may bind target nucleic acids lacking complete sequence complementarity with the probe, depending on the stringency of the hybridisation conditions. Probes can be directly or indirectly labelled.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the a nucleotide sequence.

By "recombinant polypeptide" is meant a polypeptide made using recombinant techniques, i.e., through the expression of a recombinant polynucleotide.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Dr. Madison, Wis., USA) or by inspection and the best alignment (i.e., resulting in the highest percentage homology over the comparison window) generated by any of the various methods selected.

"Sequence identity" refers to sequences that are identical (i.e., on a nucleotide-by-nucleotide or amino acid-by-amino acid basis) over the window of comparison. The term "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence similarity.

"Stringency" as used herein, refers to the temperature and ionic strength conditions, and presence or absence of certain organic solvents, during hybridisation. The higher the stringency, the higher will be the degree of complementarity between immobilised nucleotide sequences and the labelled polynucleotide sequence.

"Stringent conditions" refers to temperature and ionic conditions under which only nucleotide sequences having a high frequency of complementary bases will hybridize. The stringency required is nucleotide sequence dependent and also depends upon the various components present during hybridisation. Generally, stringent conditions are selected to be about 10 to 20° C. lower than the thermal melting point ($T_m$) for the specific sequence at a defined ionic strength and pH. The $T_m$ is the temperature (under defined ionic strength and pH) at which 50% of a target sequence hybridises to a complementary probe.

The term "substantially pure" as used herein describes a compound, eg., a peptide which has been separated from components that naturally accompany it. Typically, a compound is substantially pure when at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, eg., in the case of peptides by chromatography, gel electrophoresis or HPLC analysis. A compound, eg., a peptide is also substantially purified when it is essentially free of naturally associated components when it is separated from the native contaminants which accompany it in its natural state.

The term "variant" refers to polypeptides in which one or more amino acids have been replaced by different amino acids. It is well understood in the art that some amino acids may be changed to others with broadly similar properties without changing the nature of the activity of the polypeptide (conservative substitutions).

By "vector" is meant a nucleic acid molecule, preferably a DNA molecule derived, for example, from a plasmid, bacteriophage, or plant virus, into which a synthetic nucleic acid sequence may be inserted or cloned. A vector preferably contains one or more unique restriction sites and may be capable of autonomous replication in a defined host cell including a target cell or tissue or a progenitor cell or tissue thereof, or be integratable with the genome of the defined host such that the cloned sequence is reproducible. Thus, by "expression vector" is meant any autonomous element capable of directing the synthesis of a protein. Such expression vectors are well known by practitioners in the art. The vector may also include a selection marker such as an antibiotic resistance gene that can be used for selection of suitable transformants. Examples of such resistance genes are well known to those of skill in the art.

As used herein, underscoring or italicising the name of a gene shall indicate the gene, in contrast to its protein product, which is indicated by the name of the gene in the absence of any underscoring or italicising. For example, "Txln 1" shall mean the Txln 1 gene, whereas "Txln 1" shall indicate the protein product of the "Txln 1" gene.

Throughout this specification, unless the context requires otherwise, the words "comprise", "comprises" and "comprising" will be understood to imply the inclusion of a stated integer or group of integers but not the exclusion of any other integer or group of integers.

2. Plasmin Inhibitors of the Invention

The present invention provides a substantially pure preparation of a plasmin inhibitor characterised in that it is a single stage competitive inhibitor of plasmin. In a preferred embodiment, the single-stage competitive inhibitor has dissociation constant for plasmin in the range of from $1\times10^{-8}$ $M^{-1}$ to $1\times10^{-10}$ $M^{-1}$, more preferably from $5\times10^{-8}$ $M^{-1}$ to $8\times10^{-9}$ $M^{-1}$, most preferably from $1\times10^{-9}$ $M^{-1}$ to $5\times10^{-9}$ $M^{-1}$. The single-stage competitive inhibitor preferably has a dissociation rate constant for plasmin in the range of from $4\times10^{-5}$ $sec^{-1}$ $M^{-1}$ to $5\times10^{-7}$ $sec^{-1}$ $M^{-1}$, more preferably from $1\times10^{-6}$ $sec^{-1}$ $M^{-1}$ to $1\times10^{-7}$ $sec^{-1}$ $M^{-1}$, and most preferably from $2\times10^{-6}$ $sec^{-1}$ $M^{-1}$ to $9\times10^{-6}$ $sec^{-1}$ $M^{-1}$.

2.1 Textilinin Polypeptides

The plasmin inhibitor is preferably a Textilinin polypeptide. Accordingly, the present invention provides an isolated polypeptide according to SEQ ID NOS 2, 4, 6, 8, 10, and 12, or biologically active fragment respectively thereof, or variant or derivative of these. SEQ ID NO:2 and SEQ ID NO:4 correspond respectively to the novel about 7 kDa Textilinin 1 (Txln 1) and Textilinin 2 (Txln 2) polypeptides obtained from *Pseudonaja textilis textilis*, as described more fully hereinafter. SEQ ID NOS 6, 8, 10 and 12 correspond to homologous polypeptides deduced from polynucleotides obtained from *Pseudonaja textilis textilis*.

In one embodiment, the isolated polypeptide may comprise a leader peptide according to SEQ ID NO:14 or biologically active fragment thereof, or variant or derivative of these. In this regard, the invention also provides an isolated polypeptide according to SEQ ID NO:16, 18, 20, 22, 24 and 26.

2.2 Textilinin Polypeptide Fragments

The invention contemplates biologically active fragments of a Textilinin polypeptide according to the invention. Exemplary fragments of this type include deletion mutants and small peptides, for example of at least 15, preferably at least 20 and more preferably at least 30 contiguous amino acids of a polypeptide according to SEQ ID NO:2, 4, 6, 8, 10, 12, 16, 18, 20, 22, 24 and 26, which fragment consists retains single stage competitve inhibition of plasmin.

2.3 Textilinin Polypeptide Variants

With regard to variant polypeptides of the invention, it will be understood that such variants should retain single stage competitive inhibition of plasmin of the parent or reference polypeptide. Exemplary conservative substitutions in a parent polypeptide may be made according to Table 1:

TABLE 1

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Substantial changes in function are made by selecting substitutions that are less conservative than those shown in TABLE 1. Other replacements would be non-conservative substitutions and relatively fewer of these may be tolerated. Generally, the substitutions which are likely to produce the greatest changes in a polypeptide's properties are those in which: (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp); or (d) a residue having a bulky side chain (e.g., Phe or Trp) is substituted for, or by, one having a smaller side chain (e.g., Ala, Ser)or no side chain (e.g., Gly).

In general, variants comprise regions that are at least 75% homologous, more suitably at least 80%, preferably at least 85%, and most preferably at least 90% homologous to the basic sequences as for example shown in SEQ ID NO:2, 4, 6, 8, 10 and 12. In an alternate embodiment, variants comprise regions that have at least 70%, more suitably at least 80%, preferably at least 90%, and most preferably at least 95% identity over a parent amino acid sequence of identical size ("comparison window") or when compared to an aligned sequence in which the alignment is performed by a computer homology program known in the art. What constitutes suitable variants may be determined by conventional techniques. For example, nucleic acids encoding polypeptides according to SEQ ID NO: 2, 4, 6, 8, 10 and 12 can be mutated using either random mutagenesis for example using transposon mutagenesis, or site-directed mutagenesis. The resultant DNA fragments are then cloned into suitable expression hosts such as *E. Coli* using conventional technology and clones that retain the desired activity are detected. As mentioned above, the desired activity will include single stage competitive inhibition of plasmin of the parent or reference polypeptide. Where the clones have been derived using random mutagenesis techniques, positive clones would have to be sequenced in order to detect the mutation. The term "variant" also includes naturally occurring allelic variants.

In a preferred embodiment, the variant has the general formula:

```
            KDZPZŸCZLBBZBGXCZXXXBXFÄYXBZZZZCBZFBYGGCXBNANNFXTXE (SEQ ID NO: 45) (I),
ECESTCAA
```

X is any amino acid;
Ÿ is a hydrophobic amino acid;
Ä is an aromatic amino acid;
Z is K, R, H, D, E, Q or N; and
B is a neutral amino acid, or P, A, G, S, T, V or L.

2.4 Textilinin Polypeptide Derivatives

With reference to suitable derivatives of the invention, such derivatives include amino acid deletions and/or additions to a Textilinin polypeptide according to the invention such as, for example, SEQ ID NO:2, 4, 6, 8, 10 ans 12, or variants thereof, wherein said derivatives retain single stage competitve inhibition of plamin. "Additions" of amino acids may include fusion of the polypeptides, fragments thereof or variants of these with other polypeptides or proteins. In this regard, it will be appreciated that the polypeptides, polypeptide fragments or variants of the invention may be incorporated into larger polypeptides, and such larger polypeptides may also be expected to retain the single stage competitve inhibition of plasmin mentioned above.

The Textilinin polypeptides of the invention, fragments thereof or variants of these may be fused to a further protein, for example, which is not derived from the original host. The other protein may, by way of example, assist in the purification of the protein. For instance a polyhistidine tag, or a maltose binding protein may be used in this respect as described in more detail below. Alternatively, it may produce an antigenic response or immunogenic response that is effective against the polypeptide or fragment thereof. Other possible fusion proteins are those which produce an immunomodulatory response. Particular examples of such proteins include Protein A or glutathione S-transferase (GST).

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention.

Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4, 6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A list of unnatural amino acids contemplated by the present invention is shown in TABLE 2.

TABLE 2

| Non-conventional amino acid | Non-conventional amino acid |
| --- | --- |
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |

TABLE 2-continued

| Non-conventional amino acid | Non-conventional amino acid |
| --- | --- |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl carbamylmethyl)glycine | N-(N-(3,3-diphenylpropyl carbamylmethyl)glycine |
| 1-carboxy-1-(2,2-diphenyl-ethyl amino)cyclopropane | |

The invention also contemplates the use of crosslinkers, for example, to stabilise 3D conformations of the peptides or peptide homologs of the invention, using homo-bifunctional cross linkers such as bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety or carbodiimide. In addition, peptides can be conformationally constrained, for example, by introduction of double bonds between $C_\alpha$ and $C_\beta$ atoms of amino acids, by incorporation of $C_\alpha$ and $N_\alpha$-methylamino acids, and by formation of cyclic peptides or analogues by introducing covalent bonds such as forming an amide bond between the N and C termini between two side chains or between a side chain and the N or C terminus of the peptides or analogues. For example, reference may be made to: Marlowe (1993, *Biorganic & Medicinal Chemistry Letters* 3:437–44, hereby incorporated by reference) which describes peptide cyclization on TFA resin using trimethylsilyl (TMSE) ester as an orthogonal protecting group; Pallin and Tam (1995, *J. Chem. Soc. Chem. Comm.* 2021–2022, hereby incorporated by reference) which describes the cyclization of unprotected peptides in aqueous solution by oxime formation; Algin et al (1994, *Tetrahedron Letters* 35: 9633–9636, hereby incorporated by reference) which discloses solid-phase synthesis of head-to-tail cyclic peptides via lysine side-chain anchoring; Kates et al (1993, *Tetrahedron Letters* 34: 1549–1552, hereby incorporated by reference) which describes the production of head-to-tail cyclic peptides by three-dimensional solid phase strategy; Tumelty et al (1994, *J. Chem. Soc. Chem. Comm.* 1067–1068, hereby incorporated by reference) which describes the synthesis of cyclic peptides from an immobilized activated intermediate, wherein activation of the immobilized peptide is carried out with N-protecting group intact and subsequent removal leading to cyclization; McMurray et al (1994, *Peptide Research* 7:195–206, hereby incorporated by reference) which discloses head-to-tail cyclization of peptides attached to insoluble supports by means of the side chains of aspartic and glutamic acid; Hruby et al (1994, *Reactive Polymers* 22:231–241, hereby incorporated by reference) which teaches an alternate method for cyclizing peptides via solid supports; and Schmidt and Langer (1997, *J. Peptide Res.* 49:67–73, hereby incorporated by reference) which discloses a method for synthesizing cyclotetrapeptides and cyclopentapeptides. The foregoing methods may be used to produce conformationally constrained peptides with single stage competitive inhibition kinetics in respect of plasmin.

The invention also contemplates Textilinin polypeptides or biologically active fragments thereof that have been modified using ordinary molecular biological techniques so as to improve their resistance to proteolytic degradation or to optimize solubility properties or to render them more suitable as a therapeutic agent.

The present invention further encompasses chemical analogues of Textilinin polypeptides or biologically active fragments thereof, which analogues act as functional analogues of said polypeptides or fragments. In this regard, chemical analogues may not necessarily be derived from said polypeptides or fragments but may share certain conformational similarities. Alternatively, chemical analogues may be specifically designed to mimic certain physical properties of said polypeptides or fragments. Chemical analogues may be chemically synthesized or may be detected following, for example, natural product screening.

Textilinin polypeptides may be prepared by any suitable procedure known to those of skill in the art. For example, such polypeptides may be prepared by a procedure including the steps of:

(a) preparing a recombinant polynucleotide containing a nucleotide sequence encoding a Textilinin polypeptide, for example, SEQ ID NO:2, 4, 6, 8, 10, 12, 16, 18, 20, 22, 24 or 26, or biologically active fragment respectively thereof, or variant or derivative of these, which nucleotide sequence is operably linked to transcriptional and translational regulatory nucleic acid;

(b) introducing into a suitable host cell the recombinant polynucleotide;

(c) culturing the host cell to express recombinant polypeptide from said recombinant polynucleotide; and (d) isolating the recombinant polypeptide.

Suitably, said recombinant polynucleotide comprises an isolated natural Textilinin sequence. For example, such polynucleotide may be selected from any one of SEQ ID NO:1, 3, 5, 7, 9, 11, 15, 17, 19, 21, 23, 25 or 43.

The recombinant polynucleotide preferably comprises an expression vector that may be either a self-replicating extrachromosomal vector such as a plasmid, or a vector that integrates into a host genome.

The transcriptional and translational regulatory nucleic acid will generally be appropriate for the host cell used for expression. Numerous types of appropriate expression vectors and suitable regulatory sequences are known in the art for a variety of host cells.

Typically, the transcriptional and translational regulatory nucleic acid may include, but is not limited to, promoter sequences, leader or signal sequences, ribosomal binding sites, transcriptional start and stop sequences, translational start and stop sequences, and enhancer or activator sequences.

Constitutive or inducible promoters as known in the art are contemplated by the invention. The promoters may be either naturally occurring promoters, or hybrid promoters that combine elements of more than one promoter.

In a preferred embodiment, the expression vector contains a selectable marker gene to allow the selection of transformed host cells. Selection genes are well known in the art and will vary with the host cell used.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a nucleotide sequence according to the invention into the expression vector so that the translational reading frames of the fusion partner and the nucleotide sequence of the invention coincide.

Well known examples of fusion partners include, but are not limited to, glutathione-5-transferase (GST), Fc potion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such as fluorescence activated cell sorting (FACS) are particularly useful in this latter application.

Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-Myc, influenza virus, haemagglutinin and FLAG tags.

The step of introducing into the host cell the recombinant polynucleotide may be effected by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding a Textilinin polypeptide, fragment, variant or derivative according to the invention. The conditions appropriate for protein expression will vary with the choice of expression vector and the host cell. This is easily ascertained by one skilled in the art through routine experimentation.

Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, SF9 cells that may be utilised with a baculovirus expression system.

The recombinant protein may be conveniently prepared by a person skilled in the art using standard protocols as for example described in Sambrook, et al., MOLECULAR CLONING. A LABORATORY MANUAL (Cold Spring Harbor Press, 1989), incorporated herein by reference, in particular Sections 16 and 17; Ausubel et al., CURRENT PROTOCOLS IN MOLECULAR BIOLOGY (John Wiley & Sons, Inc. 1994–1998), incorporated herein by reference, in particular Chapters 10 and 16; and Coligan et al, CURRENT PROTOCOLS IN PROTEIN SCIENCE (John Wiley & Sons, Inc. 1995–1997) which is incorporated by reference herein, in particular Chapters 1, 5 and 6.

In some cases, the recombinant polypeptide may require refolding. Exemplary methods of refolding polypeptides include those as for example described by Bieri et al. (1995, *Biochemistry*, 34:13059–13065) and Norris et al, (1994, U.S. Pat. No. 5,373,090 to Novo Nordisk), which are incorporated herein by reference.

Alternatively, the Textilin polypeptides, polypeptide fragments, or variants or derivatives of these, may be synthesized using solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications.

3. Polynucleotides of the Invention 3.1. Textilinin Polynucleotides

The invention further provides a polynucleotide that encodes a Textilinin polypeptide, fragment, variant or derivative as defined above. Suitably said polynucleotide is selected from the group consisting of:—SEQ ID NO: 1, 3, 5, 7, 9, 11, 15, 17, 19, 21, 23, 25 and 43; a polynucleotide fragment of any one of SEQ ID NO: 1, 3, 5, 7, 9, 11, 15, 17, 19, 21, 23, 25 or 43; and a polynucleotide homologue of the foregoing sequences. Preferably, these sequences encode a product displaying single stage competitive inhibition of plasmin as defined above.

As will be more fully described hereinafter, a family of Textilinin (Txln) genes encoding single stage competitive inhibitors of plasmin has been obtained from *Pseudonaja textilis textilis*. SEQ ID NO:1 corresponds to a portion of the Txln 1 gene that encodes the mature Txln 1 polypeptide of about 7 kDa as defined in SEQ ID NO:2. SEQ ID NO:3 corresponds to a portion of the Txln 2 gene that encodes the mature Txln 2 polypeptide of about 7 kDa as defined in SEQ ID NO:4. SEQ ID NO:5, 7, 9 and 11, correspond respectively to portions of the Txln 3, Txln 4, Txln 5 and Txln 6 genes. These portions encode mature Txln 3, 4, 5 and 6 polypeptides, respectively.

The invention also provides full-length open reading frame (ORF) polynucleotides in relation to Txln 1, Txln 2, Txln 3, Txln 4, Txln 5 and Txln 6. Each said full-length polynucleotide comprises a first sequence encoding a 24-residue leader peptide, and a second sequence encoding a mature Txln polypeptide. The first sequence preferably comprises SEQ ID NO:15. SEQ ID NO:17, 19, 21, 23, and 25 correspond respectively to full-length ORF polynucleotides for Txln 1, Txln 2, Txln 3, Txln 4, Txln 5 and Txln 6. SEQ ID NO:43 corresponds to the largest cDNA sequence obtained for Txln 1, comprising 5' UTR and a 3'UTR sequences in addition to the ORF sequence.

Alternatively, a polynucleotide sequence encoding the Textilinin polypeptides or polypeptide fragments of the invention may be conveniently prepared by taking advantage of the genetic code and synthesising, for example, by use of an oligonucleotide sequencer, a sequence of nucleotides which when translated by a host cell results in the production of a polypeptide according to SEQ ID NO:2, 4, 6, 8, 10, 12, 16, 18, 20, 22, 24 or 26, polypeptide fragments thereof.

3.2 Polynucleotide Homologues

Suitable polynucleotide homologues of the invention may be prepared according to the following procedure:
 (i) obtaining a nucleic acid extract from a suitable host;
 (ii) creating primers which are optionally degenerate wherein each comprises a portion of a reference polynucleotide; and
 (iii) using said primers to amplify, via nucleic acid amplification techniques, at least one amplification product from said nucleic acid extract, wherein said amplification product corresponds to a polynucleotide homologue.

The host from which a nucleic acid extract is obtained is preferably a snake. Suitable snakes may be selected from the group consisting of the family Elapidae, and the family Viperae.

Suitably, the primers are selected from the group consisting of:—

(A) ATGAARGAYAGRCCHGARYTNGAR [SEQ ID NO:27];

(B) GTRCTYTCRTGYTCYTCY [SEQ ID NO:28];

(C) ATATATGGATCCAAGGACCGGCCTGACTTC [SEQ ID NO:29];

(D) AACGGGAATTCTCAGAGCCACACGTGCTTTC [SEQ ID NO:30];

(E) AACGGGAATTCTCATGAGCCACAGGTAGACTC [SEQ ID NO:31];

(F) CTAATACGACTCACTATAGGGCAAGCAGTGGTAACAACGCAGAG T [SEQ ID NO:32];

(G) CTAATACGACTCACTATAGGGC [SEQ ID NO:33];

(H) AAGCAGTGGTAACAACGCAGAGT [SEQ ID NO:34];

(I) ATCAGCGGATCCATGTCTGGAGGT [SEQ ID NO:35];

(J) TCTCCTGAATTCTCAGGCAGCACAGGT [SEQ ID NO:36];

(K) ATTATAGGATCCAAGGACCGTCCGGAT [SEQ ID NO:37];

(L) ATTATAGGATCCAAGGACCGTCCAGAG [SEQ ID NO:38];

(M) AACGTCGGATCCAAGGACCGTCCAAAT [SEQ ID NO:39];

(N) AACGTCGGATCCAAGGACCATCCAAAA [SEQ ID NO:40];

(O) AACGTCGGAT TCAAGGACCG TCCAAAA [SEQ ID NO:41];

(P) ATTGTCGGATCCAAGGACCTGCCAAAG [SEQ ID NO:42].

Alternatively, a polynucleotide homologue of the invention may be obtained from a polynucleotide library derived from a tissue of a snake. Such a library may be a snake cDNA library or snake genomic DNA library.

Suitable nucleic acid amplification techniques are well known to the skilled addressee, and include polymerase chain reaction (PCR) as for example described in Ausubel et al. (1994–1998, supra, Chapter 15) which is incorporated herein by reference; strand displacement amplification (SDA) as for example described in U.S. Pat. No. 5,422,252 which is incorporated herein by reference; rolling circle replication (RCR) as for example described in Liu et al., (1996, *J. Am. Chem. Soc.* 118:1587–1594 and International application WO 92/01813) and Lizardi et al., (International Application WO 97/19193) which are incorporated herein by reference; nucleic acid sequence-based amplification (NASBA) as for example described by Sooknanan et al., (1994, *Biotechniques* 17:1077–1080) which is incorporated herein by reference; and Q-β replicase amplification as for example described by Tyagi et at, (1996, *Proc. Natl. Acad. Sci. USA* 93:5395–5400) which is incorporated herein by reference.

Typically, polynucleotide homologues that are substantially complementary to a reference polynucleotide are identified by blotting techniques that include a step whereby nucleic acids are immobilized on a matrix (preferably a synthetic membrane such as nitrocellulose), followed by a hybridisation step, and a detection step. Southern blotting is used to identify a complementary DNA sequence; northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al. (1994–1998, supra) at pages 2.9.1 through 2.9.20.

According to such methods, Southern blotting involves separating DNA molecules according to size by gel electrophoresis, transferring the size-separated DNA to a synthetic membrane, and hybridising the membrane-bound DNA to a complementary nucleotide sequence labelled radioactively, enzymatically or fluorochromatically. In dot blotting and slot blotting, DNA samples are directly applied to a synthetic membrane prior to hybridisation as above.

An alternative blotting step is used when identifying complementary polynucleotides in a cDNA or genomic DNA library, such as through the process of plaque or colony hybridisation. A typical example of this procedure is described in Sambrook et al., (1989, supra) Chapters 8–12.

Typically, the following general procedure can be used to determine hybridisation conditions. Polynucleotides are blotted/transferred to a synthetic membrane, as described above. A reference polynucleotide such as a polynucleotide of the invention is labelled as described above, and the ability of this labelled polynucleotide to hybridise with an immobilised polynucleotide analyzed.

A skilled addressee will recognize that a number of factors influence hybridization. The specific activity of radioactively labelled polynucleotide sequence should typically be greater than or equal to about $10^8$ dpm/mg to provide a detectable signal. A radiolabelled nucleotide sequence of specific activity $10^8$ to $10^9$ dpm/mg can detect approximately 0.5 pg of DNA. It is well known in the art that sufficient DNA must be immobilized on the membrane to permit detection. It is desirable to have excess immobilized DNA, usually 10 μg. Adding an inert polymer such as 10% (w/v) dextran sulfate (MW 500,000) or polyethylene glycol 6000 during hybridization can also increase the sensitivity of hybridization (see Ausubel supra at 2.10.10).

To achieve meaningful results from hybridisation between a polynucleotide immobilized on a membrane and a labelled polynucleotide, a sufficient amount of the labelled polynucleotide must be hybridised to the immobilized polynucleotide following washing. Washing ensures that the labelled polynucleotide is hybridized only to the immobilized polynucleotide with a desired degree of complementarity to the labelled polynucleotide.

It will be understood that polynucleotide homologues according to the invention will hybridise to a reference polynucleotide under stringent conditions. Typical stringent conditions include, for example, (1) 0.75 M dibasic sodium phosphate/0.5 M monobasic sodium phosphate/1 mM disodium EDTA/1% sarkosyl at about 42° C. for at least 30 minutes; or (2) 6.0 M urea/0.4% sodium lauryl sulfate/0.1× SSC at about 42° C. for at least 30 minutes; or (3) 0.1× SSC/0.1% SDS at about 68° C. for at least 20 minutes; or (4) 1×SSC/0.1% SDS at about 55° C. for about 60 minutes; or (5) 1×SSC/0.1% SDS at about 62° C. for about 60 minutes; or (6) 1×SSC/0.1% SDS at about 68° C. for about 60 minutes; or (7) 0.2×SSC/0.1% SDS at about 55° C. for about 60 minutes; or (8) 0.2×SSC/0.1% SDS at about 62° C. for about one hour; or (9) 0.2×SSC/0.1% SDS at about 68° C. for about 60 minutes. For a detailed example, see CURRENT PROTOCOLS IN MOLECULAR BIOLOGY supra at pages 2.10.1 to 2.10.16, and Sambrook et al. in MOLECULAR CLONING. A LABORATORY MANUAL (Cold Spring Harbour Press, 1989) at sections 1.101 to 1.104, which are hereby incorporated by reference.

While stringent washes are typically carried out at temperatures from about 42° C. to 68° C., one skilled in the art will appreciate that other temperatures may be suitable for stringent conditions. Maximum hybridisation typically occurs at about 20° C. to 25° C. below the $T_m$ for formation of a DNA—DNA hybrid. It is well known in the art that the $T_m$ is the melting temperature, or temperature at which two complementary polynucleotide sequences dissociate. Methods for estimating $T_m$ are well known in the art (see CURRENT PROTOCOLS IN MOLECULAR BIOLOGY supra at page 2.10.8). Maximum hybridization typically occurs at about 110° C. to 15° C. below the $T_m$ for a DNA-RNA hybrid.

Other stringent conditions are well known in the art. A skilled addressee will recognize that various factors can be manipulated to optimize the specificity of the hybridization. Optimization of the stringency of the final washes can serve to ensure a high degree of hybridisation.

Methods for detecting a labelled polynucleotide hybridised to an immobilised polynucleotide are well known to practitioners in the art. Such methods include autoradiography, chemiluminescent, fluorescent and calorimetric detection.

4. Vectors

A polynucleotide according to the invention is suitably rendered expressible in a host cell by operably linking the polynucleotide with one or more regulatory nucleic acids. The synthetic construct or vector thus produced may be introduced firstly into an organism or part thereof before subsequent expression of the construct in a particular cell or tissue type. Any suitable organism is contemplated by the invention that may include unicellular as well as multicellular organisms. Suitable unicellular organisms include bacteria. Exemplary multi-cellular organisms include yeast, mammals and plants.

The construction of the vector may be effected by any suitable technique as for example described in the relevant sections of Ausubel et al. (supra) and Sambrook et al. (supra). However, it should be noted that the present invention is not dependent on and not directed to any one particular technique for constructing the vector.

Regulatory nucleotide sequences which may be utilised to regulate expression of the polynucleotide include, but are not limited to, a promoter, an enhancer, and a transcriptional terminator. Such regulatory sequences are well known to those of skill in the art. Suitable promoters that may be utilised to induce expression of the polynucleotides of the invention include constitutive promoters and inducible promoters.

5. Therapeutic Agents

A further feature of the invention is the use of the polypeptide, fragment, variant or derivative of the invention ("therapeutic agents") as actives in a pharmaceutical composition for alleviating patients against blood loss. Suitably, the pharmaceutical composition comprises a pharmaceutically acceptable carrier.

By "pharmaceutically-acceptable carrier" is meant a solid or liquid filler, diluent or encapsulating substance that may be safely used in systemic administration. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Any suitable route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Preferably, an intravenous route is employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be administered in a manner compatible with the dosage formulation, and in such amount as is therapeutically effective to alleviate patients from blood loss. The dose administered to a patient, in the context of the present invention, should be sufficient to effect a beneficial response in a patient over time such as a reduction or cessation of blood loss. The quantity of the therapeutic agent(s) to be administered may depend on the subject to be treated inclusive of the age, sex, weight and general health condition thereof. In this regard, precise amounts of the therapeutic agent(s) for administration will depend on the judgement of the practitioner. In determining the effective amount of the therapeutic agent to be administered in the treatment of blood loss, the physician may evaluate the progression of blood loss over time. In any event, those of skill in the art may readily determine suitable dosages of the therapeutic agents of the invention. Such dosages may be in the order of nanograms to milligrams of the therapeutic.

6. Anti-Tumour Agent

The invention also extends to an anti-tumour agent comprising a polypeptide, polypeptide fragment, variant of derivative according to the invention conjugated with an anti-fibrin antibody. Such a conjugate may be to thereby inhibit progression and invasiveness of such tumours. Reference may be made in this regard to an abstract by Raut and Gaffney (1996, *Fibrinolysis* 10 (Suppl. 4):1–26, Abstract No 39) which is hereby incorporated by reference.

The anti-fibrin antibodies may include any suitable antibodies that bind to or conjugate with fibrin, preferably human fibrin. For example, the anti-fibrin antibodies may comprise polyclonal antibodies. Such antibodies may be prepared for example by injecting fibrin into a production species, which may include mice or rabbits, to obtain polyclonal antisera.

In lieu of the anti-fibrin polyclonal antisera obtained in the production species, monoclonal antibodies may be produced using the standard method as for example, described in an article by Köhler and Milstein (1975, *Nature* 256:495–497) which is hereby incorporated by reference, or by more recent modifications thereof as for example, described in "CURRENT PROTOCOLS IN IMMUNOLOGY" (1994, Ed. J. E. Coligan, A. M. Kruisbeek, D. H. Marguiles, E. M. Shevach and W. Strober, John Wiley and Son Inc. which is hereby incorporated by reference) by immortalising spleen or other antibody producing cells derived from a production species which has been inoculated with fibrin.

Preferred monoclonal antibodies which may be used to produce the anti-tumour agent of the invention include, but are not limited to, the anti-fibrin monoclonal antibodies disclosed by Tymkewycz et al (1993, *Blood Coagul. Fibrinol.* 4:211–221) which is hereby incorporated by reference or the monoclonal antibody described by Raut and Gaffney (1996, supra).

Also contemplated are anti-fibrin antibodies which comprise Fc or Fab fragments of the polyclonal or monoclonal antibodies referred to above. Alternatively, the anti-fibrin antibodies may comprise single chain Fv antibodies (scFvs) against fibrin. Such scFvs may be prepared, for example, in accordance with the methods described respectively in U.S. Pat. No. 5,091,513, European Patent No 239,400 or the article by Winter and Milstein (1991, *Nature* 349:293) which are hereby incorporated by reference.

Any suitable procedure may be used to conjugate the anti-fibrin antibodies with a polypeptide, polypeptide fragment, variant or derivative according to the invention. For example, reference may be made to the 'zero-length' cross linking procedure of Grabarek and Gergely (1990, *Anal. Biochem.* 185:131–135), which is incorporated herein by reference.

In order that the invention may be readily understood and put into practical effect, particular preferred embodiments will now be described by way of the following non-limiting examples.

EXAMPLES

Example 1

Characterization of Two Plasmin Inhibitors from *Pseudonaja Textilis Textilis* which Inhibit Bleeding in an Animal Model Materials and Methods Materials Pooled lyophilised *P textilis* venom was obtained from Mr Peter Mirtschin, Venom Supplies, Tanunda, South Australia. Venom was reconstituted in 0.05 M tris-HCl buffer pH 7.4, at 10 mg/ml and the solution was centrifuged (2,000 g for 30 min) before chromatography or analysis. Sephacryl S-300, Sephacryl S-100, con A-Sepharose and DEAE-Sepharose CL-6B were obtained from Pharmacia Uppsala, Sweden, and the synthetic chromogenic substrate S-2251 was from Chromogenix, Mölndal, Sweden. A highly purified plasmin from Sanofi/Choay Laboratories (Paris) was used for some kinetic experiments. All other buffers and reagents were Analar grade.

Preparation of Plasminogen and Plasmin

Human plasminogen was purified from outdated pooled citrated plasma using the affinity chromatography procedure described elsewhere (Deutsch and Mertz. 1970, *Science* 170:1095). Human plasmin was prepared from plasminogen by activation with urokinase-bound Sepharose 4B (Robbins, K C., 1978 "Plasmin" In: Handbook of experimental pharmacology. Markwardt F, ed. Berlin: Springer 46: 317,) and calibrated against the International Standard for plasmin (77/558).

Plasmin Inhibitory Assay

The plasmin inhibitory assay was carried out essentially as described elsewhere (Friberger et al. 1978., Haemostasis 7:138). 900 µL of 0.15 M tris-HCl, pH 7.4, 25 µL (0.1 IU) of plasmin, 25 µL of inhibitor were added to 50 µL of substrate S-2251 (3.0 mM) and the residual plasmin was determined by continuous measurement of the absorbance of 405 nm in a Hitachi 557 recording spectrophotometer. A standard curve of plasmin activity was prepared using the International Standard (77/558).

Purification of Txln 1 and 2

We here describe for the first time purification procedures which allowed the isolation of two distinct forms of the Txln inhibitor. A Sephacryl S-300 column (5.0×95 cm) was equilibrated at 4° C. with 0.1 M ammonium acetate buffer (pH 7.0) at a flow rate of 1 mL per minute. 500 mg of lyophilised *P. texilis* venom was reconstituted in 25 mL of column buffer, and following centrifugation at 10,000 rpm for 20 minutes, was applied to the column. 12 mL fractions were collected using an LKB fraction collector, and the eluate was monitored at 280 nm using an Altex dual wavelength in line UV detector. The pooled plasmin inhibitor fractions were concentrated using an Amicon stirred cell concentrator Model 402 with a YM 3 membrane and this concentrate was applied to the DEAE-Sepharose column. The DEAE-Sepharose column (2.5×12 cm) was equilibrated at 4° C. with 0.05 M phosphate buffer (pH 8.0) at a flow rate of 1.0 mL per minute. Following the application of the concentrated plasmin inhibitor, the column was washed with buffer giving a non-bound protein peak with no plasmin inhibitory activity. A linear gradient of NaCl (0–0.5 M, 500 mL) was applied at a flow rate of 1.0 mL per minute in order to separate the two forms of Txln. The pooled plasmin inhibitors 1 and 2 (concentrated in the Amicon cell) were individually further purified on a Sephacryl™ S-100 column (2.5×95 cm) which was equilibrated with 0.05 M Tris-HCl, (pH 7.4). Fractions with the highest plasmin inhibitory activity were pooled, concentrated and stored at concentrations of about 1 mg/mL ($\square$143 µM) in Tris buffered saline. Finally a trace contaminant was removed from Txln 1 and Txln 2 samples by application to a column of Con A-Sepharose (1×10 cm) equilibrated with 0.15 M Tris-HCl buffer (pH 7.4). The pooled and concentrated plasmin inhibitors were applied to this column at a flow rate of 1.0 mL per minute and the inhibitory activity was found in the wash peak.

The purity of Txln preparations was checked by reverse phase (RP) HPLC on a Waters $C_{18}$ µbond pack column (0.6×30 cm) equilibrated with 0.05% trifluoroacetic acid (TFA) in water and developed using a 0 to 70% acetonitrile gradient in 0.05% TFA. The chromatography was monitored at 214 nm and the gradient was developed over 60 minutes. Further check on purity was performed using Sodium Dodecyl Sulphate (SDS)-Polyacrylamide Electrophoresis (PAGE) (Weber and Osborn, 1969. *J. Biol. Chem.* 244:4406) while the samples were prepared by a method which incorporates 4 M urea in the sample solution (Gaffney and Dobos, 1971, *FEBS Lett.* 15:13).

Amino Acid Sequencing:

Reduction and carboxymethylation of Txln 1 and 2 were performed in 6 M guanidine hydrochloride, 0.1 M Tris-HCL buffer, 1 mM EDTA, (pH 9.5) with 10 mM dithiothreitol (DTT) for 2 hours under Argon at 37° C. The carboxymethylation (CM) step was performed with 15 mM iodoacetic acid for 30 minutes. The CM Txln 1 and 2 were digested with endoproteinase Lys C and endoproteinase Asp N respectively in 50 mM phosphate buffer, pH 8.0 at 37° C. for 18 hours, using an enzyme to substrate ratio of (1:100). The reactions were stopped by acidification with TFA and the digests were fractionated by RP-HPLC on a Vydac $C_8$ column (2.1×150 mm) using a Hewlett Packard 1090 liquid chromatograph equipped with a diode-array detector. At a flow rate of 0.2 mL/min linear gradiants were formed between 0.1% TFA in water and 0.1% TFA in 70% acetonitrile. All chromatographies were carried out at room temperature. Amino acid sequence determinations were carried out on a Hewlett Packard G10005A sequencer by first carrying out a long N-terminal sequencing of both Txln 1 and 2. The C-terminal sequences for Txln 1 and 2 were derived from the C-terminal fragment obtained from endoLys C and endoproteinase Asp N digestions. The evidence for the sequence is derived from a long N-terminal sequence run of the whole molecule, an extended sequence of an endoLys C peptide obtained by further chromatography of one of the peptides isolated by reverse-phase chromatography and the sequence of an endoproteinase Asp N peptide. The C-terminal two amino acids were identified from the full-length c-DNA sequence obtained during the cloning and expression of textilinin in *E. coli* (as hereinafter described in EXAMPLE 2).

Mass Spectrometry

Matrix-assisted laser desorption/ionization (MALDI) time-of-flight (TOF) mass spectrometry was performed with a Bruker Reflex mass spectrometer (Bruker-Franzen Analytik GMBH, Breman, Germany) operated exclusively in the reflectron mode. Samples were diluted in 30% aqueous acetonitrile containing 0.1% trifluoroacetic acid and 2 mL of a matrix comprised of 2,6-dihydroacetophenone containing diammonium hydrogen citrate prior to deposition of 0.5–1 mL onto a stainless steel target.

Mouse Tail Vein Bleeding Model

A bleeding model was established using mature outbred Quackenbush mice (average 20 gram) of both sexes after anaesthesia was induced by intra peritoneal injection of 0.4 mL of a one in ten dilution of an equal volume mixture of Ketamine (100 mg/mL) and Rompun (xylazine, 40 mg/mL). Tail vein intravenuous delivery of aprotinin, the two txlns (100 µg/100 µL of saline for each substance) was performed after anaesthesia was established and tail excision was performed 2 minute later for each mouse. The dose of the plasmin inhibitors used in these experiments were similar to that used during human CPB surgery adjusted to the mouse weight of 20 grams. Blood loss was measured by collection into preweighed eppendorf tubes. Accuracy dictated that blood loss was measured by weight rather than volume. All mice were euthanized by cervical dislocation. All mice experiments were approved by the Ethics Committee of the Princess Alexandra Hospital. This Committee did not encourage a dose-response study and the inventors consider that an adjusted dose used in human surgery was a realistic basis for these initial studies. Such a dose of the Txlns was observed not to induce any adverse effects on the mice when observed over a period of 2 days.

Kinetics of Plasmin Inhibition

Procedures for investigation of plasmin inhibition kinetics by the two purified textilinins (Txln 1 and Txln 2) were in accordance with that described elsewhere (Stone et al., 1984, *Biochim. Pharmacol* 33:175) and differed from the method used to study the impure Txln preparation (Willmott et al., 1995, supra) in that 4-fold and 36-fold higher enzyme concentrations were used. This latter approach allowed truncation of time scale from one hour to ten minutes or less. Enzyme-inhibitor assays were performed at 25° C. in 0.1 M Tris/HCl, pH 7.4, containing 0.01% (v/v) Tween 80. A concentration of either 2 nM or 18 nM plasmin was used in these experiments with 75 µM chromogenic substrate (S-2251) and 16–410 nM Txln. On the grounds that the pattern of plasmin inhibition was of the form associated with slow tight-binding inhibition, the progress curves were analysed in terms of the relationship:—

$$[P]=v_s t+(v_s-v_o)\{1-\exp(-kt)\}/k \qquad \text{(Eq. 1)}$$

which describes the time dependence of the concentration of chromogenic product [P] as a function of the initial ($v_o$) and ultimately attained ($v_s$) velocities and the apparent rate constant (k) for the transition between the initial and final (steady) states. For the present system the initial rate in experiments conducted with a fixed concentration of chromogenic substrate [S] exhibited no dependence upon inhibitor concentration [I]—a simplifying circumstance that allowed $v_o$ to be identified as the initial velocity in the absence of plasmin inhibitor (see equation 2). Under those conditions the rate constant (k) may be expressed in terms of the competitive inhibitor constant ($K_1$) and the Michaelis constant for chromogenic substrate ($K_m$) as $$k=k_d[1+[I]/\{K_I(1+[S]/K_m)\}] \quad (Eq.\ 2)$$

where $k_d$ is the rate constant for dissociation of the plasmin-inhibitor complex (Stone et al., 1984, supra). Since the steady-state velocity, $v_s$, may be expressed in terms of the maximal velocity V and the relationship for classical competitive inhibition, namely, $$v_s=V[S]/\{[S]+K_m(1+[I]/K_1\} \quad (Eq.\ 3)$$

the inhibitor constant $K_I$ and the dissociation rate constant $k_d$ were the two curve-fitting parameters to emanate from global analysis of the progress curves.

Results

Purification Data

FIG. 1(a) shows the Sephacryl S-300 chromatographic separation of proteins from the crude venom showing three major and two minor peaks of protein, labelled 1–5. Plasmin inhibitory activity is indicated in the right-hand shoulder of peak four (see shaded area), using the plasmin neutralisation assay to monitor the eluted fractions. Further fractionation of the pooled inhibitor fractions, (Amicon YM3 concentrated), was performed on a DEAE-Sepharose CL-6B column. FIG. 1(b) shows the resultant separation, indicating two distinct peaks of plasmin inhibitory activity, marked by solid horizontal bars and labelled 1 and 2. Each peak was pooled separately, concentrated and applied to a Sephacryl S-100 column to remove trace impurities. FIG. 2 shows the elution profile of Txln 1, which is identical to that of Txln 2, however the insert in FIG. 2 shows the reverse-phase HPLC profiles of each Txln indicating each to have a distinct elution volume from this column. The purity of the Sephacryl S-100 eluted material was further demonstrated by SDS-PAGE gel electrophoresis (data not shown). The final concentrated plasmin inhibitors were stored at −20° C. in 0.05 M Tris buffered saline at a final concentration of about 1 mg/mL.

While these preparations were adequate for kinetic and physical characterisation, it was noted that both Txln 1 and 2 caused distress in the mouse model used to assess blood loss. For such experiments it was necessary to remove trace amount of a potent prothrombin activator complex using a Con A-Sepharose column as described elsewhere (Masci PP. 1986. *The effects of Australian snake venoms on coagulation and fibrinolysis*. Masters Thesis; University of Queensland).

Primary Sequence

Figure 3:
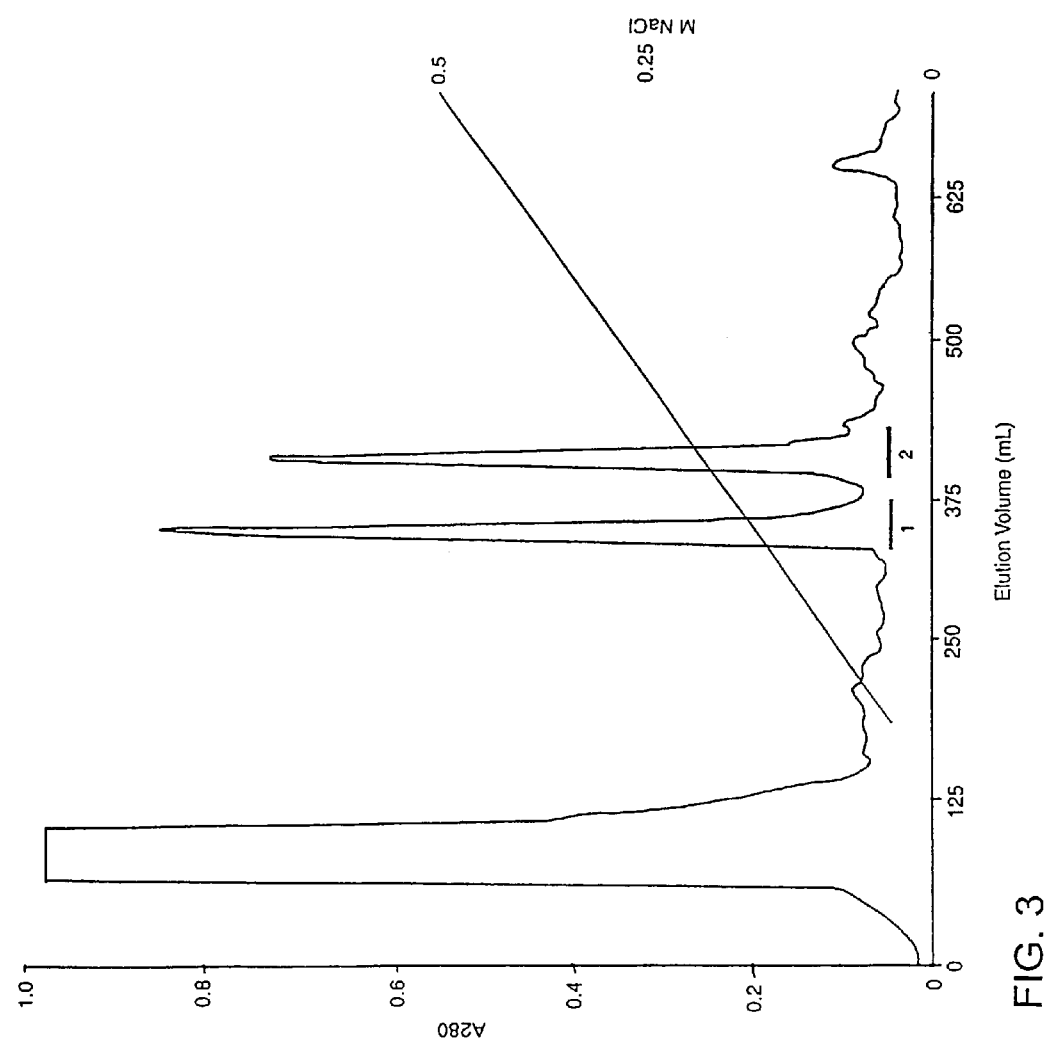
FIG. 3 shows a Sephacryl™ S-100 elution profile of one of the two pooled and concentrated fractions obtained from the DEAE-Sepharose™ CL-6B chromatography. The profile shown is that of Txln 1 but the profile of Txln 2 is identical. Insert, however shows two distinct elution profiles for each of Txln 1 and Txln 2 using reverse-phase C 18 BPLC chromatography.

FIG. 3 shows the amino acid sequences of Txln 1 and 2 with those of aprotinin and Taicotoxin-associated plasmin inhibitor isolated from the venom of the Australian Eastern Taipan, *Oxyuranus scutellatus* (having the closest homology to Txln 1 and 2) for comparison. It can be seen that all four plasmin inhibitors have the cysteine arrangements that are typical of this group of plasmin inhibitors and endow them with great stability. It was found that Txln 1 and 2 could be heated at 80° C. for two hours with no loss of inhibitory activity (unpublished data). A sequence difference of six amino acids was observed between Txln 1 and 2, while each showed, respectively, 45 and 43% homology with aprotinin. There was 58% and 55% homology, respectively, between Txln 1 and 2 and the Taicotoxin associated plasmin inhibitor. Both Txlns are quite acidic proteins with nett negative charges of −4 (Txln 1) and −6 (Txln 2), while aprotinin is quite basic, having a nett charge of +6. Mass spectroscopy data for Txln 1 and 2 showed molecular weights of 6682.4 and 6689.3 (data not shown), which agreed quite well with the molecular weights from the amino acid compositions.

Kinetic Data

Figure 4:
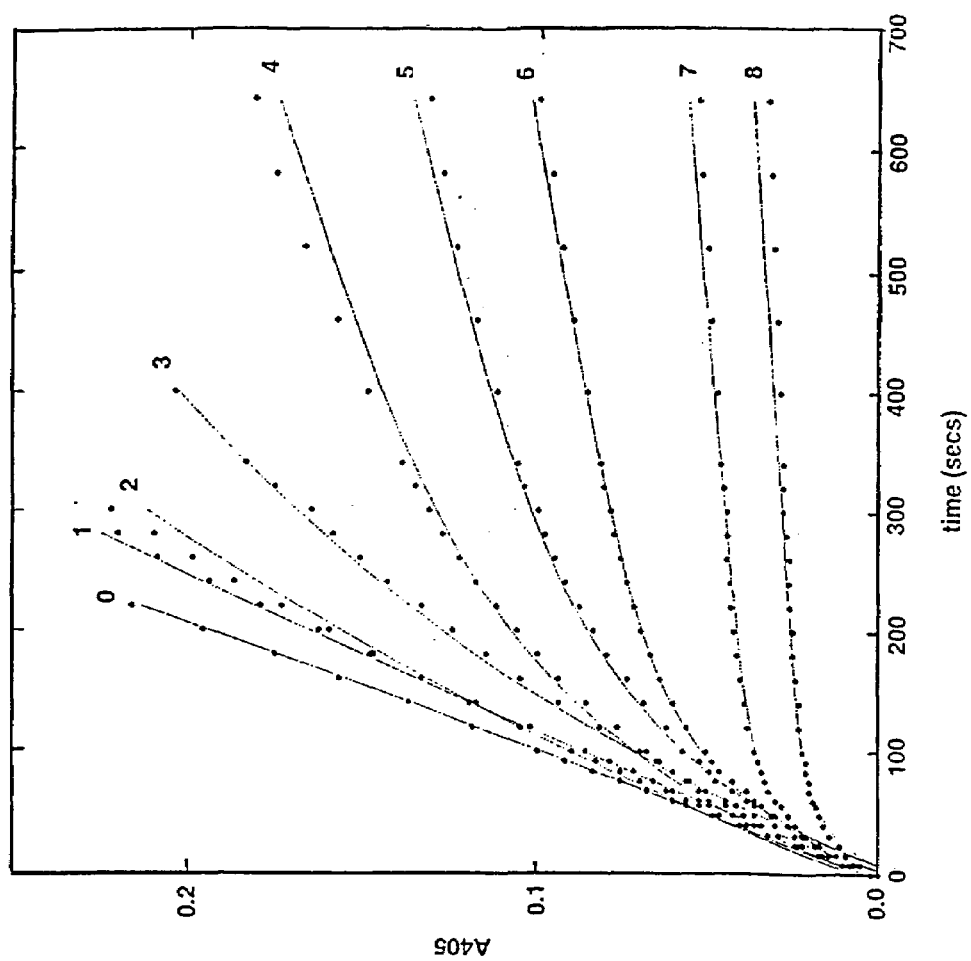
FIG. 4 illustartes a real time curve fit analysis using Sigmaplot of Txln 1 (0–410 nM) inhibiton of plasmin (2 nM). Similar inhibition curves (data not shown) were obtained with Txln 2.

FIG. 4 presents progress curves for chromogenic substrate hydrolysis by 2 nM plasmin in the presence of 0–410 nM Txln 1. These data resemble more closely those reported for aprotinin (Willmott et al., 1995, supra); our prior data with impure Txln did suggest simple competitive inhibition, wheras these latter data with purified Txln 1 and 2 resemble more the two-step mechanism of aprotinin. The inhibitor constant ($K_I$) deduced from those data by global analysis in terms of Equations 1–3 is presented in Table 3, together with corresponding values for Txln 2 and the mixture of textilinins that co-chromatographed prior to DEAE-Sepharose chromatography.

TABLE 3

| | Plasmin Concentration | |
|---|---|---|
| | 2 nM (n = 6) Mean ± SD | 18 nM (n = 6) Mean ± SD |
| Sephacryl 100 Pool (Txln 1 and 2) | $7.1 \times 10^{-9} \pm 0.2$ | $13.9 \times 10^{-9} \pm 0.3$ |
| Txln 1 | $3.5 \times 10^{-9} \pm 3$ | $2.6 \times 10^{-9} \pm 0.2$ |
| Txln 2 | $2.2 \times 10^{-9} \pm 0.2$ | $2.8 \times 10^{-9} \pm 0.3$ |
| Aprotinin* | $5.3 \times 10^{-11}$ | |

Corresponding results from progress curves for experiments with a higher plasmin concentration (18 nM) are also summarised in Table 3. Comparison of the inhibitor constants for the isolated Txlns 1 and 2, which are indistinguishable from each other, with that for the partially purified preparation suggests that a 3- to 5-fold protein purification has been achieved by the ion-exchange and extra Sephacryl S-100 chromatography steps. The inhibitor constants shown in Table 3 are much smaller than the value of 150 µM reported previously (Willmott et al., 1995, supra) for the impure Txln preparation. The increased strength of Txln-plasmin binding observed in this present study presumably reflects the removal of unidentified compound(s) from the Txln during the later stages of the present more extensive purification procedure. Despite this, the Ki values of the pure Txlns for plasmin are about 100-fold less than that observed for aprotinin (Willmott et al., 1995, supra).

Behaviour of Txlns in an Animal Bleeding Model

Since Txln inhibition of plasmin activity is much weaker (100-fold, see Table 3) than that observed for aprotinin, an animal model has been used to establish the effectiveness of the Txln in stemming blood loss when it is used at the same dosage as aprotinin.

The effect of intravenous delivery of (tail vein) Txln 1 and 2 on the blood-loss from an excised mouse tail vein is shown in Table 4 and for comparison the results for aprotinin are also shown.

TABLE 4

| | Blood weight (gms) (N = 24) Mean ± SD | Average reduction in blood loss (%) |
|---|---|---|
| Control (Saline) | 0.869 ± 0.245 | — |
| Aprotinin (100 µg) | 0.352 ± 0.152 | 59.5 |
| Txln 1 (100 µg) | 0.386 ± 0.250 | 55.6 |
| Txln 2 (100 µg) | 0.329 ± 0.234 | 62.2 |

The amount used was equivalent on a weight basis to the amount of aprotinin used clinically in humans and this was 100 µg of each substance studied per average 20 gram mouse. It can be seen from Table 4 that aprotinin reduced blood loss by 60% while both Txlns reduced blood loss to a similar extent when compared with saline-injected controls. The validity of these comparisons may need further scrutiny as the amounts of the Txlns and aprotinin used in the animal model were based on plasmin neutralization in vitro and may be subject to some error. Molar comparison of amounts of these inhibitors to be used in future experiments may be more appropriate.

DISCUSSION

Reduction in blood flow during major surgery or following trauma is of current concern because of a deteriorating blood donor status. The increased incidence of viral contamination of blood has introduced socio-medical problems that do not seem to abate. There is anxiety concerning the contamination of blood by HIV, hepatitis B and C viruses, while the potential for cross-contamination by prions associated with Bovine Spongiform Encephalitis (BSE) and Creutzfeldt-Jakob Disease (CJD) remains a major cloud over the whole blood transfusion area.

Aprotinin derived from bovine lung is used for the stemming of blood flow during surgical procedures such as cardio-pulmonary bypass (CPB) (Royston D. 1990. *Blood Coagul. Fibrinol.* 1:53; Royston D. 1992. *J. Cardiothorac. Vasc. Anesh.* 6:76,). Indeed, while CPB is the major surgical circumstance in which aprotinin is used, blood loss during neurosurgery (Gurdetti and Spallone. 1981. *Surg. Neurol.* 15:239), orthopaedic (Ketterl et al., 1982. *Medizinische Welt* 33:480), liver (Neuhaus et al. 1989 *Lancet* ii:924) and urological (Kosters and Wand. 1973. *Urologe* 12:295) surgeries have been reduced using this drug. This widespread usage is despite some reports of thrombosis (Van der Meer et al., 1996. *Thromb. Haemost.* 75:1; Cosgrove et al., 1992. *Ann. Thorac. Surg.* 54:1031; Samama et al., 1994 *Thromb. Haemost.* 71:663) and fatal anaphylaxis during cardiac surgery (Diefenbach et al., 1995. *Anesth. Analg.* 80:830). While the exact mechanism of action of aprotinin is not known it is now accepted that plasmin inhibition is central to its capacity to reduce blood loss (Royston D. 1990., supra; Orchard et al., 1993. *Br. J. Haematol.* 85:596). However, aprotinin has other effects on the coagulation cascade and on platelet function (Westaby, S. 1993. *Ann. Thorac. Surg.* 55:1033). The GPIIb/IIIa receptors which are mostly responsible for platelet adhesion are not affected by contact with bypass circuit surfaces whereas plasmin degrades the platelet GPIb receptor which can reduce the ability of platelets to form haemostatic plugs (Wenger et al., 1989. *J. Thorac. Cardiovasc. Surg.* 97:235). Thus plasmin inhibition may also affect this latter platelet mechanism enhancing the stability of the haemostatic plug. It is worth while here to indicate that aprotinin has been found to inhibit protein C (Cooper B E. 1995. *J. Pharm. Technol.* 11:156), which in turn would result in reduction in thrombin production and enhanced fibrinolysis (Gaffney P J, Edgell T A. Fibrinolysis and the haemostatic balance. "Harmonisation of some old and new concepts." In: Recent progress in blood coagulation and fibrinolysis. Takada A, Collen D, Gaffney P J, Eds. Amsterdam; Elsevier Science BV 127, 1997).

Both these latter effects could reduce the effectiveness of aprotinins in reducing blood loss. While the lack of specificity of aprotinin leads to confusion about its mechanism of action the inhibition of plasmin still seems to be central to its effectiveness. The reduction in the formation of the fibrin fragment D dimer in aprotinin-treated patients has been the main evidence (Orchard et al., 1993, supra; Ray and Marsh. 1997. *Thromb. Haemost.* 78:1021; Dietrich et al., 1990. *Anesthesiology* 73:1119) that plasmin inhibition is central to its mechanism; however it has been argued (Dietrich et al., 1990, supra) that inhibition of fibrin formation and thus reduction in fibrin-mediated activation of plasminogen to plasmin could also offer an explanation for the reduction in D dimer levels.

In order to provide other alternative haemostatics based on plasmin inhibition, snake venoms have been studied for some years. The first report of a plasmin/trypsin inhibitor found in snake venom was by Takahashi et al 1972. *FEBS Lett.* 27:207), while there are further reports of plasmin inhibitors in other viper and elapid venoms (Shafqut et al., 1990. *Eur. J. Biochem.* 194 (2):337; Shajqut et al., 1990. *FEBS Lett.* 275:6; Yamakawa et al., 1987. *Biochim. Biophys. Acta* 925:124; Ritonja et al, 1983. *Eur. J. Biochem.* 133: 427; Strydom et al., 1979. *Biochim. Biophys. Acta* 491:361). Screening of Australian elapid venoms has shown that two snake genera possess potent plasmin inhibitors (Masci P P. Masters Thesis 1986, supra). These are the *Pseudonaja* and *Oxyuranus* genera. In the *Pseudonaja* genus, the venom from all species was shown to possess an inhibitor of plasmin. This inhibitor has been partially purified and kinetically characterised from the *textilis* subspecies (Wilmott et al., 1995, supra) and has been subsequently named Textilinin (Txln). Further purification (FIGS. 1 and 2) has shown that there are two forms of this inhibitor, Txln 1 and 2. In the *Oxyuranus* genus, the venom of only one species was shown to contain a plasmin/trypsin inhibitor which has been sequenced and shown it to be associated in a multimeric complex (Possani et al., 1992. *Toxicon.* 30:1343). This complex was demonstrated to be a calcium channel blocker containing an alpha neurotoxin, a phospholipase and the trypsin inhibitor called Taicotoxin. FIG. 3 shows that this trypsin inhibitor (TAC) has 58 and 55% homology with Txln 1 and 2, respectively, and this is the closest homology to the Textilinins of the known naturally occurring plasmin inhibitors. There is only 45 and 43% homology between Txln 1 and 2, respectively, and aprotinin. There are 6 amino acids difference between Txlns 1 and 2, and both are acidic, containing nett negative charges (−4 and −6 respectively), as distinct from aprotinin which is a basic molecule (+6).

While studying the kinetics of a partially purified plasmin inhibitor preparation from the *P. texilis* venom, it had been observed (Wilmott et al., 1995, supra) that this inhibitor bound rapidly and more specifically to plasmin than did aprotinin (Fritz and Wanderer. 1983. *Drug Res.* 4:479). The results also showed that textilinin bound less tightly to plasmin than did aprotinin. The specificity of aprotinin was shown to be broad based, neutralizing tPA, urokinase and lo kallikrein, as well as plasmin and trypsin (Fritz and Wanderer. 1983, supra) while studies of the snake venom plasmin inhibitor, Txln, have shown it to bind more specifically to plasmin and trypsin in a rapid single step reaction which seems to be reversible (Wilmott et al, 1995, supra). Since aprotinin has been reported (Van der Meer et al., 1996, supra; Cosgrove et al., 1992, supra; Samama et al., 1994., supra.) to be associated with increased incidence of vein-graft occlusion and thrombosis, it was surmised that a less-tight binding inhibitor such as Txln may be of greater clinical efficacy. This original finding had prompted us to further purify the Txln from the venom and it was then found that each snake venom contained two forms of the Txln, which reflects the work of other workers (Takahashi et al, 1974. *Toxicon.* 12:193) who also reported two variants of a Russell's viper venom plasmin inhibitor. Both Txlns bound to plasmin less tightly than aprotinin, but more strongly than has been indicated with partially purified material reported previously (Wilmott et al., 1995, supra).

Txlns 1 and 2 reduce blood loss in a mouse tail-vein-bleeding model (Table 4) as effectively as aprotinin. If the reduction in blood loss in this model is associated with plasmin neutralisation at the site of the haemostatic plug formation as suggested (Royston D., 1992, supra), it is not surprising that they compare favourably. The inability of Txln to neutralise kallikrein in contrast to aprotinin (our unpublished data) may have some clinical significance. This, of course, depends on the contribution of the kallikrein-Factor XII pathway on the production of plasmin at the site of wound healing (Kluft et al., 1987. *Sem. Thromb. Haemost.* 13:50). Indeed, the kallikrein inhibitory effect of aprotinin could be a contributing factor to either a prothrombotic or prohaemorrhagic effect for this drug; the general opinion is that aprotinin inhibition of the extrinsic coagulation pathway via kallikrein-Factor XII would tend to inhibit coagulation following passage of blood through CPB machines (Westaby S., 1993, supra).

What role the Txln molecule plays in the human coagulation imbalance associated with this snake bite is unclear since envenomation is accompanied by a dramatically increased fibrinolytic activity which is, in turn, related to the disseminated intravascular coagulation in the bitten individual (Masci et al., 1990. *Thrombosis Research* 59:859; Tibballs et al., 1992. *Anesthesia and Intensive Care* 20:28). Presumably this fibrinolytic activity is stimulated by the prothrombin-mediated fibrin complex (Gaffney and Edgel, 1997, supra). That the subsequent inhibition of fibrinolysis might contribute to this fibrin-mediated occlusion of the microvasculature is plausible.

Currently it is the kinetic profile and the narrow specificity of the Txlns that suggest strongly that there may be a clinical benefit over aprotinin to reduce blood loss. There is no doubt that the mouse bleeding model data indicate comparative blood loss reductions, but there are no physiological data suggesting that Txln may have less deleterious side effects than aprotinin. However, all mice treated with Txln showed no side effects. Notwithstanding this lack of evidence, the fact that repeated therapeutic use of aprotinin is contra-indicated (Wüthrich et al., 1992 *Lancet* 340:173) is sufficient to justify the cloning and expression of these new haemorrhagic inhibitors.

Example 2

Cloning and Sequencing of Textilinin cDNA

Materials and Methods

Materials

Common Brown Snake venom glands were obtained from reptiles deemed to be destroyed, having clinical conditions, which could not be treated. Venom glands were surgically taken, under sterile conditions, immediately after the animals were euthanized by a lethal dose of pentobarbitone (60 mg/Kg). Department of Environment and Heritage as well as the University of Queensland Animal Ethics committee approved the termination of these reptiles. Two excised venom glands (approximately 100 mg of wet tissue) were immediately frozen in liquid nitrogen and stored at −70° C. until ready for total RNA extraction.

Degenerate Primers

Masci-3 (sense) ATGAARGAYAGRCCHGARYTNGAR [SEQ ID NO:27];

Masci-5 (antisense) GTRCTYTCRTGYTCYTCY [SEQ ID NO:28];

Isolation of Total RNA

Total RNA was isolated using the Dynal Bead total RNA extraction kit. Frozen venom glands (2) were placed in 1.0 mL of lysis buffer (supplied in the kit) in an Eppendorf™ tube and immediately homogenised using a RNAase-free sterile Polytron™ probe. Homogenisation was carried on ice in 4×10-second intervals. The homogenate was divided in 0.5 mL aliquots and an equal volume phenol-chloroform (1:1) extraction carried out. The aqueous layer (top) was separated which contained RNA and DNA, which was precipitated with an equal volume of isopropanol overnight. After centrifugation at 13,000 rpm for 20 minutes at 4° C., 70% ethanol washing was carried out. The precipitated RNA was reconstituted in DEPC-treated water and nucleic acid content determined on diluted aliquot by measurement of absorbance at 260 nm, using the formula:

$$\text{Total } RNA \text{ (mg)} = A_{260} \times [0.04 \text{ mg}/(1\ A_{260} \times 1 \text{ mL})] \times \text{dilution factor} \times \text{volume (mL)}.$$

Subsequent total RNA preparations were carried out using TRIzol™ reagent (Life Technologies) as per instruction manual. Briefly, 100 mg tissue was homogenised (using a Polytron™ homogeniser with the small homogenising attachment) in 1 mL of TRIzol™ reagent.

RNA analysis was carried out by electrophoresing a sample on a denaturing formaldehyde agarose/EtBr gel. Mammalian total RNA showed typical two bright bands at 4.5 and 19 kb, these bands corresponds 28S and 18S ribosomal RNA. The ratios of intensity of these bands were approximately 2:1.

Isolation of mRNA

Messenger RNA was isolated using Dynal Magnetic Beads as recommended by supplier. After elution of mRNA from magnetic beads, 1 µg was used for reverse-transcriptase (RT) polymerase chain reaction (PCR) and the remainder was precipitated in one tenth volume of 3 M sodium acetate pH 5.2/2 volumes of absolute ethanol and stored at −70° C.

RT-PCR

RT-PCR was carried using Promega RT kit MMLV-reverse transcriptase and the isolated total RNA (1 µg) and mRNA as template at 42° C. for 1.5 hours. The resulting cDNA was used for second strand synthesis. Second strand synthesis was carried out using T4 DNA polymerase, first strand cDNA as template. The reaction was carried at 14° C. for 3 hours. Final volume of second synthesis reaction was 100 µL. Phenol-chloroform extraction was carried out and aqueous layer (top, containing double stranded cDNA) was transferred into a clean Eppendorf and cDNA was precipitated with ethanol overnight. After centrifugation at 13,000 rpm for 20 minutes at 4° C. precipitate was washed with 70% ethanol and reconstituted in 10 µL of sterile water and stored frozen at −20° C. until used in PCR amplification Txln cDNA using degenerate primers to Txln 1 and 2.

Amplification by PCR of Txln cDNA

Sense and antisense degenerate oligonucleotide primers Masci-3/Masci-5 were designed from the amino acid sequence of Txln1. Genomic DNA was isolated from the liver tissue of the Brown Snake and was also used as template in PCR using degenerate primers to determine the existence of any intron sequences in Txln cDNA.

Using amplification parameters consisting of 94° C./1 minute; 46° C. for 1 minute; 72° C. for 1 minute for 35 cycles, a PCR product of 177 base pairs was obtained corresponding to a polynucleotide encoding an expected 59 amino acids. Similarly, a 177 base pair product was obtained using genomic DNA. The 177 base pair PCR product was ligated into p-GEM 5zf and pGEX-2T, respectively. Resultant recombinant plasmids were used as templates for automated nucleotide sequence analysis. The respective nucleotide sequences encoding the mature polypeptides relating to Txln 1 and Txln 2 are shown in FIGS. 6 and 7.

Preparation of pGEM-2 T Vector pGEM-2T (Pharmacia-Biotech, about 5 pmol) was cleaved with BamHI and EcoRI. The digestion products were fractionated by TAE-agarose gel electrophoresis and the linearised vector was purified using a QIAquick™ DNA extraction kit (QIAGEN) followed by ethanol precipitation.

Ligation pGEM-2T or pGEX vector (0.3 pmol), and 1.5 pmol of 177 base pairs PCR product were added to a ligation mix containing 2 units of T4 DNA ligase in a: total volume 30 μL. The ligation was carried out overnight incubation at 14° C.

Transformation

Electroporation was performed with *E. coli* strain DH5α as host using one third of the ligation mixture (standard conditions). A total of not less than 10 "white" colonies were selected for each construct on indicator standard LB plates containing 0.1 mg ampicillin/mL. Six cDNA isomers were identified with specific designed primers and their sequences are presented.

Cloning was carried out using linearised pGEM-T-vector having a 3' terminal thymidine extending beyond each end of the linearised molecule (Promega Corporation; Cat No. A3600, Part No. A360A, Lot No. 96814). Purified Txln PCR product (prepared using Advantage2 Taq polymerase enzyme system (Clontech)) was ligated into these ends using T4 DNA ligase (Promega Corporation). Recombinant plasmid containing Txln cDNA was then electroporated into *E. coli* DH5α, and suitable transformants were selected using conventional blue/white selection criteria. At least 10 positive colonies were identified as containing the Txln cDNA PCR product (177 base pairs or full-length). Sequencing of Txln cDNA insert was carried out using dye terminator matrix (Clontech; Cat No. 403045) and submitted for sequencing using ABI Prism™ Model 377 sequencer.

Expression

At least ten colonies with good consensus sequences were selected and grown in 2YT medium in the presence of 100 μg/mL ampicillin and 0.1 M IPTG to induce expression. Direct detection of fusion proteins was performed with 12% SDS-PAGE according to Laemmli, UK, (1970, *Nature* 277: 680).

Txln-GST fusion proteins were purified using affinity chromatography glutathione-Sepharose™ 4B (Amersham-Pharmacia Biotech; Cat No. 17-0756-01). Glutathione-Sepharose™ 4B gel was washed in PBS 4 times to ensure all thrombin inhibitors were removed before incubating with Txln-GST fusion proteins. Recombinant Txlns were cleaved from Txln-GST fusion protein bound to glutathione-Sepharose™ by incubating with thrombin (5 U/mg of fusion protein) (Pharmacia-Biotech). For 1 mL of packed gel containing Txln-GST fusion proteins from 1 liter culture, 50 units of thrombin was added and incubated for 21 hours at room temperature. Supernatant samples were removed at 2, 7 and 21 hours and examined by SDS-PAGE for rec Txln.

Refolding of Recombinant Txln

To maximise the efficiency of refolding of recombinant Txln, a combination of procedures was investigated as described for example by Bieri et al (1995, *Biochemistry*, 34:13059–13065), which is incorporated herein by reference, and Norris et al, (1994. Aprotinin analogues and a process for the production thereof, U.S. Pat. No. 5,373,090 to Novo Nordisk), which is incorporated herein by reference.

Briefly, recombinant Txln in 20 mM $NH_4HCO_3$, pH 8.3, with added 2M guanidine hydrochloride was reduced with 45 mM DTT for 15 min 50° C. The reduced and unfolded Txln was then quickly diluted by 100-fold (final salt concentration is less than 0.05M) by adding to 20 mM ammonium bicarbonate buffer, pH 8.3 and left to stand for 18 hours. Concentrating and purification of active recombinant Txln (1–10 mg), was carried out by applying the diluted Txln solution to DEAE-Sepharose™ (1.0×10 cm) ion-exchange column as described for native Txln. Active recombinant Txln was assayed by inhibition of plasmin (0.1 U), using S-2251 (3.0 mM) chromogenic assay. Clinical efficacy of recombinant Txlns was investigated in mouse-tail vein bleeding model.

Results cDNA Sequence of Textilinin 1 Obtained Using Degenerate Primers (Masci-3/Masci-5)

Primers (Masci-3/Masci-5) were designed based on codon redundancy for amino acids and choosing specific regions of N-terminal and C-terminal for Txln 1 and Txln 2 sequences (described below). Those were used to amplify cDNA produced from total RNA isolated from the Brown snake venom gland. The PCR products were cloned into pGEM-5zf(+) using blunt end cloning. Positive clones (white) were further substantiated to contain the insert by PCR screening, using Masci-3/Masci-5 as primers and plasmid DNA, prepared by mini-prep procedure, as template. DNA sequence analysis using an ABI Dye-terminator kit yielded two separate sequences for Txln 1 and Txln 2 (FIGS. 6 and 7). At least 10 separate clones were employed to obtain these sequences.

Design of Gene-Specific Primers to Determine the 5' and 3' Untranslated Regions (UTRs) of Txln cDNA A new set of primers (F1 and R1; Txln2R1) was designed with two nucleotide changes to increase the G-C content and thus the alignment of primer to DNA. The two changes were in codon 6; TTT is changed to TTC (maintaining code for F) and in codon 5; GAT is changed to GAC (again, maintaining the same amino acid, D). A new forward primer, F1 was designed having the sequence below.

F1:Txln 1 Gene-Specific Forward Primer

```
ATATATGGATCCAAGGACCGGCCTGACTTC [SEQ ID NO:29]
      BamHI
```

In the case of the reverse primer, R1, codon AGT (encoding amino acid 59) was changed to TCA, conserving the amino acid, Serine (S) and again, increasing the GC content of the R1 primer. The codon GG(N) (encoding amino acid 58) was changed to a C to optimise binding of the primer to DNA. A corresponding reverse primer specific for Txln 2, R2, was also employed. The primer sequences are listed below:

R1: Txln 1 Gene-Specific Reverse Primer

```
AACGGGAATTCTCAGAGCCACACGTGCTTTC    [SEQ ID NO:30]
     EcoRI stop
```

EcoRI stop

R2 Txln 2 Gene-Specific Reverse Primer

```
AACGGGAATTCTCATGAGCCACAGGTAGACTC    [SEQ ID NO:31]
     EcoRI stop
```

EcoRI stop (Txln 2 gene-specific reverse primer gave a positive PCR product, although it was not used).

Amplification products were separated by agarose gel electrophoresis and a 177 bp amplicon was was purified using QIAquick™ PCR purification kit (QIAGEN). 1–2 µg purified Txln-cDNA PCR product was ligated into pGEM-2T-vector and sequencing carried out using a dye terminator kit (Perken-Elmer Corporation note, August 1995). The nucleotide sequence of Txln cDNA enabled us to design a second set of Txln 1-gene specific primers to determine the 5' and 3' sequences of the gene (3' and 5' RACE methodology). Those primer sequences are given below and have been designated gene specific primers (TX1FN and TX1RN) to distinguish them from the initial set.

5' and 3'-SMART™ RACE cDNA Amplification (Clonetech).

A fresh preparation of cDNA was prepared for each 5'- and 3'-RACE reaction. The SMART™ RACE kit includes a protocol for the synthesis of two separate cDNA populations: 5'-RACE Ready cDNA and 3'-RACE Ready cDNA. The cDNA for 5'-RACE was synthesised using a modifying lock-docking oligo (dT) primer and the SMART™ II oligo. The modified oligo (dT) primer, termed 5'-RACE cDNA Synthesis primer (5'-CD's), has two degenerate oligo positions at the 3' end. These nucleotides position the primer at the start of the poly A+ tail and thus eliminate the 3' heterogeneity inherent with conventional oligo (dT) priming (Borsen et al, 1994, *PCR Methods Applic.* 2:144–148).

The 3' RACE cDNA was synthesised using conventional reverse transcription procedure, but with a special oligo (dT) primer. This 3'-RACE cDNA Synthesis (3'-CD's) primer includes the lock-docking nucleotide positions as in the 5'-CD's primer and also has a portion of the SMART™ sequence at its 5' end. By incorporating the SMART™ sequence in both the 5' and 3'-RACE-Ready™ cDNA populations, one can prime both RACE PCR reactions using the Universal Primer Mix (UPM), that recognises the SMART™ sequence, in conjunction with distinct Txln gene-specific primers. The primer set used for RACE is as follows:

Universal Primer Mix:

Long Universal Primer (0.2 µM),

```
                                    [SEQ ID NO:32]
CTAATACGACTCACTATAGGGCAAGCAGTGGTAACAACGCAGAGT;
```

Short Universal Primer (1 µM),

```
CTAATACGACTCACTATAGGGC;    [SEQ ID NO:33]
```

Nested Universal Primer (NUP; 10 M),

```
AAGCAGTGGTAACAACGCAGAGT.    [SEQ ID NO:34]
```

Figure 8:
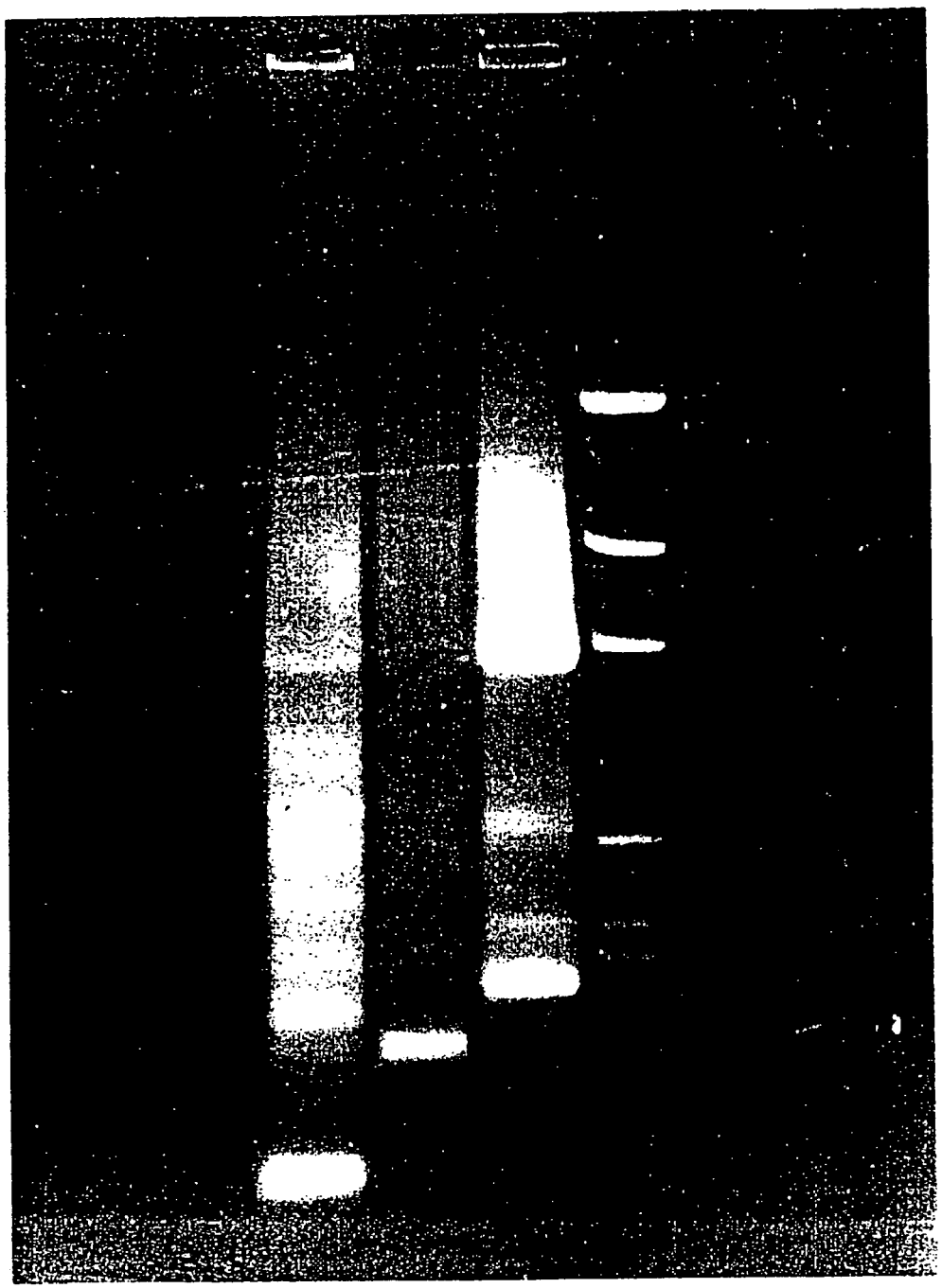
FIG. 8 shows the electrophoretic mobility patterns on a 2% agarose gel stained with EtBr of PCR products obtained with Txln gene-specific primers: Lane 1, control (template, no primers); Lane 2, 5'-RACE PCR product; Lane 3, 3'-RACE PCR product; Lane M; size markers.

FIG. 8 shows the agarose gel electrophoretic mobility patterns of PCR products obtained with Txln gene-specific primers. PCR products (both 5'and 3'-RACE) were electrophoresed, excised and gel purified using QIAquick™ gel extraction kit (QIAGEN).

Cloning of Region Coding for Proform of Txln 1

From 5' and 3' RACE sequences, Txln-gene specific forward (TX1FN) and reverse (TX1RN) primers were designed, containing a BamHI restriction site in TX1FN (first 12 nucleotides) and an EcoRI site in TX1RN (12 nucleotides). The sequences for these primers are listed below:

```
TX1FN                           [SEQ ID NO:35]
ATCAGCGGATCCATGTCTGGAGGT;

TX1RN                           [SEQ ID NO:36]
TCTCCTGAATTCTCAGGCAGCACAGGT.
```

PCR was carried out using cDNA as a template and Advantage2™ Taq polymerase with the following conditions: 92° C./1 min; 50° C./1 min; 72° C./1 min for 30 cycles. These primers amplified a product corresponding to a sequence coding for the Txln1 proform (83 amino acids).

Cloning of Txln 1 Proform

All three PCR products were purified from the gel and cloned into pGEM-2T for DNA sequencing using pGEM specific primers adjacent to the insert. The nucleotide and deduced amino acid sequences outlined in FIG. 9 [SEQ ID NO: 43 and 44, respectively] were derived by sequencing the 3' and 5' RACE products. This allowed the identification of an extra 72 nucleotides upstream of the AAG (K) in frame, suggesting the presence of a proform of Txln1 existed. An extra 24 amino acids exists immediately upstream of the coding 59 amino acids. Eleven (11) nucleotides of 5' UTR was also identified as well as 143 nucleotides of 3' UTR In addition 3' RACE sequencing revealed that the two amino acids immediately upstream from the stop codon were not alanines, not glycine and serine as derived from the original less accurate sequencing. However, additional sequences to Txln 1 and Txln 2 were obtained by sequencing multiple clones. After extensive sequencing, it became apparent that there were six separate Txln genes.

Cloning for the Coding Region of Txln1

Similarly, Txln gene-specific primers were designed to obtain a PCR product, which encoded the active peptide (59 amino acids). Again, in this case, a BamHI site was incorporated into the forward primer (TX1TF) and the reverse primer was the RACE-Ready Universal primer (Long SMART™).

Txln-Active Peptide Sequence Primers:

TX1TF (forward),                [SEQ ID NO:37]
ATTATAGGATCC<u>AA</u>GGACCGTCCGGAT;

RACE-Ready Long Universal Primer

[SEQ ID NO:32]
CTAATACGACTCACTATAGGGCAAGCAGTGGTAACAACGCAGAGT.

Cloning of Additional Txln Genes

Forward primers were also designed for Txln 2–6 (below), and in combination with long Universal Primer (LUP, Clontech RACE-Ready Kit), using the PCR conditions as described above. The sequences for these primers are as follows:

ATTATAGGATCC<u>AA</u>GGACCGTCCAGAG;    [SEQ ID NO:38]

AACGTCGGATCC<u>AA</u>GGACCGTCCAAAT;    [SEQ ID NO:30]

AACGTCGGATCC<u>AA</u>GGACCATCCAAAA;    [SEQ ID NO:40]

AACGTCGGATTC<u>AA</u>GGACCGTCCAAAA and; [SEQ ID NO:41]

ATTGTCGGATCC<u>AA</u>GGACCTGCCAAAG    [SEQ ID NO:42].

In all cases, the forward primer had a BamHI site inserted to facilitate cloning. The underlined sequence marks the start triplet for the coding sequence.

Amplification products obtained using the above primers were fractionated by agarose gel electrophoresis and DNA fragments with the appropriate size were purified, and cloned into pGEM-2T vector. Sequencing of recombinant plasmids was performed using a Clontech dye terminator matrix and an ABI Prism™ Model 377 sequencer. Nucleotide sequences obtained by this procedure for Txln 1–6 are presented in FIG. 10 together with the corresponding deduced amino acid sequences. As will be apparent from inspection of FIG. 11, the Txln amino acid sequences are highly homologous and in this regard, a consensus sequence is provided.

Recloning of Txln cDNA Gel Purified PCR Product into pGEX-2T Expression Vectors

Recombinant Txln (both 59 amino acid peptide and 83 amino acid molecule containing 24 amino acid propeptide) were expressed using pGEX-2T constructs. Recombinant Txln activity was assayed by using the chromogenic substrate S-2251 and enzyme plasmin (Friberger et al, 1978). SDS-PAGE and Western blotting using polyvalent antibodies to Txln identified recombinant Txln FIG. 12).

Example 3

Production of a Fibrin-Specific Monoclonal Antibody-Textilinin 1 Conjugate

A fibrin specific monoclonal antibody, MAb 12B3.B10 (IgG2A/kappa) (Tymkewycz et al, 1993, supra), will be chemically conjugated with the plasmin inhibitor Txln 1 by a two step zero length crosslinking procedure according to Grabarek and Gergely (1990, *Anal. Biochem.* 185:131–135). Briefly Txln 1 will be incubated with a water soluble carbodiimide (EDC) in the presence of N-Hydroxysuccinimide (sulfo-NHS), and will result in the conversion of the carboxyl groups of Glu or Asp into succinimidyl esters. After removing excess EDC by gel filtration MAb 12B3.B10 will be added to the activated Txln 1. Crosslinking will result from nucleophilic substitution of the lysine-amino groups of the IgG for the succinimidyl moieties during a 2h incubation. The IgG-Txln 1 conjugate will then purified from free Txln 1 via size exclusion HPLC on a Superdex 200 HR 10/30 column as described by Raut and Gaffney (1996, *Fibrinolysis* 10 (Suppl. 4):1–26, Abstract No 39). The purified construct will then be tested for plasmin inhibitory activity by ELISA using the Chromogenic substrate S-2251.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appendant claims.

TABLE LEGENDS

TABLE 1. Conservative amino acid substitutions

TABLE 2 Unconventional amino acids for generation of modified peptides.

TABLE 3. Summary of inhibitory constants. $K_i$ for Txln S-100 Pool measured using Enzfitter analysis programme, using plasmin concentration 0.5 nM, was 0.15 μM (n=6). *Denotes data obtained from previous work (Willmott et al., 1995, supra) where the concentration of plasmin was used to determine $K_i$ for aprotinin was 0.5 nM.

TABLE 4. Mouse tail bleeding model—Blood loss determination. The blood loss in the mice treated with aprotinin and the two forms of Txln (1 and 2) compared to a saline control group is shown, while the percentage reduction in blood loss is also given.

The invention claimed is:

1. A substantially pure preparation of a plasmin inhibitor characterised in that it is a single stage competitive inhibitor of plasmin, wherein "substantially pure" means that at least 60% of the total material in the preparation is the plasmin inhibitor, and wherein the plasmin inhibitor comprises a polypeptide with at least 90% sequence identity to one selected from the group consisting of SEQ ID NO:2, SEQ ID NO:4, SEQ ID NO:6, SEQ ID NO:8, SEQ ID NO:10, SEQ ID NO:12, and the general formula: KDZPZŸCZLBBZB-GXCZXXXBXFÅYXBZZZZCBZFBYGGCX-BNANNFXTXEECE STCAA (I) (SEQ ID NO 67), wherein:

X is any amino acid selected from the group consisting of Ala, Arg, Asn, Asp, Cys, Gln, Glu, Gly, His, Ile, Leu, Lys, Met, Phe, Pro, Ser, Thr, Trp, Tyr, Val, α-aminobutyric acid, L-N-methylalanine, α-amino-α-methylbutyrate, L-N-methylarginine, aminocyclopropane-carboxylate, L-N-methylasparagine, aminoisobutyric acid, L-N-methylaspartic acid, aminonorbornyl-carboxylate, L-N-methylcysteine, cyclohexylalanine, L-N-methylglutamine, cyclopentylalanine, L-N-methylglutamic acid, L-N-methylisoleucine, L-N-methylhistidine, D-alanine, L-N-methylleucine, D-arginine, L-N-methyllysine, D-aspartic acid, L-N-methylmethionine, D-cysteine, L-N-methylnorleucine, D-glutamate, L-N-methylnorvaline, D-glutamic acid, L-N-methylornithine, D-histidine, L-N-methylphenylalanine, D-isoleucine, L-N-methylproline, D-leucine, L-N-medlylserine, D-lysine, L-N-methylthreonine, D-methionine, L-N-methyltryptophan, D-ornithine, L-N-methyltyrosine, D-phenylalanine, L-N-methylvaline, D-proline, L-N-methylethylglycine, D-serine, L-N-methyl-t-butylglycine, D-threonine, L-norleucine, D-tryptophan, L-norvaline, D-tyrosine, α-methyl-aminoisobutyrate, D-valine, α-methyl-γ-aminobutyrate, D-α-methylalanine, α-methylcyclohexylalanine, D-α-methylarginine, α-methylcylcopentylalanine, D-α-methylasparagine, α-methyl-α-napthylalanine, D-α-methylaspartate, α-methylpenicillamine, D-α-methylcysteine, N-(4-aminobutyl)glycine, D-α-methylglutamine, N-(2-aminoethyl)glycine, D-α-methylhistidine, N-(3-aminopropyl)glycine, D-α-methylisoleucine, N-amino-α-methylbutyrate, D-α-methylleucine, α-napthylalanine, D-α-methyllysine, N-benzylglycine, D-α-methylmethionine, N-(2-carbamylediyl)glycine, D-α-methylornithiine, N-(carbamylmethyl)glycine, D-α-methylphenylalanine, N-(2-carboxyethyl)glycine, D-α-methylproline, N-(carboxymethyl)glycine, D-α-methylserine, N-cyclobutylglycine, D-α-methylthreonine, N-cycloheptylglycine, D-α-methyltryptophan, N-cyclohexylglycine, D-α-methyltyrosine, N-cyclodecylglycine, L-α-methylleucine, L-α-methyllysine, L-α-methylmethionine, L-α-methylnorleucine, L-α-methylnorvatine, L-α-methylornithine, L-α-methylphenylalanine, L-α-methylproline, L-α-methylserine, L-α-methylthreonine, L-α-methyltryptophan, L-α-methyltyrosine, L-α-methylvaline, L-N-methylhomophenylalanine, N-(N-(2,2-diphenylethyl carbamylmethyl)glycine, N-(N-(3,3-diphenylpropyl carbamylmethyl)glycine, and 1-carboxy-1-(2,2-diphenyl-ethyl amino)cyclopropane;

Ÿ is a hydrophobic amino acid;

Ã is an aromatic amino acid;

Z is K, R, H, D, E, Q or N; and

B is a neutral amino acid, or P, A, G, S, T, V or L.

2. The plasmin inhibitor of claim 1 further characterised in that it has a dissociation constant for plasmin in the range of from $1\times10^{-8}$ $M^{-1}$ to $1\times10^{-10}$ $M^{-1}$.

3. The plasmin inhibitor of claim 1 further characterised in that it has a dissociation constant for plasmin in the range of from $5\times10^{-8}$ $M^{-1}$ to $8\times10^{-9}$ $M^{-1}$.

4. The plasmin inhibitor of claim 1 further characterised in that it has a dissociation constant for plasmin in the range of from $1\times10^{-9}$ $M^{-1}$ to $5\times10^{-9}$ $M^{-1}$.

5. The plasmin inhibitor of claim 1 further characterised in that it has a dissociation rate constant for plasmin in the range of from $4\times10^{-5}$ $sec^{-1}$ $M^{-1}$ to $5\times10^{-7}$ $sec^{-1}$ $M^{-1}$.

6. The plasmin inhibitor of claim 1 further characterised in that it has a dissociation rate constant for plasmin in the range of from $1\times10^{-6}$ $sec^{-1}$ $M^{-1}$ to $1\times10^{-7}$ $sec^{-1}$ $M^{-1}$.

7. The plasmin inhibitor of claim 1 further characterised in that it has a dissociation rate constant for plasmin in the range of from $2\times10^{-6}$ $sec^{-1}$ $M^{-1}$ to $9\times10^{-6}$ $sec^{-1}$ $M^{-1}$.

8. The plasmin inhibitor of claim 1, wherein the polypeptide is selected from the group consisting of: SEQ ID NO:2, SEQ ID NO:4, SEQ ID NO:6, SEQ ID NO:8, SEQ ID NO:10, and SEQ ID NO:12.

9. The plasmin inhibitor of claim 1, wherein the polypeptide is SEQ ID NO 67.

10. The plasmin inhibitor of claim 9, wherein the Z at position 3 is H or R.

11. The plasmin inhibitor of claim 9, wherein the Z at position 5 is K, N, E or D.

12. The plasmin inhibitor of claim 9, wherein the Ÿ at position 6 is F or L.

13. The plasmin inhibitor of claim 9, wherein the Z at position 8 is E or K.

14. The plasmin inhibitor of claim 9, wherein the B at position 10 is P or L.

15. The plasmin inhibitor of claim 9, wherein the B at position 11 is P or A.

16. The plasmin inhibitor of claim 9, wherein the Z at position 12 is E or D.

17. The plasmin inhibitor of claim 9, wherein the B at position 13 is T or I.

18. The plasmin inhibitor of claim 9, wherein the X at position 15 is P, S or R.

19. The plasmin inhibitor of claim 9, wherein the Z at position 17 is K, N, E, D or R.

20. The plasmin inhibitor of claim 9, wherein the X at position 18 is D, G, A or V.

21. The plasmin inhibitor of claim 9, wherein the X at position 19 is F, N, K or R.

22. The plasmin inhibitor of claim 9, wherein the X at position 20 is T, P, F or I.

23. The plasmin inhibitor of claim 9, wherein the B at position 21 is G, V or P.

24. The plasmin inhibitor of claim 9, wherein the X at position 22 is A, S or R.

25. The plasmin inhibitor of claim 9, wherein the Ã at position 24 is Y or H.

26. The plasmin inhibitor of claim 9, wherein the X at position 26 is S or N.

27. The plasmin inhibitor of claim 9, wherein the B at position 27 is P, A or T.

28. The plasmin inhibitor of claim 9, wherein the Z at position 28 may be D or R.

29. The plasmin inhibitor of claim 9, wherein the Z at position 29 is E, D, H or Q.

30. The plasmin inhibitor of claim 9, wherein the Z at position 30 is H, K, R or Q.

31. The plasmin inhibitor of claim 9, wherein the Z at position 31 is K, Q or E.

32. The plasmin inhibitor of claim 9, wherein the B at position 33 is L or I.

33. The plasmin inhibitor of claim 9, wherein the Z at position 34 is E or K.

34. The plasmin inhibitor of claim 9, wherein the B at position 36 is L or I.

35. The plasmin inhibitor of claim 9, wherein the X at position 41 is E, G or K.

36. The plasmin inhibitor of claim 9, wherein the B at position 42 is C or G.

37. The plasmin inhibitor of claim 9, wherein the X at position 48 is K, N or I.

38. The plasmin inhibitor of claim 9, wherein the X at position 50 is K, Q or I.

39. The plasmin inhibitor of claim 8 or claim 9, wherein the polypeptide comprises a leader peptide comprising SEQ ID No:14.

40. The plasmin inhibitor of claim 39, wherein the polypeptide is selected from the group consisting of: SEQ ID NO: 16, SEQ ID NO: 18, SEQ ID NO: 20, SEQ ID NO: 22, SEQ ID NO: 24, SEQ ID NO: 26.

41. A pharmaceutical composition for alleviating blood loss in a patient, said composition comprising the polypeptide of claim 8 and a pharmaceutically acceptable carrier.

42. The plasmin inhibitor of claim 1, further comprising the amino acid sequence ECESTCAA (SEQ ID NO. 68).

43. The plasmin inhibitor of claim 1, further comprising the amino acid sequence NANNF (SEQ ID NO. 69).

44. The plasmin inhibitor of claim 42, further comprising the amino acid sequence YGGC (SEQ ID NO. 70).

45. The plasmin inhibitor of claim 1, which is conjugated to an anti-fibrin antibody.

46. The plasmin inhibitor of claim 1, wherein "substantially pure" means that at least 75% of the total material in the preparation is the plasmin inhibitor.

47. The plasmin inhibitor of claim 1, wherein "substantially pure" means that at least 90% of the total material in the preparation is the plasmin inhibitor.

48. The plasmin inhibitor of claim 1, wherein "substantially pure" means that at least 95% of the total material in the preparation is the plasmin inhibitor.

* * * * *

UNITED STATES PATENT AND TRADEMARK OFFICE
CERTIFICATE OF CORRECTION

PATENT NO. : 7,070,969 B1
APPLICATION NO. : 09/700179
DATED : July 4, 2006
INVENTOR(S) : Pantaleone Paul Masci et al.

Page 1 of 1

It is certified that error appears in the above-identified patent and that said Letters Patent is hereby corrected as shown below:

IN THE SPECIFICATION

In the BRIEF DESCRIPTION OF THE DRAWINGS section, column 8, line 39, please replace "FIG. 2" with -- FIG. 3 --.

In column 8, line 44, please replace "FIG. 3" with -- FIG. 2 --.

Figure 2:
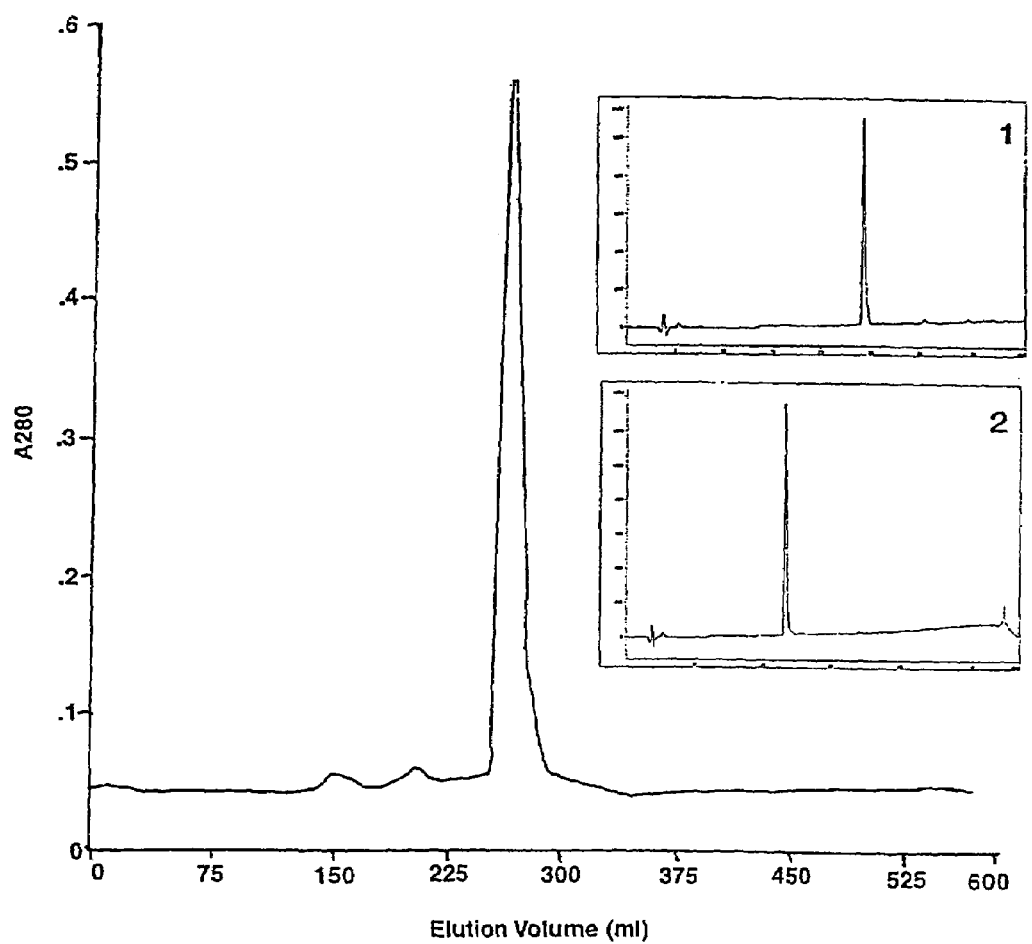
FIG. 2 depicts a DEAE-Sepharose™ CL-6B column elution profile of concentrated plasmin inhibitor activity derived from the Sephacryl™ S-300 chromatography in FIG. 1. The solid bars show two separate peaks of plasmin inhibitory activity (denoted 1 and 2).

In column 29, line 21, replace "FIG. 1(a)" with -- FIG. 1 --.

In column 29, line 29, replace "FIG. 1(b)" with -- FIG. 3 --.

In column 29, line 52, replace "FIG. 3" with -- FIG. 5 --.

In the DISCUSSION section, column 32, line 27, replace "(FIGS. 1 and 2)" with -- (FIGS. 1 and 3) --.

In column 32, line 35, replace "FIG. 3" with -- FIG. 5 --.

Signed and Sealed this

Ninth Day of June, 2009

JOHN DOLL
*Acting Director of the United States Patent and Trademark Office*

SEQUENCE LISTING

```
<160> NUMBER OF SEQ ID NOS: 70

<210> SEQ ID NO 1
<211> LENGTH: 180
<212> TYPE: DNA
<213> ORGANISM: Pseudonaja textilis
<220> FEATURE:
<221> NAME/KEY: CDS
```

-continued

```
<222> LOCATION: (1)..(180)
<220> FEATURE:
<221> NAME/KEY: mat_peptide
<222> LOCATION: (1)..(180)

<400> SEQUENCE: 1 aag gac cgt ccg gat ttc tgt gaa ctg cct gct gac acc gga cca tgt      48
Lys Asp Arg Pro Asp Phe Cys Glu Leu Pro Ala Asp Thr Gly Pro Cys
  1               5                  10                  15 aga gtc aga ttc cca tcc ttc tac tac aac cca gat gaa aaa aag tgc      96
Arg Val Arg Phe Pro Ser Phe Tyr Tyr Asn Pro Asp Glu Lys Lys Cys
                 20                  25                  30 cta gag ttt att tat ggt gga tgc gaa ggg aat gct aac aat ttt atc     144
Leu Glu Phe Ile Tyr Gly Gly Cys Glu Gly Asn Ala Asn Asn Phe Ile
             35                  40                  45 acc aaa gag gaa tgc gaa agc acc tgt gct gcc tga                     180
Thr Lys Glu Glu Cys Glu Ser Thr Cys Ala Ala
         50                  55

<210> SEQ ID NO 2
<211> LENGTH: 59
<212> TYPE: PRT
<213> ORGANISM: Pseudonaja textilis

<400> SEQUENCE: 2

Lys Asp Arg Pro Asp Phe Cys Glu Leu Pro Ala Asp Thr Gly Pro Cys
  1               5                  10                  15

Arg Val Arg Phe Pro Ser Phe Tyr Tyr Asn Pro Asp Glu Lys Lys Cys
                 20                  25                  30

Leu Glu Phe Ile Tyr Gly Gly Cys Glu Gly Asn Ala Asn Asn Phe Ile
             35                  40                  45

Thr Lys Glu Glu Cys Glu Ser Thr Cys Ala Ala
         50                  55

<210> SEQ ID NO 3
<211> LENGTH: 180
<212> TYPE: DNA
<213> ORGANISM: Pseudonaja textilis
<220> FEATURE:
<221> NAME/KEY: CDS
<222> LOCATION: (1)..(180)
<220> FEATURE:
<221> NAME/KEY: mat_peptide
<222> LOCATION: (1)..(180)

<400> SEQUENCE: 3 aag gac cgt cca gag ttg tgt gaa ctg cct cct gac acc gga cca tgt      48
Lys Asp Arg Pro Glu Leu Cys Glu Leu Pro Pro Asp Thr Gly Pro Cys
  1               5                  10                  15 aga gtc aga ttc cca tcc ttc tac tac aac cca gat gaa caa aaa tgc      96
Arg Val Arg Phe Pro Ser Phe Tyr Tyr Asn Pro Asp Glu Gln Lys Cys
                 20                  25                  30 cta gag ttt att tat ggt gga tgc gaa ggg aat gct aac aat ttt atc     144
Leu Glu Phe Ile Tyr Gly Gly Cys Glu Gly Asn Ala Asn Asn Phe Ile
             35                  40                  45 acc aaa gag gaa tgc gaa agc acc tgt gct gcc tga                     180
Thr Lys Glu Glu Cys Glu Ser Thr Cys Ala Ala
         50                  55

<210> SEQ ID NO 4
<211> LENGTH: 59
<212> TYPE: PRT
<213> ORGANISM: Pseudonaja textilis
```

-continued

```
<400> SEQUENCE: 4

Lys Asp Arg Pro Glu Leu Cys Glu Leu Pro Asp Thr Gly Pro Cys
 1               5                  10                  15

Arg Val Arg Phe Pro Ser Phe Tyr Tyr Asn Pro Asp Glu Gln Lys Cys
                20                  25                  30

Leu Glu Phe Ile Tyr Gly Gly Cys Glu Gly Asn Ala Asn Asn Phe Ile
            35                  40                  45

Thr Lys Glu Glu Cys Glu Ser Thr Cys Ala Ala
        50                  55

<210> SEQ ID NO 5
<211> LENGTH: 180
<212> TYPE: DNA
<213> ORGANISM: Pseudonaja textilis
<220> FEATURE:
<221> NAME/KEY: CDS
<222> LOCATION: (1)..(180)
<220> FEATURE:
<221> NAME/KEY: mat_peptide
<222> LOCATION: (1)..(180)

<400> SEQUENCE: 5 aag gac cgt cca aat ttc tgt aaa ctg cct gct gaa acc gga cga tgt     48
Lys Asp Arg Pro Asn Phe Cys Lys Leu Pro Ala Glu Thr Gly Arg Cys
 1               5                  10                  15 aat gcc aaa atc cca cgc ttc tac tac aac cca cgt caa cat caa tgc     96
Asn Ala Lys Ile Pro Arg Phe Tyr Tyr Asn Pro Arg Gln His Gln Cys
                20                  25                  30 ata gag ttt ctc tat ggt gga tgc gga ggg aat gct aac aat ttt aag    144
Ile Glu Phe Leu Tyr Gly Gly Cys Gly Gly Asn Ala Asn Asn Phe Lys
            35                  40                  45 acc att aag gaa tgc gaa agc acc tgt gct gca tga                    180
Thr Ile Lys Glu Cys Glu Ser Thr Cys Ala Ala
        50                  55

<210> SEQ ID NO 6
<211> LENGTH: 59
<212> TYPE: PRT
<213> ORGANISM: Pseudonaja textilis

<400> SEQUENCE: 6

Lys Asp Arg Pro Asn Phe Cys Lys Leu Pro Ala Glu Thr Gly Arg Cys
 1               5                  10                  15

Asn Ala Lys Ile Pro Arg Phe Tyr Tyr Asn Pro Arg Gln His Gln Cys
                20                  25                  30

Ile Glu Phe Leu Tyr Gly Gly Cys Gly Gly Asn Ala Asn Asn Phe Lys
            35                  40                  45

Thr Ile Lys Glu Cys Glu Ser Thr Cys Ala Ala
        50                  55

<210> SEQ ID NO 7
<211> LENGTH: 180
<212> TYPE: DNA
<213> ORGANISM: Pseudonaja textilis
<220> FEATURE:
<221> NAME/KEY: CDS
<222> LOCATION: (1)..(180)
<220> FEATURE:
<221> NAME/KEY: mat_peptide
<222> LOCATION: (1)..(180)

<400> SEQUENCE: 7 aag gac cat cca aaa ttc tgt gaa ctc cct gct gaa acc gga tca tgt     48
```

```
Lys Asp His Pro Lys Phe Cys Glu Leu Pro Ala Glu Thr Gly Ser Cys
 1               5                  10                  15 aaa ggc aac gtc cca cgc ttc tac tac aac gca gat cat cat caa tgc      96
Lys Gly Asn Val Pro Arg Phe Tyr Tyr Asn Ala Asp His His Gln Cys
                20                  25                  30 cta aaa ttt att tat ggt gga tgt gga ggg aat gct aac aat ttt aag     144
Leu Lys Phe Ile Tyr Gly Gly Cys Gly Gly Asn Ala Asn Asn Phe Lys
        35                  40                  45 acc ata gag gaa ggc aaa agc acc tgt gct gcc tga                     180
Thr Ile Glu Glu Gly Lys Ser Thr Cys Ala Ala
        50                  55
```

<210> SEQ ID NO 8
<211> LENGTH: 59
<212> TYPE: PRT
<213> ORGANISM: Pseudonaja textilis

<400> SEQUENCE: 8

```
Lys Asp His Pro Lys Phe Cys Glu Leu Pro Ala Glu Thr Gly Ser Cys
 1               5                  10                  15

Lys Gly Asn Val Pro Arg Phe Tyr Tyr Asn Ala Asp His His Gln Cys
                20                  25                  30

Leu Lys Phe Ile Tyr Gly Gly Cys Gly Gly Asn Ala Asn Asn Phe Lys
        35                  40                  45

Thr Ile Glu Glu Gly Lys Ser Thr Cys Ala Ala
        50                  55
```

<210> SEQ ID NO 9
<211> LENGTH: 180
<212> TYPE: DNA
<213> ORGANISM: Pseudonaja textilis
<220> FEATURE:
<221> NAME/KEY: CDS
<222> LOCATION: (1)..(180)
<220> FEATURE:
<221> NAME/KEY: mat_peptide
<222> LOCATION: (1)..(180)

<400> SEQUENCE: 9

```
aag gac cgt cca aaa ttc tgt gaa ctg ctt cct gac acc gga tca tgt      48
Lys Asp Arg Pro Lys Phe Cys Glu Leu Leu Pro Asp Thr Gly Ser Cys
 1               5                  10                  15 gaa gac ttt acc gga gcc ttc cac tac agc aca cgt gat cgt gaa tgc      96
Glu Asp Phe Thr Gly Ala Phe His Tyr Ser Thr Arg Asp Arg Glu Cys
                20                  25                  30 ata gag ttt att tat ggt gga tgc gga ggg aat gct aac aat ttt atc     144
Ile Glu Phe Ile Tyr Gly Gly Cys Gly Gly Asn Ala Asn Asn Phe Ile
        35                  40                  45 acc aaa gag gaa tgc gaa agc acc tgt gct gcc tga                     180
Thr Lys Glu Glu Cys Glu Ser Thr Cys Ala Ala
        50                  55
```

<210> SEQ ID NO 10
<211> LENGTH: 59
<212> TYPE: PRT
<213> ORGANISM: Pseudonaja textilis

<400> SEQUENCE: 10

```
Lys Asp Arg Pro Lys Phe Cys Glu Leu Leu Pro Asp Thr Gly Ser Cys
 1               5                  10                  15

Glu Asp Phe Thr Gly Ala Phe His Tyr Ser Thr Arg Asp Arg Glu Cys
                20                  25                  30
```

```
Ile Glu Phe Ile Tyr Gly Gly Cys Gly Gly Asn Ala Asn Asn Phe Ile
         35                  40                  45

Thr Lys Glu Glu Cys Glu Ser Thr Cys Ala Ala
 50                  55
```

<210> SEQ ID NO 11
<211> LENGTH: 180
<212> TYPE: DNA
<213> ORGANISM: Pseudonaja textilis
<220> FEATURE:
<221> NAME/KEY: CDS
<222> LOCATION: (1)..(180)
<220> FEATURE:
<221> NAME/KEY: mat_peptide
<222> LOCATION: (1)..(180)

<400> SEQUENCE: 11

```
aag gac cgt cca aag ttc tgt gaa ctg cct gct gac atc gga cca tgg      48
Lys Asp Arg Pro Lys Phe Cys Glu Leu Pro Ala Asp Ile Gly Pro Trp
  1               5                  10                  15 gat gac ttt acc gga gcc ttc cac tac agc cca cgt gaa cat gaa tgc      96
Asp Asp Phe Thr Gly Ala Phe His Tyr Ser Pro Arg Glu His Glu Cys
                 20                  25                  30 ata gag ttt att tat ggt gga tgc aaa ggg aat gct aac aac ttt aat     144
Ile Glu Phe Ile Tyr Gly Gly Cys Lys Gly Asn Ala Asn Asn Phe Asn
         35                  40                  45 acc caa gag caa tgc gaa agc acc tgt gct gcc tga                     180
Thr Gln Glu Gln Cys Glu Ser Thr Cys Ala Ala
 50                  55
```

<210> SEQ ID NO 12
<211> LENGTH: 59
<212> TYPE: PRT
<213> ORGANISM: Pseudonaja textilis

<400> SEQUENCE: 12

```
Lys Asp Arg Pro Lys Phe Cys Glu Leu Pro Ala Asp Ile Gly Pro Trp
  1               5                  10                  15

Asp Asp Phe Thr Gly Ala Phe His Tyr Ser Pro Arg Glu His Glu Cys
                 20                  25                  30

Ile Glu Phe Ile Tyr Gly Gly Cys Lys Gly Asn Ala Asn Asn Phe Asn
         35                  40                  45

Thr Gln Glu Gln Cys Glu Ser Thr Cys Ala Ala
 50                  55
```

<210> SEQ ID NO 13
<211> LENGTH: 72
<212> TYPE: DNA
<213> ORGANISM: Pseudonaja textilis
<220> FEATURE:
<221> NAME/KEY: sig_peptide
<222> LOCATION: (1)..(72)
<220> FEATURE:
<221> NAME/KEY: CDS
<222> LOCATION: (1)..(72)

<400> SEQUENCE: 13

```
atg tct tct gga ggt ctt ctt ctc ctg ctg gga ctc ctc acc ctc tgg      48
Met Ser Ser Gly Gly Leu Leu Leu Leu Leu Gly Leu Leu Thr Leu Trp
  1               5                  10                  15 gag gtg ctg acc ccc gtc tcc agc                                      72
Glu Val Leu Thr Pro Val Ser Ser
                 20
```

<210> SEQ ID NO 14
<211> LENGTH: 24
<212> TYPE: PRT
<213> ORGANISM: Pseudonaja textilis

<400> SEQUENCE: 14

Met Ser Ser Gly Gly Leu Leu Leu Leu Gly Leu Leu Thr Leu Trp
1               5                   10                  15

Glu Val Leu Thr Pro Val Ser Ser
            20

<210> SEQ ID NO 15
<211> LENGTH: 252
<212> TYPE: DNA
<213> ORGANISM: Pseudonaja textilis
<220> FEATURE:
<221> NAME/KEY: CDS
<222> LOCATION: (1)..(249)
<220> FEATURE:
<221> NAME/KEY: sig_peptide
<222> LOCATION: (1)..(72)
<220> FEATURE:
<221> NAME/KEY: mat_peptide
<222> LOCATION: (73)..(249)

<400> SEQUENCE: 15 atg tct tct gga ggt ctt ctt ctc ctg ctg gga ctc ctc acc ctc tgg        48
Met Ser Ser Gly Gly Leu Leu Leu Leu Leu Gly Leu Leu Thr Leu Trp
            -20                 -15                 -10 gag gtg ctg acc ccc gtc tcc agc aag gac cgt ccg gat ttc tgt gaa        96
Glu Val Leu Thr Pro Val Ser Ser Lys Asp Arg Pro Asp Phe Cys Glu
        -5                  -1   1                   5 ctg cct gct gac acc gga cca tgt aga gtc aga ttc cca tcc ttc tac       144
Leu Pro Ala Asp Thr Gly Pro Cys Arg Val Arg Phe Pro Ser Phe Tyr
         10                  15                  20 tac aac cca gat gaa aaa aag tgc cta gag ttt att tat ggt gga tgc       192
Tyr Asn Pro Asp Glu Lys Lys Cys Leu Glu Phe Ile Tyr Gly Gly Cys
 25                  30                  35                  40 gaa ggg aat gct aac aat ttt atc acc aaa gag gaa tgc gaa agc acc       240
Glu Gly Asn Ala Asn Asn Phe Ile Thr Lys Glu Glu Cys Glu Ser Thr
                 45                  50                  55 tgt gct gcc tga                                                        252
Cys Ala Ala <210> SEQ ID NO 16
<211> LENGTH: 83
<212> TYPE: PRT
<213> ORGANISM: Pseudonaja textilis

<400> SEQUENCE: 16

Met Ser Ser Gly Gly Leu Leu Leu Leu Leu Gly Leu Leu Thr Leu Trp
            -20                 -15                 -10

Glu Val Leu Thr Pro Val Ser Ser Lys Asp Arg Pro Asp Phe Cys Glu
        -5                  -1   1                   5

Leu Pro Ala Asp Thr Gly Pro Cys Arg Val Arg Phe Pro Ser Phe Tyr
         10                  15                  20

Tyr Asn Pro Asp Glu Lys Lys Cys Leu Glu Phe Ile Tyr Gly Gly Cys
 25                  30                  35                  40

Glu Gly Asn Ala Asn Asn Phe Ile Thr Lys Glu Glu Cys Glu Ser Thr
                 45                  50                  55

Cys Ala Ala

<210> SEQ ID NO 17
<211> LENGTH: 252
<212> TYPE: DNA
<213> ORGANISM: Pseudonaja textilis
<220> FEATURE:
<221> NAME/KEY: CDS
<222> LOCATION: (1)..(249)
<220> FEATURE:
<221> NAME/KEY: sig_peptide
<222> LOCATION: (1)..(72)
<220> FEATURE:
<221> NAME/KEY: mat_peptide
<222> LOCATION: (73)..(249)

<400> SEQUENCE: 17

```
atg tct tct gga ggt ctt ctt ctc ctg ctg gga ctc ctc acc ctc tgg      48
Met Ser Ser Gly Gly Leu Leu Leu Leu Leu Gly Leu Leu Thr Leu Trp
            -20                 -15                 -10 gag gtg ctg acc ccc gtc tcc agc aag gac cgt cca gag ttg tgt gaa      96
Glu Val Leu Thr Pro Val Ser Ser Lys Asp Arg Pro Glu Leu Cys Glu
         -5                  -1   1               5 ctg cct cct gac acc gga cca tgt aga gtc aga ttc cca tcc ttc tac     144
Leu Pro Pro Asp Thr Gly Pro Cys Arg Val Arg Phe Pro Ser Phe Tyr
         10                  15                  20 tac aac cca gat gaa caa aaa tgc cta gag ttt att tat ggt gga tgc     192
Tyr Asn Pro Asp Glu Gln Lys Cys Leu Glu Phe Ile Tyr Gly Gly Cys
 25                  30                  35                  40 gaa ggg aat gct aac aat ttt atc acc aaa gag gaa tgc gaa agc acc     240
Glu Gly Asn Ala Asn Asn Phe Ile Thr Lys Glu Glu Cys Glu Ser Thr
                     45                  50                  55 tgt gct gcc tga                                                      252
Cys Ala Ala
```

<210> SEQ ID NO 18
<211> LENGTH: 83
<212> TYPE: PRT
<213> ORGANISM: Pseudonaja textilis

<400> SEQUENCE: 18

```
Met Ser Ser Gly Gly Leu Leu Leu Leu Leu Gly Leu Leu Thr Leu Trp
            -20                 -15                 -10

Glu Val Leu Thr Pro Val Ser Ser Lys Asp Arg Pro Glu Leu Cys Glu
         -5                  -1   1               5

Leu Pro Pro Asp Thr Gly Pro Cys Arg Val Arg Phe Pro Ser Phe Tyr
         10                  15                  20

Tyr Asn Pro Asp Glu Gln Lys Cys Leu Glu Phe Ile Tyr Gly Gly Cys
 25                  30                  35                  40

Glu Gly Asn Ala Asn Asn Phe Ile Thr Lys Glu Glu Cys Glu Ser Thr
                     45                  50                  55

Cys Ala Ala
```

<210> SEQ ID NO 19
<211> LENGTH: 252
<212> TYPE: DNA
<213> ORGANISM: Pseudonaja textilis
<220> FEATURE:
<221> NAME/KEY: CDS
<222> LOCATION: (1)..(249)
<220> FEATURE:
<221> NAME/KEY: sig_peptide
<222> LOCATION: (1)..(72)
<220> FEATURE:
<221> NAME/KEY: mat_peptide
<222> LOCATION: (73)..(249)

```
<400> SEQUENCE: 19 atg tct tct gga ggt ctt ctt ctc ctg ctg gga ctc ctc acc ctc tgg      48
Met Ser Ser Gly Gly Leu Leu Leu Leu Leu Gly Leu Leu Thr Leu Trp
            -20                 -15                 -10 gag gtg ctg acc ccc gtc tcc agc aag gac cgt cca aat ttc tgt aaa      96
Glu Val Leu Thr Pro Val Ser Ser Lys Asp Arg Pro Asn Phe Cys Lys
         -5                  -1   1                   5 ctg cct gct gaa acc gga cga tgt aat gcc aaa atc cca cgc ttc tac     144
Leu Pro Ala Glu Thr Gly Arg Cys Asn Ala Lys Ile Pro Arg Phe Tyr
         10                  15                  20 tac aac cca cgt caa cat caa tgc ata gag ttt ctc tat ggt gga tgc     192
Tyr Asn Pro Arg Gln His Gln Cys Ile Glu Phe Leu Tyr Gly Gly Cys
         25                  30                  35              40 gga ggg aat gct aac aat ttt aag acc att aag gaa tgc gaa agc acc     240
Gly Gly Asn Ala Asn Asn Phe Lys Thr Ile Lys Glu Cys Glu Ser Thr
                 45                  50                  55 tgt gct gca tga                                                      252
Cys Ala Ala <210> SEQ ID NO 20
<211> LENGTH: 83
<212> TYPE: PRT
<213> ORGANISM: Pseudonaja textilis

<400> SEQUENCE: 20

Met Ser Ser Gly Gly Leu Leu Leu Leu Leu Gly Leu Leu Thr Leu Trp
            -20                 -15                 -10

Glu Val Leu Thr Pro Val Ser Ser Lys Asp Arg Pro Asn Phe Cys Lys
         -5                  -1   1                   5

Leu Pro Ala Glu Thr Gly Arg Cys Asn Ala Lys Ile Pro Arg Phe Tyr
         10                  15                  20

Tyr Asn Pro Arg Gln His Gln Cys Ile Glu Phe Leu Tyr Gly Gly Cys
         25                  30                  35              40

Gly Gly Asn Ala Asn Asn Phe Lys Thr Ile Lys Glu Cys Glu Ser Thr
                 45                  50                  55

Cys Ala Ala

<210> SEQ ID NO 21
<211> LENGTH: 252
<212> TYPE: DNA
<213> ORGANISM: Pseudonaja textilis
<220> FEATURE:
<221> NAME/KEY: CDS
<222> LOCATION: (1)..(249)
<220> FEATURE:
<221> NAME/KEY: sig_peptide
<222> LOCATION: (1)..(72)
<220> FEATURE:
<221> NAME/KEY: mat_peptide
<222> LOCATION: (73)..(249)

<400> SEQUENCE: 21 atg tct tct gga ggt ctt ctt ctc ctg ctg gga ctc ctc acc ctc tgg      48
Met Ser Ser Gly Gly Leu Leu Leu Leu Leu Gly Leu Leu Thr Leu Trp
            -20                 -15                 -10 gag gtg ctg acc ccc gtc tcc agc aag gac cat cca aaa ttc tgt gaa      96
Glu Val Leu Thr Pro Val Ser Ser Lys Asp His Pro Lys Phe Cys Glu
         -5                  -1   1                   5 ctc cct gct gaa acc gga tca tgt aaa ggc aac gtc cca cgc ttc tac     144
Leu Pro Ala Glu Thr Gly Ser Cys Lys Gly Asn Val Pro Arg Phe Tyr
         10                  15                  20
```

```
tac aac gca gat cat cat caa tgc cta aaa ttt att tat ggt gga tgt      192
Tyr Asn Ala Asp His His Gln Cys Leu Lys Phe Ile Tyr Gly Gly Cys
 25                  30                  35                  40 gga ggg aat gct aac aat ttt aag acc ata gag gaa ggc aaa agc acc      240
Gly Gly Asn Ala Asn Asn Phe Lys Thr Ile Glu Glu Gly Lys Ser Thr
             45                  50                  55 tgt gct gcc tga                                                      252
Cys Ala Ala
```

<210> SEQ ID NO 22
<211> LENGTH: 83
<212> TYPE: PRT
<213> ORGANISM: Pseudonaja textilis

<400> SEQUENCE: 22

```
Met Ser Ser Gly Gly Leu Leu Leu Leu Gly Leu Leu Thr Leu Trp
            -20                 -15                 -10

Glu Val Leu Thr Pro Val Ser Ser Lys Asp His Pro Lys Phe Cys Glu
             -5                  -1  1               5

Leu Pro Ala Glu Thr Gly Ser Cys Lys Gly Asn Val Pro Arg Phe Tyr
             10                  15                  20

Tyr Asn Ala Asp His His Gln Cys Leu Lys Phe Ile Tyr Gly Gly Cys
 25                  30                  35                  40

Gly Gly Asn Ala Asn Asn Phe Lys Thr Ile Glu Glu Gly Lys Ser Thr
             45                  50                  55

Cys Ala Ala
```

<210> SEQ ID NO 23
<211> LENGTH: 252
<212> TYPE: DNA
<213> ORGANISM: Pseudonaja textilis
<220> FEATURE:
<221> NAME/KEY: CDS
<222> LOCATION: (1)..(249)
<220> FEATURE:
<221> NAME/KEY: sig_peptide
<222> LOCATION: (1)..(72)
<220> FEATURE:
<221> NAME/KEY: mat_peptide
<222> LOCATION: (73)..(249)

<400> SEQUENCE: 23

```
atg tct tct gga ggt ctt ctt ctc ctg ctg gga ctc ctc acc ctc tgg      48
Met Ser Ser Gly Gly Leu Leu Leu Leu Leu Gly Leu Leu Thr Leu Trp
            -20                 -15                 -10 gag gtg ctg acc ccc gtc tcc agc aag gac cgt cca aaa ttc tgt gaa      96
Glu Val Leu Thr Pro Val Ser Ser Lys Asp Arg Pro Lys Phe Cys Glu
             -5                  -1  1               5 ctg ctt cct gac acc gga tca tgt gaa gac ttt acc gga gcc ttc cac     144
Leu Leu Pro Asp Thr Gly Ser Cys Glu Asp Phe Thr Gly Ala Phe His
             10                  15                  20 tac agc aca cgt gat cgt gaa tgc ata gag ttt att tat ggt gga tgc     192
Tyr Ser Thr Arg Asp Arg Glu Cys Ile Glu Phe Ile Tyr Gly Gly Cys
 25                  30                  35                  40 gga ggg aat gct aac aat ttt atc acc aaa gag gaa tgc gaa agc acc     240
Gly Gly Asn Ala Asn Asn Phe Ile Thr Lys Glu Glu Cys Glu Ser Thr
             45                  50                  55 tgt gct gcc tga                                                     252
Cys Ala Ala
```

<210> SEQ ID NO 24
<211> LENGTH: 83

<212> TYPE: PRT
<213> ORGANISM: Pseudonaja textilis

<400> SEQUENCE: 24

```
Met Ser Ser Gly Gly Leu Leu Leu Leu Gly Leu Leu Thr Leu Trp
            -20             -15                 -10

Glu Val Leu Thr Pro Val Ser Ser Lys Asp Arg Pro Lys Phe Cys Glu
             -5              -1   1               5

Leu Leu Pro Asp Thr Gly Ser Cys Glu Asp Phe Thr Gly Ala Phe His
         10              15               20

Tyr Ser Thr Arg Asp Arg Glu Cys Ile Glu Phe Ile Tyr Gly Gly Cys
     25              30              35              40

Gly Gly Asn Ala Asn Asn Phe Ile Thr Lys Glu Glu Cys Glu Ser Thr
                 45              50              55

Cys Ala Ala
```

<210> SEQ ID NO 25
<211> LENGTH: 252
<212> TYPE: DNA
<213> ORGANISM: Pseudonaja textilis
<220> FEATURE:
<221> NAME/KEY: CDS
<222> LOCATION: (1)..(249)
<220> FEATURE:
<221> NAME/KEY: sig_peptide
<222> LOCATION: (1)..(72)
<220> FEATURE:
<221> NAME/KEY: mat_peptide
<222> LOCATION: (73)..(249)

<400> SEQUENCE: 25

```
atg tct tct gga ggt ctt ctt ctc ctg ctg gga ctc ctc acc ctc tgg    48
Met Ser Ser Gly Gly Leu Leu Leu Leu Leu Gly Leu Leu Thr Leu Trp
            -20             -15                 -10 gag gtg ctg acc ccc gtc tcc agc aag gac cgt cca aag ttc tgt gaa    96
Glu Val Leu Thr Pro Val Ser Ser Lys Asp Arg Pro Lys Phe Cys Glu
             -5              -1   1               5 ctg cct gct gac atc gga cca tgg gat gac ttt acc gga gcc ttc cac   144
Leu Pro Ala Asp Ile Gly Pro Trp Asp Asp Phe Thr Gly Ala Phe His
         10              15               20 tac agc cca cgt gaa cat gaa tgc ata gag ttt att tat ggt gga tgc   192
Tyr Ser Pro Arg Glu His Glu Cys Ile Glu Phe Ile Tyr Gly Gly Cys
     25              30              35              40 aaa ggg aat gct aac aac ttt aat acc caa gag caa tgc gaa agc acc   240
Lys Gly Asn Ala Asn Asn Phe Asn Thr Gln Glu Gln Cys Glu Ser Thr
                 45              50              55 tgt gct gcc tga                                                    252
Cys Ala Ala
```

<210> SEQ ID NO 26
<211> LENGTH: 83
<212> TYPE: PRT
<213> ORGANISM: Pseudonaja textilis

<400> SEQUENCE: 26

```
Met Ser Ser Gly Gly Leu Leu Leu Leu Gly Leu Leu Thr Leu Trp
            -20             -15                 -10

Glu Val Leu Thr Pro Val Ser Ser Lys Asp Arg Pro Lys Phe Cys Glu
             -5              -1   1               5

Leu Pro Ala Asp Ile Gly Pro Trp Asp Asp Phe Thr Gly Ala Phe His
         10              15               20
```

```
Tyr Ser Pro Arg Glu His Glu Cys Ile Glu Phe Ile Tyr Gly Gly Cys
 25                  30                  35                  40

Lys Gly Asn Ala Asn Asn Phe Asn Thr Gln Glu Gln Cys Glu Ser Thr
                 45                  50                  55

Cys Ala Ala

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Degenerate
      sense primer
<220> FEATURE:
<221> NAME/KEY: modified_base
<222> LOCATION: (21)
<223> OTHER INFORMATION: A, T, C, G, other or unknown

<400> SEQUENCE: 27
atgaargaya grcchgaryt ngar                                          24

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Degenerate
      antisense primer

<400> SEQUENCE: 28
gtrctytcrt gytcytcy                                                 18

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Gene-
      specific forward primer for Txln1

<400> SEQUENCE: 29
atatatggat ccaaggaccg gcctgacttc                                    30

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Gene-
      specific reverse primer for Txln1

<400> SEQUENCE: 30
aacgggaatt ctcagagcca cacgtgcttt c                                  31

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Gene-
      specific reverse primer for Txln2

<400> SEQUENCE: 31
aacgggaatt ctcatgagcc acaggtagac tc                                 32

<210> SEQ ID NO 32
```

```
<211> LENGTH: 45
<212> TYPE: DNA
<213> ORGANISM: Artificial Sequence
<220> FEATURE:
<223> OTHER INFORMATION: Description of Artificial Sequence: RACE-ready
      long universal reverse primer

<400> SEQUENCE: 32
ctaatacgac tcactatagg gcaagcagtg gtaacaacgc agagt              45

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: RACE-ready
      short universal reverse primer

<400> SEQUENCE: 33
ctaatacgac tcactatagg gc                                       22

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: RACE-ready
      nested universal reverse primer

<400> SEQUENCE: 34
aagcagtggt aacaacgcag agt                                      23

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Txln1-gene
      specific forward primer

<400> SEQUENCE: 35
atcagcggat ccatgtctgg aggt                                     24

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Txln1
      gene-specific reverse primer

<400> SEQUENCE: 36
tctcctgaat tctcaggcag cacaggt                                  27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Txln-active
      peptide sequence forward primer

<400> SEQUENCE: 37
attataggat ccaaggaccg tccggat                                  27

<210> SEQ ID NO 38
<211> LENGTH: 27
```

```
<212> TYPE: DNA
<213> ORGANISM: Artificial Sequence
<220> FEATURE:
<223> OTHER INFORMATION: Description of Artificial Sequence: Gene-
      specific forward primer for txln2

<400> SEQUENCE: 38
attataggat ccaaggaccg tccagag                                        27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Gene-
      specific forward primer for Txln3

<400> SEQUENCE: 39
aacgtcggat ccaaggaccg tccaaat                                        27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Gene-
      specific forward primer for Txln4

<400> SEQUENCE: 40
aacgtcggat ccaaggacca tccaaaa                                        27

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Gene-
      specific forward primer for Txln5

<400> SEQUENCE: 41
aacgtcggat tcaaggaccg tccaaaa                                        27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Gene-
      specific forward primer for Txln6

<400> SEQUENCE: 42
attgtcggat ccaaggacct gccaaag                                        27

<210> SEQ ID NO 43
<211> LENGTH: 408
<212> TYPE: DNA
<213> ORGANISM: Pseudonaja textilis
<220> FEATURE:
<221> NAME/KEY: CDS
<222> LOCATION: (12)..(191)
<220> FEATURE:
<221> NAME/KEY: sig_peptide
<222> LOCATION: (12)..(83)
<220> FEATURE:
<221> NAME/KEY: mat_peptide
<222> LOCATION: (84)..(191)

<400> SEQUENCE: 43
```

```
ggagcttcat c atg tct tct gga ggt ctt ctt ctc ctg ctg gga ctc ctc        50
            Met Ser Ser Gly Gly Leu Leu Leu Leu Leu Leu Gly Leu Leu
                -20                     -15 acc ctc tgg gag gtg ctg acc ccc gtc tcc agc aag gac cgt cca gag         98
Thr Leu Trp Glu Val Leu Thr Pro Val Ser Ser Lys Asp Arg Pro Glu
    -10                 -5                  -1   1                5 ttg tgt gaa ctg cct cct gac acc gga cca tgt aga gtc aga tcc cca        146
Leu Cys Glu Leu Pro Pro Asp Thr Gly Pro Cys Arg Val Arg Ser Pro
                10                  15                  20 tcc ttc tac tac aac cca gat gaa caa aaa tgc cta gag ttt att           191
Ser Phe Tyr Tyr Asn Pro Asp Glu Gln Lys Cys Leu Glu Phe Ile
            25                  30                  35 tatggtggat gcgaagggaa tgctaaccaa ttttatcacc aaagaggaat gcgaaagcac      251
ctgtgctgcc tgaatgagga gaccctcctg gattggatcg acagttccaa cttgacccaa      311
agaccctgct tctgccctgg accaccctgg cacccttcc cccaaacccc acctggact        371 aattcctttt ctctgcaata aagctttggt tccagct                               408

<210> SEQ ID NO 44
<211> LENGTH: 60
<212> TYPE: PRT
<213> ORGANISM: Pseudonaja textilis

<400> SEQUENCE: 44

Met Ser Ser Gly Gly Leu Leu Leu Leu Leu Gly Leu Leu Thr Leu Trp
            -20                 -15                 -10

Glu Val Leu Thr Pro Val Ser Ser Lys Asp Arg Pro Glu Leu Cys Glu
        -5                  -1  1                   5

Leu Pro Pro Asp Thr Gly Pro Cys Arg Val Arg Ser Pro Ser Phe Tyr
    10                  15                  20

Tyr Asn Pro Asp Glu Gln Lys Cys Leu Glu Phe Ile
25                  30                  35

<210> SEQ ID NO 45
<211> LENGTH: 59
<212> TYPE: PRT
<213> ORGANISM: Artificial Sequence
<220> FEATURE:
<223> OTHER INFORMATION: Description of Artificial Sequence: Formula
      peptide
<220> FEATURE:
<221> NAME/KEY: MOD_RES
<222> LOCATION: (3)
<223> OTHER INFORMATION: Lys, Arg, His, Asp, Glu, Gln or Asn; preferably
      His or Arg
<220> FEATURE:
<221> NAME/KEY: MOD_RES
<222> LOCATION: (5)
<223> OTHER INFORMATION: Lys, Arg, His, Asp, Glu, Gln or Asn; suitably
      Lys, Asn, Glu or Asp
<220> FEATURE:
<221> NAME/KEY: MOD_RES
<222> LOCATION: (6)
<223> OTHER INFORMATION: Hydrophobic amino acid; preferably Phe or Leu
<220> FEATURE:
<221> NAME/KEY: MOD_RES
<222> LOCATION: (8)
<223> OTHER INFORMATION: Lys, Arg, His, Asp, Glu, Gln or Asn
<220> FEATURE:
<221> NAME/KEY: MOD_RES
<222> LOCATION: (10)
<223> OTHER INFORMATION: Neutral amino acid, Pro, Ala, Gly, Ser, Thr,
      Val or Leu; suitably Pro or Leu
<220> FEATURE:
<221> NAME/KEY: MOD_RES
<222> LOCATION: (11)
<223> OTHER INFORMATION: Neutral amino acid, Pro, Ala, Gly, Ser, Thr,
```

```
        Val or Leu, preferably Pro or Ala
<220> FEATURE:
<221> NAME/KEY: MOD_RES
<222> LOCATION: (12)
<223> OTHER INFORMATION: Lys, Arg, His, Asp, Glu, Gln or Asn, preferably
        Glu or Asp
<220> FEATURE:
<221> NAME/KEY: MOD_RES
<222> LOCATION: (13)
<223> OTHER INFORMATION: Neutral amino acid, Pro, Ala, Gly, Ser, Thr,
        Val or Leu, suitably Thr or Ile
<220> FEATURE:
<221> NAME/KEY: MOD_RES
<222> LOCATION: (15)
<223> OTHER INFORMATION: Any amino acid
<220> FEATURE:
<221> NAME/KEY: MOD_RES
<222> LOCATION: (17)
<223> OTHER INFORMATION: Lys, Arg, His, Asp, Glu, Gln or Asn; suitably
        Lys, Asn, Glu, Asp or Arg
<220> FEATURE:
<221> NAME/KEY: MOD_RES
<222> LOCATION: (18)
<223> OTHER INFORMATION: Any amino acid; preferably Asp, Gly, Ala or Val
<220> FEATURE:
<221> NAME/KEY: MOD_RES
<222> LOCATION: (19)
<223> OTHER INFORMATION: Any amino acid; suitably Phe, Asn, Lys or Arg
<220> FEATURE:
<221> NAME/KEY: MOD_RES
<222> LOCATION: (20)
<223> OTHER INFORMATION: Any amino acid; preferably Thr, Pro, Phe or Ile
<220> FEATURE:
<221> NAME/KEY: MOD_RES
<222> LOCATION: (21)
<223> OTHER INFORMATION: Neutral amino acid, Pro, Ala, Gly, Ser, Thr,
        Val or Leu
<220> FEATURE:
<221> NAME/KEY: MOD_RES
<222> LOCATION: (22)
<223> OTHER INFORMATION: Any amino acid; suitably Ala, Ser or Arg
<220> FEATURE:
<221> NAME/KEY: MOD_RES
<222> LOCATION: (24)
<223> OTHER INFORMATION: Aromatic amino acid; preferably Tyr or His
<220> FEATURE:
<221> NAME/KEY: MOD_RES
<222> LOCATION: (26)
<223> OTHER INFORMATION: Any amino acid; suitably Ser or Asn
<220> FEATURE:
<221> NAME/KEY: MOD_RES
<222> LOCATION: (27)
<223> OTHER INFORMATION: Neutral amoino acid, Pro, Ala, Gly, Ser, Thr,
        Val or Leu; preferably Pro, Ala or Thr
<220> FEATURE:
<221> NAME/KEY: MOD_RES
<222> LOCATION: (28)
<223> OTHER INFORMATION: Lys, Arg, His, Asp, Glu, Gln or Asn
<220> FEATURE:
<221> NAME/KEY: MOD_RES
<222> LOCATION: (29)
<223> OTHER INFORMATION: Lys, Arg, His, Asp, Glu, Gln or Asn; suitably
        Glu, Asp, His or Gln
<220> FEATURE:
<221> NAME/KEY: MOD_RES
<222> LOCATION: (30)
<223> OTHER INFORMATION: Lys, Arg, His, Asp, Glu, Gln or Asn; preferably
        His, Lys, Arg or Gln
<220> FEATURE:
<221> NAME/KEY: MOD_RES
<222> LOCATION: (31)
<223> OTHER INFORMATION: Lys, Arg, His, Asp, Glu, Gln or Asn
<220> FEATURE:
<221> NAME/KEY: MOD_RES
<222> LOCATION: (33)
<223> OTHER INFORMATION: Neutral amino acid, Pro, Ala, Gly, Ser, Thr,
        Val or Leu; preferably Leu or Ile
<220> FEATURE:
<221> NAME/KEY: MOD_RES
```

```
<222> LOCATION: (34)
<223> OTHER INFORMATION: Lys, Arg, His, Asp, Glu, Gln or Asn; suitably
      Glu or Lys
<220> FEATURE:
<221> NAME/KEY: MOD_RES
<222> LOCATION: (36)
<223> OTHER INFORMATION: Neutral amino acid, Pro, Ala, Gly, Ser, Thr,
      Val or Leu; suitably Leu or Ile
<220> FEATURE:
<221> NAME/KEY: MOD_RES
<222> LOCATION: (41)
<223> OTHER INFORMATION: Any amino acid; preferably Glu, Gly or Lys
<220> FEATURE:
<221> NAME/KEY: MOD_RES
<222> LOCATION: (42)
<223> OTHER INFORMATION: Neutral amino acid, Pro, Ala, Gly, Ser, Thr,
      Val, Leu or Cys; preferably Gly
<220> FEATURE:
<221> NAME/KEY: MOD_RES
<222> LOCATION: (48)
<223> OTHER INFORMATION: Any amino acid; suitably Lys, Asn or Ile
<220> FEATURE:
<221> NAME/KEY: MOD_RES
<222> LOCATION: (50)
<223> OTHER INFORMATION: Any amino acid; preferably Lys, Gln or Ile

<400> SEQUENCE: 45

Lys Asp Xaa Pro Xaa Xaa Cys Xaa Leu Xaa Xaa Xaa Xaa Gly Xaa Cys
  1               5                  10                  15

Xaa Xaa Xaa Xaa Xaa Xaa Phe Xaa Tyr Xaa Xaa Xaa Xaa Xaa Xaa Cys
             20                  25                  30

Xaa Xaa Phe Xaa Tyr Gly Gly Cys Xaa Xaa Asn Ala Asn Asn Phe Xaa
         35                  40                  45

Thr Xaa Glu Glu Cys Glu Ser Thr Cys Ala Ala
         50                  55

<210> SEQ ID NO 46
<211> LENGTH: 59
<212> TYPE: PRT
<213> ORGANISM: Pseudonaja textilis

<400> SEQUENCE: 46

Lys Asp Arg Pro Asp Phe Cys Glu Leu Pro Ala Asp Thr Gly Pro Cys
  1               5                  10                  15

Arg Val Arg Phe Pro Ser Phe Tyr Tyr Asn Pro Asp Glx Lys Lys Cys
             20                  25                  30

Leu Glx Phe Ile Tyr Gly Gly Cys Glu Gly Asn Ala Asn Asn Phe Ile
         35                  40                  45

Thr Lys Glu Glu Cys Glu Ser Thr Cys Gly Ser
         50                  55

<210> SEQ ID NO 47
<211> LENGTH: 59
<212> TYPE: PRT
<213> ORGANISM: Pseudonaja textilis

<400> SEQUENCE: 47

Lys Asp Arg Pro Glu Leu Cys Glu Leu Pro Pro Asp Thr Gly Pro Cys
  1               5                  10                  15

Arg Val Arg Phe Pro Ser Phe Tyr Tyr Asn Pro Asp Glu Gln Lys Cys
             20                  25                  30

Leu Glu Phe Ile Tyr Gly Gly Cys Glu Glu Asn Ala Asn Ala Phe Ile
         35                  40                  45

Thr Lys Glu Glu Cys Glu Ser Thr Cys Gly Gly
         50                  55
```

<210> SEQ ID NO 48
<211> LENGTH: 62
<212> TYPE: PRT
<213> ORGANISM: Unknown Organism
<220> FEATURE:
<223> OTHER INFORMATION: Description of Unknown Organism: Taicotoxin
    associated plasmin inhibitor

<400> SEQUENCE: 48

Lys Asp Arg Pro Lys Phe Cys His Leu Pro Pro Lys Pro Gly Pro Cys
 1               5                  10                  15

Arg Ala Ala Ile Pro Arg Phe Tyr Tyr Asn Pro His Ser Lys Gln Cys
            20                  25                  30

Glu Lys Phe Ile Tyr G

<211> LENGTH: 60
<212> TYPE: PRT
<213> ORGANISM: Pseudonaja textilis

<400> SEQUENCE: 51

Met Lys Asp Arg Pro Asp Phe Cys Glu Leu Pro Ala Asp Thr Gly Pro
1               5                   10                  15

Cys Arg Val Arg Phe Pro Ser Leu Tyr Tyr Asn Pro Asp Glu Lys Lys
                20                  25                  30

Cys Leu Glu Phe Ile Tyr Gly Gly Cys Glu Gly Asn Ala Asn Asp Phe
            35                  40                  45

Met Thr Lys Glu Glu Cys Glu Ser Thr Cys Gly Ser
        50                  55                  60

<210> SEQ ID NO 52
<211> LENGTH: 180
<212> TYPE: DNA
<213> ORGANISM: Pseudonaja textilis
<220> FEATURE:
<221> NAME/KEY: CDS
<222> LOCATION: (1)..(180)
<220> FEATURE:
<221> NAME/KEY: modified_base
<222> LOCATION: (177)
<223> OTHER INFORMATION: A, T, C or G

<400> SEQUENCE: 52 atg aag gac cgg cct gag ttg tgt gaa ctg cct cct gac acc gga cca       48
Met Lys Asp Arg Pro Glu Leu Cys Glu Leu Pro Pro Asp Thr Gly Pro
1               5                   10                  15 tgt aga gtc aga ttc cca tcc ttg tac tac aac cca gat gaa caa aaa       96
Cys Arg Val Arg Phe Pro Ser Leu Tyr Tyr Asn Pro Asp Glu Gln Lys
                20                  25                  30 tgc ctc gag ttt att tat ggt gga tgc gaa gag aat gat aac gct ttt      144
Cys Leu Glu Phe Ile Tyr Gly Gly Cys Glu Glu Asn Asp Asn Ala Phe
            35                  40                  45 atg acc aaa gag gag tgt gaa agc acg tgt ccn ggt                      180
Met Thr Lys Glu Glu Cys Glu Ser Thr Cys Pro Gly
        50                  55                  60

<210> SEQ ID NO 53
<211> LENGTH: 60
<212> TYPE: PRT
<213> ORGANISM: Pseudonaja textilis

<400> SEQUENCE: 53

Met Lys Asp Arg Pro Glu Leu Cys Glu Leu Pro Pro Asp Thr Gly Pro
1               5                   10                  15

Cys Arg Val Arg Phe Pro Ser Leu Tyr Tyr Asn Pro Asp Glu Gln Lys
                20                  25                  30

Cys Leu Glu Phe Ile Tyr Gly Gly Cys Glu Glu Asn Asp Asn Ala Phe
            35                  40                  45

Met Thr Lys Glu Glu Cys Glu Ser Thr Cys Pro Gly
        50                  55                  60

<210> SEQ ID NO 54
<211> LENGTH: 408
<212> TYPE: DNA
<213> ORGANISM: Pseudonaja textilis

<400> SEQUENCE: 54
ggagcttcat catgtcttct ggaggtcttc ttctcctgct gggactcctc accctctggg     60

```
aggtgctgac ccccgtctcc agcaaggacc gtccagagtt gtgtgaactg cctcctgaca    120
ccggaccatg tagagtcaga tccccatcct tctactacaa cccagatgaa caaaaatgcc    180
tagagtttat ttatggtgga tgcgaaggga atgctaacca attttatcac caaagaggaa    240
tgcgaaagca cctgtgctgc ctgaatgagg agaccctcct ggattggatc gacagttcca    300
acttgaccca agaccctgc ttctgccctg gaccaccctg gacacccttc ccccaaaccc     360
caccctggac taattccttt tctctgcaat aaagctttgg ttccagct                 408
```

```
<210> SEQ ID NO 55
<211> LENGTH: 83
<212> TYPE: PRT
<213> ORGANISM: Pseudonaja textilis

<400> SEQUENCE: 55
```

```
Met Ser Ser Gly Gly Leu Leu Leu Leu Gly Leu Leu Thr Leu Trp
 1               5                  10                  15

Glu Val Leu Thr Pro Val Ser Ser Lys Asp Arg Pro Asp Phe Cys Glu
                20                  25                  30

Leu Pro Ala Asp Thr Gly Pro Cys Arg Val Arg Phe Pro Ser Phe Tyr
            35                  40                  45

Tyr Asn Pro Asp Glu Lys Lys Cys Leu Glu Phe Ile Tyr Gly Gly Cys
        50                  55                  60

Glu Gly Asn Ala Asn Asn Phe Ile Thr Lys Glu Glu Cys Glu Ser Thr
65                  70                  75                  80

Cys Ala Ala
```

```
<210> SEQ ID NO 56
<211> LENGTH: 252
<212> TYPE: DNA
<213> ORGANISM: Pseudonaja textilis

<400> SEQUENCE: 56
atgtcttctg gaggtcttct tctcctgctg ggactcctca ccctctggga ggtgctgacc    60
cccgtctcca gcaaggaccg tccggatttc tgtgaactgc ctgctgacac cggaccatgt   120
agagtcagat ccccatcctt ctactacaac ccagatgaaa aaagtgcct agagtttatt    180 tatggtggat gcgaagggaa tgctaacaat tttatcacca agaggaatg cgaaagcacc    240 tgtgctgcct ga                                                       252
```

```
<210> SEQ ID NO 57
<211> LENGTH: 83
<212> TYPE: PRT
<213> ORGANISM: Pseudonaja textilis

<400> SEQUENCE: 57
```

```
Met Ser Ser Gly Gly Leu Leu Leu Leu Gly Leu Leu Thr Leu Trp
 1               5                  10                  15

Glu Val Leu Thr Pro Val Ser Ser Lys Asp Arg Pro Glu Leu Cys Glu
                20                  25                  30

Leu Pro Pro Asp Thr Gly Pro Cys Arg Val Arg Phe Pro Ser Phe Tyr
            35                  40                  45

Tyr Asn Pro Asp Glu Gln Lys Cys Leu Glu Phe Ile Tyr Gly Gly Cys
        50                  55                  60

Glu Gly Asn Ala Asn Asn Phe Ile Thr Lys Glu Glu Cys Glu Ser Thr
65                  70                  75                  80

Cys Ala Ala
```

<210> SEQ ID NO 58
<211> LENGTH: 252
<212> TYPE: DNA
<213> ORGANISM: Pseudonaja textilis

<400> SEQUENCE: 58

```
atgtcttctg gaggtcttct tctcctgctg ggactcctca ccctctggga ggtgctgacc    60
cccgtctcca gcaaggaccg tccagagttg tgtgaactgc ctcctgacac cggaccatgt   120
agagtcagat tcccatcctt ctactacaac ccagatgaac aaaaatgcct agagtttatt   180
tatggtggat gcgaagggaa tgctaacaat tttatcacca agaggaatg cgaaagcacc    240
tgtgctgcct ga                                                       252
```

<210> SEQ ID NO 59
<211> LENGTH: 83
<212> TYPE: PRT
<213> ORGANISM: Pseudonaja textilis

<400> SEQUENCE: 59

Met Ser Ser Gly Gly Leu Leu Leu Leu Gly Leu Leu Thr Leu Trp
 1               5                  10                  15

Glu Val Leu Thr Pro Val Ser Ser Lys Asp Arg Pro Asn Phe Cys Lys
            20                  25                  30

Leu Pro Ala Glu Thr Gly Arg Cys Asn Ala Lys Ile Pro Arg Phe Tyr
        35                  40                  45

Tyr Asn Pro Arg Gln His Gln Cys Ile Glu Phe Leu Tyr Gly Gly Cys
    50                  55                  60

Gly Gly Asn Ala Asn Asn Phe Lys Thr Ile Lys Glu Cys Glu Ser Thr
65                  70                  75                  80

Cys Ala Ala

<210> SEQ ID NO 60
<211> LENGTH: 252
<212> TYPE: DNA
<213> ORGANISM: Pseudonaja textilis

<400> SEQUENCE: 60

```
atgtcttctg gaggtcttct tctcctgctg ggactcctca ccctctggga ggtgctgacc    60
cccgtctcca gcaaggaccg tccaaatttc tgtaaactgc ctgctgaaac cggacgatgt   120
aatgccaaaa tcccacgctt ctactacaac ccacgtcaac atcaatgcat agagtttctc   180
tatggtggat gcggagggaa tgctaacaat tttaagacca ttaaggaatg cgaaagcacc   240
tgtgctgcat ga                                                       252
```

<210> SEQ ID NO 61
<211> LENGTH: 83
<212> TYPE: PRT
<213> ORGANISM: Pseudonaja textilis

<400> SEQUENCE: 61

Met Ser Ser Gly Gly Leu Leu Leu Leu Gly Leu Leu Thr Leu Trp
 1               5                  10                  15

Glu Val Leu Thr Pro Val Ser Ser Lys Asp His Pro Lys Phe Cys Glu
            20                  25                  30

Leu Pro Ala Asp Thr Gly Ser Cys Lys Gly Asn Pro Val Arg Phe Tyr
        35                  40                  45

```
Tyr Asn Ala Asp His His Gln Cys Leu Lys Phe Ile Tyr Gly Gly Cys
         50                  55                  60

Gly Gly Asn Ala Asn Asn Phe Lys Thr Ile Glu Glu Cys Lys Ser Thr
 65                  70                  75                  80

Cys Ala Ala
```

<210> SEQ ID NO 62
<211> LENGTH: 252
<212> TYPE: DNA
<213> ORGANISM: Pseudonaja textilis

<400> SEQUENCE: 62

```
atgtcttctg gaggtcttct tctcctgctg ggactcctca ccctctggga ggtgctgacc       60
cccgtctcca gcaaggacca tccaaaattc tgtgaactcc ctgctgaaac cggatcatgt      120
aaaggcaacg tcccacgctt ctactacaac gcagatcatc atcaatgcct aaaatttatt      180
tatggtggat gtggagggaa tgctaacaat tttaagacca tagaggaagg caaaagcacc      240
tgtgctgcct ga                                                         252
```

<210> SEQ ID NO 63
<211> LENGTH: 83
<212> TYPE: PRT
<213> ORGANISM: Pseudonaja textilis

<400> SEQUENCE: 63

```
Met Ser Ser Gly Gly Leu Leu Leu Leu Gly Leu Leu Thr Leu Trp
  1               5                  10                  15

Glu Val Leu Thr Pro Val Ser Ser Lys Asp Arg Pro Lys Phe Cys Glu
                 20                  25                  30

Leu Leu Pro Asp Thr Gly Ser Cys Glu Asp Phe Thr Gly Ala Phe His
         35                  40                  45

Tyr Ser Thr Arg Asp Arg Glu Cys Ile Glu Phe Ile Tyr Gly Gly Cys
         50                  55                  60

Gly Cys Asn Ala Asn Asn Phe Ile Thr Lys Glu Glu Cys Glu Ser Thr
 65                  70                  75                  80

Cys Ala Ala
```

<210> SEQ ID NO 64
<211> LENGTH: 252
<212> TYPE: DNA
<213> ORGANISM: Pseudonaja textilis

<400> SEQUENCE: 64

```
atgtcttctg gaggtcttct tctcctgctg ggactcctca ccctctggga ggtgctgacc       60
cccgtctcca gcaaggaccg tccaaaattc tgtgaactgc ttcctgacac cggatcatgt      120
gaagactta ccggagcctt ccactacagc acacgtgatc gtgaatgcat agagtttatt       180
tatggtggat gcggagggaa tgctaacaat tttatcacca agaggaatg cgaaagcacc       240
tgtgctgcct ga                                                         252
```

<210> SEQ ID NO 65
<211> LENGTH: 83
<212> TYPE: PRT
<213> ORGANISM: Pseudonaja textilis

<400> SEQUENCE: 65

```
Met Ser Ser Gly Gly Leu Leu Leu Leu Gly Leu Leu Thr Leu Trp
  1               5                  10                  15
```

```
Glu Val Leu Thr Pro Val Ser Ser Lys Asp Arg Pro Lys Phe Cys Glu
             20                  25                  30

Leu Pro Ala Asp Ile Gly Pro Cys Asp Asp Phe Thr Gly Ala Phe His
         35                  40                  45

Tyr Ser Pro Arg Glu His Glu Cys Ile Glu Phe Ile Tyr Gly Gly Cys
     50                  55                  60

Lys Gly Asn Ala Asn Asn Phe Asn Thr Gln Glu Cys Glu Ser Thr
 65                  70                  75                  80

Cys Ala Ala

<210> SEQ ID NO 66
<211> LENGTH: 252
<212> TYPE: DNA
<213> ORGANISM: Pseudonaja textilis

<400> SEQUENCE: 66
atgtcttctg gaggtcttct tctcctgctg ggactcctca ccctctggga ggtgctgacc      60
cccgtctcca gcaaggaccg tccaaagttc tgtgaactgc ctgctgacat cggaccatgg    120
gatgacttta ccggagcctt ccactacagc ccacgtgaac atgaatgcat agagtttatt    180
tatggtggat gcaaagggaa tgctaacaac tttaatcccc aagagcaatg cgaaagcacc    240
tgtgctgcct ga                                                        252

<210> SEQ ID NO 67
<211> LENGTH: 59
<212> TYPE: PRT
<213> ORGANISM: Artificial Sequence
<220> FEATURE:
<223> OTHER INFORMATION: Description of Artificial Sequence: Formula
      peptide
<220> FEATURE:
<221> NAME/KEY: MOD_RES
<222> LOCATION: (3)
<223> OTHER INFORMATION: Lys, Arg, His, Asp, Glu, Gln or Asn
<220> FEATURE:
<221> NAME/KEY: MOD_RES
<222> LOCATION: (5)
<223> OTHER INFORMATION: Lys, Arg, His, Asp, Glu, Gln or Asn
<220> FEATURE:
<221> NAME/KEY: MOD_RES
<222> LOCATION: (6)
<223> OTHER INFORMATION: Hydrophobic amino acid
<220> FEATURE:
<221> NAME/KEY: MOD_RES
<222> LOCATION: (8)
<223> OTHER INFORMATION: Lys, Arg, His, Asp, Glu, Gln or Asn
<220> FEATURE:
<221> NAME/KEY: MOD_RES
<222> LOCATION: (10)..(11)
<223> OTHER INFORMATION: Neutral amino acid, Pro, Ala, Gly, Ser, Thr,
      Val or Leu
<220> FEATURE:
<221> NAME/KEY: MOD_RES
<222> LOCATION: (12)
<223> OTHER INFORMATION: Lys, Arg, His, Asp, Glu, Gln or Asn
<220> FEATURE:
<221> NAME/KEY: MOD_RES
<222> LOCATION: (13)
<223> OTHER INFORMATION: Neutral amino acid, Pro, Ala, Gly, Ser, Thr,
      Val or Leu
<220> FEATURE:
<221> NAME/KEY: MOD_RES
<222> LOCATION: (15)
<223> OTHER INFORMATION: Any amino acid from Table 1 or Table 2 in the
      specification as filed
<220> FEATURE:
<221> NAME/KEY: MOD_RES
<222> LOCATION: (17)
```

```
<223> OTHER INFORMATION: Lys, Arg, His, Asp, Glu, Gln or Asn
<220> FEATURE:
<221> NAME/KEY: MOD_RES
<222> LOCATION: (18)..(20)
<223> OTHER INFORMATION: Any amino acid from Table 1 or Table 2 in the
      specification as filed
<220> FEATURE:
<221> NAME/KEY: MOD_RES
<222> LOCATION: (21)
<223> OTHER INFORMATION: Neutral amino acid, Pro, Ala, Gly, Ser, Thr,
      Val or Leu
<220> FEATURE:
<221> NAME/KEY: MOD_RES
<222> LOCATION: (22)
<223> OTHER INFORMATION: Any amino acid from Table 1 or Table 2 in the
      specification as filed
<220> FEATURE:
<221> NAME/KEY: MOD_RES
<222> LOCATION: (24)
<223> OTHER INFORMATION: Aromatic amino acid
<220> FEATURE:
<221> NAME/KEY: MOD_RES
<222> LOCATION: (26)
<223> OTHER INFORMATION: Any amino acid from Table 1 or Table 2 in the
      specification as filed
<220> FEATURE:
<221> NAME/KEY: MOD_RES
<222> LOCATION: (27)
<223> OTHER INFORMATION: Neutral amino acid, Pro, Ala, Gly, Ser, Thr,
      Val or Leu
<220> FEATURE:
<221> NAME/KEY: MOD_RES
<222> LOCATION: (28)..(31)
<223> OTHER INFORMATION: Lys, Arg, His, Asp, Glu, Gln or Asn
<220> FEATURE:
<221> NAME/KEY: MOD_RES
<222> LOCATION: (33)
<223> OTHER INFORMATION: Neutral amino acid, Pro, Ala, Gly, Ser, Thr,
      Val or Leu
<220> FEATURE:
<221> NAME/KEY: MOD_RES
<222> LOCATION: (34)
<223> OTHER INFORMATION: Lys, Arg, His, Asp, Glu, Gln or Asn
<220> FEATURE:
<221> NAME/KEY: MOD_RES
<222> LOCATION: (36)
<223> OTHER INFORMATION: Neutral amino acid, Pro, Ala, Gly, Ser, Thr,
      Val or Leu
<220> FEATURE:
<221> NAME/KEY: MOD_RES
<222> LOCATION: (41)
<223> OTHER INFORMATION: Any amino acid from Table 1 or Table 2
      in the specification as filed
<220> FEATURE:
<221> NAME/KEY: MOD_RES
<222> LOCATION: (42)
<223> OTHER INFORMATION: Neutral amino acid, Pro, Ala, Gly, Ser, Thr,
      Val, Leu or Cys
<220> FEATURE:
<221> NAME/KEY: MOD_RES
<222> LOCATION: (48)
<223> OTHER INFORMATION: Any amino acid from Table 1 or Table 2 in the
      specification as filed
<220> FEATURE:
<221> NAME/KEY: MOD_RES
<222> LOCATION: (50)
<223> OTHER INFORMATION: Any amino acid from Table 1 or Table 2 in the
      specification as filed

<400> SEQUENCE: 67

Lys Asp Xaa Pro Xaa Xaa Cys Xaa Leu Xaa Xaa Xaa Xaa Gly Xaa Cys
  1               5                  10                  15

Xaa Xaa Xaa Xaa Xaa Xaa Phe Xaa Tyr Xaa Xaa Xaa Xaa Xaa Xaa Cys
             20                  25                  30

Xaa Xaa Phe Xaa Tyr Gly Gly Cys Xaa Xaa Asn Ala Asn Asn Phe Xaa
             35                  40                  45
```

```
Thr Xaa Glu Glu Cys Glu Ser Thr Cys Ala Ala
    50                  55

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Cys Glu Ser Thr Cys Ala Ala
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asn Ala Asn Asn Phe
1               5

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Gly Gly Cys
1
```